(12) United States Patent
Duvick et al.

(10) Patent No.: US 6,555,732 B1
(45) Date of Patent: Apr. 29, 2003

(54) RAC-LIKE GENES AND METHODS OF USE

(75) Inventors: Jonathan P. Duvick, Des Moines, IA (US); Yogesh Kumar Sharma, Maryland Heights, MO (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/391,741

(22) Filed: Sep. 8, 1999

Related U.S. Application Data

(60) Provisional application No. 60/111,919, filed on Dec. 11, 1998, and provisional application No. 60/100,284, filed on Sep. 14, 1998.

(51) Int. Cl.$^7$ .......... C12N 15/29; C12N 15/82; C12N 1/16; C12N 1/20; A01H 5/00
(52) U.S. Cl. .......... 800/279; 800/278; 800/298; 800/295; 800/286; 800/320; 800/320.1; 435/69.1; 435/320.1; 435/419; 435/468; 435/252.3; 435/254.2; 435/325; 536/23.2; 536/23.6; 536/24.1; 536/24.5
(58) Field of Search .......... 536/23.2, 24.1, 536/24.5, 23.6; 435/69.1, 419, 468, 320.1, 252.3, 254.2, 325; 800/320, 320.1, 278, 298, 286, 279, 295

(56) References Cited

U.S. PATENT DOCUMENTS 5,629,470 A * 5/1997 Lam et al. .......... 800/205

FOREIGN PATENT DOCUMENTS

| WO | WO 95/14784 | 6/1995 |
| WO | WO 97/18303 | 5/1997 |

OTHER PUBLICATIONS

Salah et al, "Control of Leaf Expansion Rate of Droughted Maize Plants under Fluctuating Evaporative Demand", 1997, Plant Physiol. vol. 114, pp. 893–900.*
Hillier et al, Sequence Search Results, Accession No. N59260.*
Asgari et al, Sequence Search Results, Accession No.s AAX05267and AAQ55856.*
Sasaki et al, Sequence Search Results, Accession No. D48393.*
GenBank Accession No. AF079485.*
Winge et al. Cloning and Characterization of Rac–like cDNAs from Arabidopsis thaliana. Plant Mol. Biol. vol. 35, (4) pp. 483–495, 1997.*
Ridley et al. The Small GTP–Binding Protein rac Regulates Growth Factor–Induced Membrane Ruffling. Cell, vol. 70, pp. 401–410, 1992.*
Westwick, et al. Rac Regulation of Transformation, Gene Expression, and Actin Organization by Multiple, PAK–Independent Pathways. Mol. and Cell. Biol, vol. 17, No. 3, pp. 1324–1335, 1997.*

Ono, E., et al., "Essential Role of the Small GTPase Rac in Disease Resistance of Rice," *PNAS*, Jan. 16, 2001, pp. 759–764, vol. 98, No. 2.
Valster, A.H. et al., "Plant GTPases: The Rhos in Bloom," *Trends in Cell Biology*, Apr. 2000, pp. 141–146, vol. 10.
Knaus, et al., 1991, *Science*, 254: 1512–1515, "Regulation of phagocyte oxygen radical production by the GTP–binding protein Rac 2".
Kohl, et al., 1993, *Science*, 260: 1934–1937, "Selective Inhibition of ras–Dependent Transformation by a Farnesyl-transferase Inhibitor".
Kleinberg, et al., 1994, *Biochemistry*, 33:2490–2495, "p21rac Does Not Participate in the Early Interaction between p47–phox and cytochrome $b_{558}$ That Leads to Phagocyte NADPH Oxidase Activation in Vitro".
Diekmann, et al., 1994 *Science*, 265: 531–533, "Interaction of Rac with p67$^{phox}$ and Regulation of Phagocytic NADPH Oxidase Activity".
Heyworth, et al., 1994, *J. Biol. Chem.*, 269: 30749–30752, "Rac Translocates Independently of the Neutrophil NADPH Oxidase Components p47$^{phox}$ and p67$^{phox}$".
Mehdy, Mona, 1994, *Plant Physiol*, 105: 467–472, "Active Oxygen Species in Plant Defense against Pathogens".
Low, et al., 1994, *Adv. Mol. Genetics of Plant–Microbe Interactions*, 3: 361–369, "Comparison of the Oxidative Burst Signaling Pathways of Plants and Human Neutrophils".
Bokoch, Gary, 1994, *Cell Biology*, 6: 212–218, "Regulation of the human neutrophil NADPH oxidase by the Rac GTP-binding proteins".
Kwong, et al., 1995, *J. Biol. Chem.*, 270: 19868–19872, "Characterization of the Effector–specifying Domain of Rac Involved in NADPH Oxidase Activation".
Prigmore, et al., 1995, *J. Biol. Chem.*, 270: 10717–10722, "A 68–kDa Kinase and NADPH Oxidase Component p67$^{phox}$ Are Targets for Cdc42Hs and Rac1 in Neutrophils".
Hill, et al., 1995, *Cell*, 81: 1159–1170, "The Rho Family GTPases RhoA, Rac1, and CDC42Hs Regulate Transcriptional Activation by SRF".

(List continued on next page.)

*Primary Examiner*—David T. Fox
*Assistant Examiner*—Medina A. Ibrahim
(74) *Attorney, Agent, or Firm*—Alston & Bird LLP

(57) ABSTRACT

The present invention provides methods and compositions relating to creating or enhancing disease resistance in plants. The invention provides isolated maize Rac nucleic acids and their encoded proteins that are involved in the altering the disease resistance pathway in plants, increasing transformation efficiency, inducing programmed cell death, and modulating the oxidative burst in a plant. The invention further provides recombinant expression cassettes, host cells, transgenic plants, and antibody compositions.

29 Claims, No Drawings

OTHER PUBLICATIONS

Minden, et al., 1995, *Cell,* 81: 1147–1157, "Selective Activation of the JNK Signaling Cascade and c–Jun Transcriptional Activity by the Small GTPases Rac and Cdc42Hs".

Coso, et al., 1995, *Cell,* 81: 1137–1146, "The Small GTP-Binding Proteins Rac1 and Cdc42 Regulate the Activity of the JNK–SAPK Signaling Pathway".

Voncken, et al., 1995, *Cell,* 80: 719–728, "Increased Neutrophil Respiratory Burst in bcr–Null Mutants".

Olson, et al., 1995, *Science,* 269: 1270–1272, "An Essential Role for Rho, Rac, and Cdc42 GTPases in Cell Cycle Progression Through $G_1$".

Nobes, et al., 1995, *Cell,* 81: 53–62, "Rho, Rac, and Cdc42 GTPases Regulate the Assembly of Multimolecular Focal Complexes Associated with Actin Stress Fibers, Lamellipodia, and Filopodia".

Wu, et al., 1995, *The Plant Cell,* 7: 1357–1368, "Disease Resistance Conferred by Expression of a Gene Encoding $H_2O_2$–Generating Glucose Oxidase in Transgenic Potato Plants".

Dusi, et al., 1996, *Biochemical J.,* 314:409–412, "Mechanisms of NADPH oxidase activation: translocation of $p40_{phox}$, Rac1 and Rac2 from the cytosol to the membranes in human neutrophils lacking $p47_{phox}$ or $p67_{phox}$".

Chandra, et al., 1996, *Proc. Natl. Acad. Sci.,* 93:13393–13397, "The Pto kinase mediates a signaling pathway leading to the oxidative burst in tomato".

Sundaresan, et al., 1996, *Biochem. J.,* 318: 379–382, "Regulation of reactive–oxygen–species generation in fibroblasts by Rac1".

Symons, Marc, 1996, *Reviews,* 21: 178–181, "Rho family GTPases: the cytoskeleton and beyond".

Sulciner, et al., 1996, *Mol. and Cell. Biol.,* 16: 7115–7121, "rac1 Regulates a Cytokine–Stimulated, Redox–Dependent Pathway Necessary for $NF-_\kappa B$ Activation".

Chen, et al., 1996, *Science,* 274: 2115–2118, "Requirement of CDC42 for Salmonella–Induced Cytoskeletal and Nuclear Responses".

Larochelle, et al., 1996, *J. Cell Biol.,* 133: 1321–1329, "A Novel Member of the rho Family of Small GTP–binding Proteins Is Specifically Required for Cytokinesis".

Dutartre, et al., 1996, *J. Cell Science,* 109: 367–377, "Cytokinesis arrest and redistribution of actin–cytoskeleton regulatory components in cells expressing the Rho GTPase CDC42Hs".

Borg, et al., 1997, *The Plant J.,* 11(2): 237–250, "Identification of new protein species among 33 different small GTP–binding proteins encoded by cDNAs from Lotus japonicus, and expression of corresponding mRNAs in developing root nodules".

Pugin, et al., 1997, *The Plant Cell,* 9: 2077–2091, "Early Events Induced by the Elicitor Cryptogein in Tobacco Cells: Involvement of a Plasma Membrane NADPH Oxidase and Activation of Glycolysis and the Pentose Phosphate Pathway".

Kieffer, et al., 1997, *FEBS,* 403: 149–153, "Tobacco cells contain a protein, immunologically related to the neutrophil small G protein Rac2 and involved in elicitor–induced oxidative burst".

Irani, et al., 1997, *Science,* 275: 1649–1652, "Mitogenic Signaling Mediated by Oxidants in Ras–Transformed Fibroblasts".

Lin, et al., 1997, *The Plant Cell,* 9: 1647–1659, "Inhibition of Pollen Tube Elongation by Microinjected Anti–Rop1Ps Antibodies Suggests a Crucial Role for Rho–Type GTPases in the Control of Tip Growth".

Lores, et al., 1997, *Oncogene,* 15: 601–605, "Enhanced apoptosis in the thymus of transgenic mice expressing constitutively activated forms of human Rac2GTPase".

Winge, et al., 1997, *Plant Mol. Biol.,* 35: 483–495, "Cloning and characterization of rac–like cDNAs from *Arabidopsis thaliana*".

Xing, et al., 1997, *The Plant Cell,* 9: 249–259, "Race–Specific Elicitors of Cladosporium fulvum Promote Translocation of Cytosolic Components of NADPH Oxidase to the Plasma Membrane of Tomato Cells".

Westiwick, et al., 1997, *Mol. and Cell. Biol.,* 17: 1324–1335, "Rac Regulation of Transformation, Gene Expression, and Actin Organization by Multiple, PAK–Independent Pathways".

Slotman, Gus, 1997, *J. of Critical Illness,* 12: 691–696, "Invasive fungal infections: Deadly and on the rise".

Xu, et al., 1997, *Biochemistry,* 36: 626–632, "Guanine Nucleotide Binding Properties of Rac2 Mutant Proteins and Analysis of the Responsiveness to Guanine Nucleotide Dissociation Stimulator".

Toporik, et al., 1998, *Biochemistry,* 37: 7147–7156, "Mutational Analysis of Novel Effector Domains in Rac1 Involved in the Activation of Nicotinamide Adenine Dinucleotide Phosphate (Reduced) Oxidase".

Kheradmand, et al., *Science,* 280:898–902, "Role of Rac1 and Oxygen Radicals in Collagenase–1 Expression Induced by Cell Shape Change".

Li, H., et al., 1997, *EMBL Accession No. AF031427,* "*Arabidopsis thaliana* Rho–like GTP binding protein (Rop6) mRNA, complete cds".

Xia, G., et al., 1997, *EMBL Accession No. U62746,* "*Arabidopsis thaliana* Rho1Ps homolog mRNA, complete cds".

Xia, G., et al., 1996, *The Plant Journal,* 10: 761–769, "Identification of plant cytoskeletal, cell cycle–related and polarity–related proteins using Schizosaccharomyces pombe".

Sasaki, T., et al., 1995, *EMBL Accession No. D48393,* DEBST ID: 146316.

Borg, et al., 1996, *EMBL Accession No. Z73961,* "Identification of New protein species among 33 different small GTP–binding proteins encoded by cDNAs from Lotus japonicus, and expression of corresponding mRNAs in developing root nodules".

Borg, et al., 1996, *EMBL Accession No., Z73962,* "Identification of new protein species among 33 different small GTP–binding proteins encoded by cDNAs from Lotus Japonicus, and expression of corresponding mRNAs in developing root nodules".

Li, H., et al., 1997, *EMBL Accession No. U49972,* "*Arabidopsis thaliana* GTP binding protein Rop2AT (Rop2At) mRNA, complete cds".

Li, H., et al., 1997, *EMBL Accession No. U49971,* "*Arabidopsis thaliana* GTP binding protein Rop1AT (Rop1At) mRNA, complete cds".

Dallery, E., et al., 1995, *EMBL Accession No. Z49191,* "*B. vulgaris* mRNA for small G protein (clone 185)".

Sasaki, 1997, *EMBL Accession No. C72752,* DBEST ID: 1290351.

Minobe, et al., 1993, *EMBL Accession No. D23963,* DBEST ID: 37272.

Yang, et al., 1993, *Proc. Natl. Acad. Sci, USA*, 90: 8732–8736, "Molecular cloning and characterization of rho, a ras–related small GTP–binding protein from the garden pea".

Yang, et al., 1994, *EMBL Accession No. L19093*, "Pisum sativum rho (ras–related0 GTP–binding protein mRNA, complete cd".

Sasaki, T., et al., 1997, *EMBL Accession No. C73805*, DBEST ID: 1296189.

Sasaki, T., et al., 1997, *EMBL Accession No. C26882*, DBEST ID: 1195078.

Kawasaki, et al., 1999, *Proc. Natl. Acad. Sci. USA*, 96: 10922–10926, "The small GTP–binding protein Rac is a regulator of cell death in plants".

Hassanain, H.H., et al., 1999, *EMBL Accession No. AF126052*, "*Zea mays* RACA small GTP binding protein mRNA, complete cds".

Hassanain, H.H., et al., 1999, *EMBL Accession No. AF126053*, "*Zea mays* RACB small GTP binding protein mRNA, complete cds".

Hassanain, H.H., et al., 1999, *EMBL Accession No. AF126054*, "*Zea mays* RACC small GTP binding protein mRNA, complete cds".

Hassanain, H.H., et al., 1999, *EMBL Accession No. AF126055*, "*Zea mays* RACD small GTP binding protein mRNA, complete cds".

Winge, P., et al., 1998, *EMBL Accession No. AF079486*, "*Arabidopsis thaliana* rac GTP binding protein Arac8 (Arac8) mRNA, complete cds".

Winge, P., et al., 1998, *EMBL Accession No. AF079485*, "*Arabidopsis thaliana* rac GTP binding protein Arac10 (Arac10) mRNA, complete cds".

Winge, P., et al., 1998, *EMBL Accession No. AF079487*, "*Arabidopsis thaliana* rac–like GTP binding protein Arac6 (Arac6) mRNA, complete cds".

Winge, P., et al., 1998, *EMBL Accession No. AF079484*, "*Arabidopsis thaliana* rac GTP binding protein Arac7 (Arac7) mRNA, complete cds".

Sasaki, et al., 1998, *EMBL Accession No. AU029919*, DBEST ID: 1975300.

Wu, et al., 1997, *Plant Physiol.*, 115: 427–435, "Activation of Host Defense Mechanisms by Elevated Production of $H_2O_2$ in Transgenic Plants".

Dangl, et al., 1996, *The Plant Cell*, 8: 1793–1807, "Death Don't Have No Mercy: Cell Death Programs in Plant–Microbe Interaction".

Wojtaszek, P., 1997, *Biochem. J.*, 322: 681–692, "Oxidative burst: an early plant response to pathogen infection".

* cited by examiner

SEQUENCE LISTING

<160> NUMBER OF SEQ ID NOS: 51

<210> SEQ ID NO 1
<211> LENGTH: 1127
<212> TYPE: DNA
<213> ORGANISM: Zea mays
<220> FEATURE:
<221> NAME/KEY: CDS
<222> LOCATION: (190)...(831)

<400> SEQUENCE: 1

```
gtcgacccac gcgtccgccc agaagtcacg caccaaacac caccaccaaa gaaggcgaga         60
acgtactccg tccctcccct cccctcccct ccccttcccc tcgaggctcc aggaccgtct        120
cctcgcctgc tcatccgccg ctgcttccct tctctgggct cggagaaccg gagagaagcg        180 cgcgcggcc atg gcg tcc agc gcc tct cgg ttc atc aag tgc gtc acg gtc        231
          Met Ala Ser Ser Ala Ser Arg Phe Ile Lys Cys Val Thr Val
            1               5                  10 ggc gac ggt gcc gtg ggc aag aca tgt atg ctc atc tgc tac acc agc          279
Gly Asp Gly Ala Val Gly Lys Thr Cys Met Leu Ile Cys Tyr Thr Ser
 15                  20                  25                  30 aac aag ttc ccc act gac tac ata cct acg gtg ttc gac aat ttc agt          327
Asn Lys Phe Pro Thr Asp Tyr Ile Pro Thr Val Phe Asp Asn Phe Ser
                 35                  40                  45 gca aat gta gtt gtg gat ggc acc act gtg aat ttg ggc ctt tgg gat          375
Ala Asn Val Val Val Asp Gly Thr Thr Val Asn Leu Gly Leu Trp Asp
             50                  55                  60 acc gct ggg cag gaa gat tac aac cgc ctg agg cct cta agc tac cga          423
Thr Ala Gly Gln Glu Asp Tyr Asn Arg Leu Arg Pro Leu Ser Tyr Arg
 65                  70                  75 ggt gca gat gtt ttc gtg ctt gca ttc tca ctt gtg agc cga gct agc          471
Gly Ala Asp Val Phe Val Leu Ala Phe Ser Leu Val Ser Arg Ala Ser
         80                  85                  90 tat gag aat atc atg aag aag tgg ata cca gag ctt caa cat tat gca          519
Tyr Glu Asn Ile Met Lys Lys Trp Ile Pro Glu Leu Gln His Tyr Ala
 95                 100                 105                 110 cct ggg gtg ccc gtt gtt ttg gca ggc aca aaa ttg gat ctt cgt gaa          567
Pro Gly Val Pro Val Val Leu Ala Gly Thr Lys Leu Asp Leu Arg Glu
                115                 120                 125 gac aag cac tac ttg atg gac cat cct gga ttg gtg cct gtt acc act          615
Asp Lys His Tyr Leu Met Asp His Pro Gly Leu Val Pro Val Thr Thr
            130                 135                 140 gca cag ggg gag gaa ctt cgt aga caa att ggt gct atg tat tac att          663
Ala Gln Gly Glu Glu Leu Arg Arg Gln Ile Gly Ala Met Tyr Tyr Ile
        145                 150                 155 gaa tgc agc tca aag aca cag cag aat gtc aaa gct gtg ttc gat gct          711
Glu Cys Ser Ser Lys Thr Gln Gln Asn Val Lys Ala Val Phe Asp Ala
            160                 165                 170 gcc atc aag gta gta atc cag cct cca act aaa ata aga gaa aag aag          759
Ala Ile Lys Val Val Ile Gln Pro Pro Thr Lys Ile Arg Glu Lys Lys
175                 180                 185                 190 aag aaa aaa tca cgc aaa gga tgt tct atg atg aac atc ttc ggt gga          807
```

```

Lys Lys Lys Ser Arg Lys Gly Cys Ser Met Met Asn Ile Phe Gly Gly
            195                 200                 205 aga aaa atg cta tgc ttc aag tcc tgaatggttc aagggggtct tacatggact        861
Arg Lys Met Leu Cys Phe Lys Ser
            210 gataccacga gtgtgacccc gagtttgcga agcttgaaat cttgatgtgc tcgttgcgca       921 tgtgtatatt tgcacctttg gttattaatg actagaggta ggtaattgaa actagtctgc       981 ttaagcgttc tgcactgctg gtgtggttag ctctatgagt taagcagttc gacagaggcc      1041 aaaccgacag tgagattttg ttctttcatg gaaatgtgcc aatgtcacag cttttcgtg       1101 aaaaaaaaaa aaaaaaaaa aaaaaa                                            1127
```

<210> SEQ ID NO 2
<211> LENGTH: 214
<212> TYPE: PRT
<213> ORGANISM: Zea mays

<400> SEQUENCE: 2

```
Met Ala Ser Ser Ala Ser Arg Phe Ile Lys Cys Val Thr Val Gly Asp
 1               5                  10                  15

Gly Ala Val Gly Lys Thr Cys Met Leu Ile Cys Tyr Thr Ser Asn Lys
            20                  25                  30

Phe Pro Thr Asp Tyr Ile Pro Thr Val Phe Asp Asn Phe Ser Ala Asn
        35                  40                  45

Val Val Val Asp Gly Thr Thr Val Asn Leu Gly Leu Trp Asp Thr Ala
    50                  55                  60

Gly Gln Glu Asp Tyr Asn Arg Leu Arg Pro Leu Ser Tyr Arg Gly Ala
65                  70                  75                  80

Asp Val Phe Val Leu Ala Phe Ser Leu Val Ser Arg Ala Ser Tyr Glu
                85                  90                  95

Asn Ile Met Lys Lys Trp Ile Pro Glu Leu Gln His Tyr Ala Pro Gly
            100                 105                 110

Val Pro Val Val Leu Ala Gly Thr Lys Leu Asp Leu Arg Glu Asp Lys
        115                 120                 125

His Tyr Leu Met Asp His Pro Gly Leu Val Pro Val Thr Thr Ala Gln
    130                 135                 140

Gly Glu Glu Leu Arg Arg Gln Ile Gly Ala Met Tyr Tyr Ile Glu Cys
145                 150                 155                 160

Ser Ser Lys Thr Gln Gln Asn Val Lys Ala Val Phe Asp Ala Ala Ile
                165                 170                 175

Lys Val Val Ile Gln Pro Pro Thr Lys Ile Arg Glu Lys Lys Lys Lys
            180                 185                 190

Lys Ser Arg Lys Gly Cys Ser Met Met Asn Ile Phe Gly Gly Arg Lys
        195                 200                 205

Met Leu Cys Phe Lys Ser
    210
```

<210> SEQ ID NO 3
<211> LENGTH: 1393
<212> TYPE: DNA
<213> ORGANISM: Zea mays
<220> FEATURE:
<221> NAME/KEY: CDS
<222> LOCATION: (398)...(988)

<400> SEQUENCE: 3

```
gtcgacccac gcgtccgcgg acgcgtgggc ggacgcgtgg gtccccaccc accaccgcgc         60
```

-continued

```
cgggccacca ccacccactc taccctcccc tccccaccac cactagcacc caccgtcccg    120
gcgcggagac cgcttccctc cctccgcctc cgcaaccctc tccgcctcg cccgcgcctc     180 cctccatttg tccgcggctc ccctccctcc cgatcttaac caccccgccac ccggcttcct   240 ctccccttc ttcctccctc aaaccagacg ctcgccccc tttcctccac gcctatcttc      300
ttcagacgac cagcaggagg tacgaggaag accacctagg aggcctctct ctctctctcc    360
ccagccaccc ccgtagcgag agggagggcg gaagagg atg agc gcg tcc agg ttc     415
                                          Met Ser Ala Ser Arg Phe
                                           1               5 ata aag tgc gtc acg gtc ggg gac ggc gcc gtc ggc aag acc tgc atg      463
Ile Lys Cys Val Thr Val Gly Asp Gly Ala Val Gly Lys Thr Cys Met
             10                  15                  20 ctc atc tcc tac acc tcc aac acc ttc ccc acc gac tat gtt ccg aca      511
Leu Ile Ser Tyr Thr Ser Asn Thr Phe Pro Thr Asp Tyr Val Pro Thr
         25                  30                  35 gtg ttt gat aac ttc agt gcc aac gtt gtg gtt gat ggt aat act gtc      559
Val Phe Asp Asn Phe Ser Ala Asn Val Val Val Asp Gly Asn Thr Val
     40                  45                  50 aac ctc ggc ctc tgg gac act gca ggt caa gag gat tac aac aga ctg      607
Asn Leu Gly Leu Trp Asp Thr Ala Gly Gln Glu Asp Tyr Asn Arg Leu
 55                  60                  65                  70 aga cca ctg agc tat cgt gga gct gat gtt ttt ctt ctg gct ttc tca      655
Arg Pro Leu Ser Tyr Arg Gly Ala Asp Val Phe Leu Leu Ala Phe Ser
                 75                  80                  85 ctg atc agt aag gcc agc tat gag aat gtt tcg aag aag tgg ata cct      703
Leu Ile Ser Lys Ala Ser Tyr Glu Asn Val Ser Lys Lys Trp Ile Pro
             90                  95                 100 gaa ctg aag cat tat gca cct ggt gtg cca att att ctc gta ggg aca      751
Glu Leu Lys His Tyr Ala Pro Gly Val Pro Ile Ile Leu Val Gly Thr
         105                 110                 115 aag ctt gat ctt cga gac gac aag cag ttc ttt gtg gac cat cct ggt      799
Lys Leu Asp Leu Arg Asp Asp Lys Gln Phe Phe Val Asp His Pro Gly
     120                 125                 130 gct gtc cct atc act act gct cag gga gag gag cta aga aag caa ata      847
Ala Val Pro Ile Thr Thr Ala Gln Gly Glu Glu Leu Arg Lys Gln Ile
135                 140                 145                 150 ggc gct cca tac tac atc gaa tgc agc tcg aag acc caa cta aac gtg      895
Gly Ala Pro Tyr Tyr Ile Glu Cys Ser Ser Lys Thr Gln Leu Asn Val
                155                 160                 165 aag ggc gtc ttc gat gcg gcg ata aag gtt gtg ctg cag ccg cct aag      943
Lys Gly Val Phe Asp Ala Ala Ile Lys Val Val Leu Gln Pro Pro Lys
             170                 175                 180 gcg aag aag aag aaa aag gtg cag agg ggg gcg tgc tcc att ttg          988
Ala Lys Lys Lys Lys Lys Val Gln Arg Gly Ala Cys Ser Ile Leu
         185                 190                 195 tgatctaatc atcggtagat gaagaaacaa gggcgaaggt gccatggctt tatcatcgtc    1048
gcgtcttgct tcagtggaac agcatgaatg gtccccaccc cctctaggtt tactggcggc    1108
tcggctgcag cgagttctca tctctttgtc gaggcattga gcgatatgtt tgtttcattt    1168
tcctccttcc tgccttgtga ttatctggtg tgtgtgtgtg tgtgactgac gaagtcgcgg    1228
cgattaggta actcgcttag aaggtatttc ccgtgtttga gcaaaagaaa gtatccctgt    1288
tatctctgtt ccataagtta gacatgatgt aatcgtacta agtttatttt tacttatttc    1348
acttgaatgg aaaagtatgc ttcccattta aaaaaaaaa aaaaa                     1393
```

<210> SEQ ID NO 4

```
<211> LENGTH: 197
<212> TYPE: PRT
<213> ORGANISM: Zea mays

<400> SEQUENCE: 4

Met Ser Ala Ser Arg Phe Ile Lys Cys Val Thr Val Gly Asp Gly Ala
 1               5                  10                  15

Val Gly Lys Thr Cys Met Leu Ile Ser Tyr Thr Ser Asn Thr Phe Pro
            20                  25                  30

Thr Asp Tyr Val Pro Thr Val Phe Asp Asn Phe Ser Ala Asn Val Val
        35                  40                  45

Val Asp Gly Asn Thr Val Asn Leu Gly Leu Trp Asp Thr Ala Gly Gln
    50                  55                  60

Glu Asp Tyr Asn Arg Leu Arg Pro Leu Ser Tyr Arg Gly Ala Asp Val
65                  70                  75                  80

Phe Leu Leu Ala Phe Ser Leu Ile Ser Lys Ala Ser Tyr Glu Asn Val
                85                  90                  95

Ser Lys Lys Trp Ile Pro Glu Leu Lys His Tyr Ala Pro Gly Val Pro
            100                 105                 110

Ile Ile Leu Val Gly Thr Lys Leu Asp Leu Arg Asp Asp Lys Gln Phe
        115                 120                 125

Phe Val Asp His Pro Gly Ala Val Pro Ile Thr Thr Ala Gln Gly Glu
    130                 135                 140

Glu Leu Arg Lys Gln Ile Gly Ala Pro Tyr Tyr Ile Glu Cys Ser Ser
145                 150                 155                 160

Lys Thr Gln Leu Asn Val Lys Gly Val Phe Asp Ala Ala Ile Lys Val
                165                 170                 175

Val Leu Gln Pro Pro Lys Ala Lys Lys Lys Lys Val Gln Arg Gly
                180                 185                 190

Ala Cys Ser Ile Leu
            195

<210> SEQ ID NO 5
<211> LENGTH: 1045
<212> TYPE: DNA
<213> ORGANISM: Zea mays
<220> FEATURE:
<221> NAME/KEY: CDS
<222> LOCATION: (45)...(704)

<400> SEQUENCE: 5
gaattcggca cgagctggct cgtgcagcgg cggcagtgag agcg atg agc gcg gcg      56
                                              Met Ser Ala Ala
                                               1 gca gcg gcg gcg gcg agc tcg gtc acc aag ttc atc aag tgc gtc acg     104
Ala Ala Ala Ala Ala Ser Ser Val Thr Lys Phe Ile Lys Cys Val Thr
 5                  10                  15                  20 gtc ggc gat ggg gcc gtc ggg aag acc tgc atg ctc atc tgc tac acc     152
Val Gly Asp Gly Ala Val Gly Lys Thr Cys Met Leu Ile Cys Tyr Thr
                25                  30                  35 tgc aac aag ttc ccc acg gat tac atc ccc acc gta ttt gac aac ttc     200
Cys Asn Lys Phe Pro Thr Asp Tyr Ile Pro Thr Val Phe Asp Asn Phe
        40                  45                  50 agc gcc aat gtc tcc gtg ggt ggg agc atc gtc aac ttg ggc ctc tgg     248
Ser Ala Asn Val Ser Val Gly Gly Ser Ile Val Asn Leu Gly Leu Trp
    55                  60                  65 gac acg gca ggc cag gag gat tac agc agg ttg agg cct ctc agc tac     296
Asp Thr Ala Gly Gln Glu Asp Tyr Ser Arg Leu Arg Pro Leu Ser Tyr
70                  75                  80
```

```
agg ggt gct gat gtg ttc atc ctc tcc ttc tcc ctg gtc agc agg gcg    344
Arg Gly Ala Asp Val Phe Ile Leu Ser Phe Ser Leu Val Ser Arg Ala
 85                  90                  95                 100 agc tat gag aac gtc ctg aag aag tgg atg cca gag ctt cgc cga ttt    392
Ser Tyr Glu Asn Val Leu Lys Lys Trp Met Pro Glu Leu Arg Arg Phe
                105                 110                 115 tca cct act gtt cct gta gtt ctt gtt gga acc aaa cta gat ctc cgt    440
Ser Pro Thr Val Pro Val Val Leu Val Gly Thr Lys Leu Asp Leu Arg
            120                 125                 130 gaa gac aga tct tac ctt gct gac cat tct gct gct tcc atc atc tct    488
Glu Asp Arg Ser Tyr Leu Ala Asp His Ser Ala Ala Ser Ile Ile Ser
        135                 140                 145 act gaa cag gga gaa gag ctc agg aag cag ata ggt gct gtg gcg tac    536
Thr Glu Gln Gly Glu Glu Leu Arg Lys Gln Ile Gly Ala Val Ala Tyr
    150                 155                 160 ata gaa tgc agc tca aag aca cag agg aac gta aag gct gtg ttc gac    584
Ile Glu Cys Ser Ser Lys Thr Gln Arg Asn Val Lys Ala Val Phe Asp
165                 170                 175                 180 act gca att aaa gta gtg ctg caa cca ccg agg aga aga gaa gtt acc    632
Thr Ala Ile Lys Val Val Leu Gln Pro Pro Arg Arg Arg Glu Val Thr
                185                 190                 195 agg aag aaa atg aag aca agt tcg aat cag tct ctg aga aga tac ctc    680
Arg Lys Lys Met Lys Thr Ser Ser Asn Gln Ser Leu Arg Arg Tyr Leu
            200                 205                 210 tgt gga agc gga tgt ttc aca tcg taaagcacag actcttctgc gactgttgta   734
Cys Gly Ser Gly Cys Phe Thr Ser
        215                 220 ctggacttgc tagatggttg cagctctatg aatgagtagt cccctccgca gccactggga   794
acttctggtt ctctgctacc ttccgataga gtgctctttt gcgttcacca gctgagaaaa   854
atgaagcgag gttctagttt ataaattccc tacgaggtgt accttcttta gtatgaatgg   914
tgggctattt agcagttcag caaagtgtga agtgacccct ctatgcatgt tttgtttcca   974
aaaactgatg ttgctaaatg gctaatgaat ggttatggtc gcaccggaag aaaaaaaaaa   1034 aaaaaaaaa a                                                        1045

<210> SEQ ID NO 6
<211> LENGTH: 220
<212> TYPE: PRT
<213> ORGANISM: Zea mays

<400> SEQUENCE: 6

Met Ser Ala Ala Ala Ala Ala Ser Ser Val Thr Lys Phe Ile
 1               5                  10                  15

Lys Cys Val Thr Val Gly Asp Gly Ala Val Gly Lys Thr Cys Met Leu
                20                  25                  30

Ile Cys Tyr Thr Cys Asn Lys Phe Pro Thr Asp Tyr Ile Pro Thr Val
            35                  40                  45

Phe Asp Asn Phe Ser Ala Asn Val Ser Val Gly Gly Ser Ile Val Asn
        50                  55                  60

Leu Gly Leu Trp Asp Thr Ala Gly Gln Glu Asp Tyr Ser Arg Leu Arg
 65                 70                  75                  80

Pro Leu Ser Tyr Arg Gly Ala Asp Val Phe Ile Leu Ser Phe Ser Leu
                85                  90                  95

Val Ser Arg Ala Ser Tyr Glu Asn Val Leu Lys Lys Trp Met Pro Glu
            100                 105                 110

Leu Arg Arg Phe Ser Pro Thr Val Pro Val Val Leu Val Gly Thr Lys
```

-continued

```
            115                 120                 125
Leu Asp Leu Arg Glu Asp Arg Ser Tyr Leu Ala Asp His Ser Ala Ala
    130                 135                 140

Ser Ile Ile Ser Thr Glu Gln Gly Glu Leu Arg Lys Gln Ile Gly
145                 150                 155                 160

Ala Val Ala Tyr Ile Glu Cys Ser Ser Lys Thr Gln Arg Asn Val Lys
                165                 170                 175

Ala Val Phe Asp Thr Ala Ile Lys Val Val Leu Gln Pro Arg Arg
                180                 185                 190

Arg Glu Val Thr Arg Lys Lys Met Lys Thr Ser Ser Asn Gln Ser Leu
                195                 200                 205

Arg Arg Tyr Leu Cys Gly Ser Gly Cys Phe Thr Ser
    210                 215                 220

<210> SEQ ID NO 7
<211> LENGTH: 1058
<212> TYPE: DNA
<213> ORGANISM: Zea mays
<220> FEATURE:
<221> NAME/KEY: CDS
<222> LOCATION: (176)...(766)

<400> SEQUENCE: 7
gaattcggca cgagagctct caagacggcc gacggccggc ttgcctacct gctcccatcc      60
ttcccgaggg accgagaaag ataagaaagg cggtggtcaa cttgtgtcct gaggtgcccg     120
tagaagccca aggacaagaa acaaggagaa gagtagatct acatctactc caccg atg     178
                                                                Met
                                                                 1 agc gcg tct cgg ttc atc aag tgc gtc acc gtg ggg gac ggt gcc gtc      226
Ser Ala Ser Arg Phe Ile Lys Cys Val Thr Val Gly Asp Gly Ala Val
            5                  10                  15 gga aag acc tgc atg ctc atc tcc tac aca tcc aac act ttc ccc act      274
Gly Lys Thr Cys Met Leu Ile Ser Tyr Thr Ser Asn Thr Phe Pro Thr
        20                  25                  30 gac tat gtt cca act gtg ttc gac aac ttc agt gcc aat gtt gtg gtt      322
Asp Tyr Val Pro Thr Val Phe Asp Asn Phe Ser Ala Asn Val Val Val
    35                  40                  45 gac ggg agc act gtc aac ttg ggt ctg tgg gat aca gca gga caa gaa      370
Asp Gly Ser Thr Val Asn Leu Gly Leu Trp Asp Thr Ala Gly Gln Glu
50                  55                  60                  65 gat tac aat aga ctg cgt ccg ttg agc tat cgt ggt gct gat gtt ttt      418
Asp Tyr Asn Arg Leu Arg Pro Leu Ser Tyr Arg Gly Ala Asp Val Phe
                70                  75                  80 ctg ctc gcc ttt tct ctt atc agc aaa gca agc tat gag aat gtc tct      466
Leu Leu Ala Phe Ser Leu Ile Ser Lys Ala Ser Tyr Glu Asn Val Ser
            85                  90                  95 aag aag tgg gtt cct gaa tta agg cac tat gct cct ggc gtg ccc ata      514
Lys Lys Trp Val Pro Glu Leu Arg His Tyr Ala Pro Gly Val Pro Ile
        100                 105                 110 atc ctt gtt ggg aca aaa ctt gat ctg cgt gat gat aag cag ttt ttt      562
Ile Leu Val Gly Thr Lys Leu Asp Leu Arg Asp Asp Lys Gln Phe Phe
    115                 120                 125 gtt gat cac cct ggt gct gtt cca att tcc act gcc cag ggc gaa gag      610
Val Asp His Pro Gly Ala Val Pro Ile Ser Thr Ala Gln Gly Glu Glu
130                 135                 140                 145 ctg agg aag cta att ggt gct gcc gcc tac atc gaa tgc agt tca aaa      658
Leu Arg Lys Leu Ile Gly Ala Ala Ala Tyr Ile Glu Cys Ser Ser Lys
                150                 155                 160
```

```
atc cag cag aac ata aaa gca gtg ttt gac gca gca att aag gtg gtt    706
Ile Gln Gln Asn Ile Lys Ala Val Phe Asp Ala Ala Ile Lys Val Val
            165                 170                 175 ctc cag cca cca aag caa aag aag agg aag aag aag gtg cag aag gga    754
Leu Gln Pro Pro Lys Gln Lys Lys Arg Lys Lys Lys Val Gln Lys Gly
        180                 185                 190 tgc acc att ttg taactacaaa cggtagaggg caacagtctg gctgcggcgc        806
Cys Thr Ile Leu
    195 tgctgccaat gataaccatc gcctccttgc tgtataatat atcgcctgat catgccacca   866 gcatgcacaa gggagatggt ggttttagga tccttgtcct actgtgttgt gtagaccacc   926 gggtgtagtt gactgtatct ggttgtttgt atgtatggac aagacaaaac tagcactgca   986 gatggtatgg taaggcgtaa gcaaatacaa tatgacattg gtccagttcc aggaaaaaaa  1046 aaaaaaaaaa aa                                                     1058

<210> SEQ ID NO 8
<211> LENGTH: 197
<212> TYPE: PRT
<213> ORGANISM: Zea mays

<400> SEQUENCE: 8

Met Ser Ala Ser Arg Phe Ile Lys Cys Val Thr Val Gly Asp Gly Ala
 1               5                  10                  15

Val Gly Lys Thr Cys Met Leu Ile Ser Tyr Thr Ser Asn Thr Phe Pro
            20                  25                  30

Thr Asp Tyr Val Pro Thr Val Phe Asp Asn Phe Ser Ala Asn Val Val
        35                  40                  45

Val Asp Gly Ser Thr Val Asn Leu Gly Leu Trp Asp Thr Ala Gly Gln
    50                  55                  60

Glu Asp Tyr Asn Arg Leu Arg Pro Leu Ser Tyr Arg Gly Ala Asp Val
 65                  70                  75                  80

Phe Leu Leu Ala Phe Ser Leu Ile Ser Lys Ala Ser Tyr Glu Asn Val
                85                  90                  95

Ser Lys Lys Trp Val Pro Glu Leu Arg His Tyr Ala Pro Gly Val Pro
            100                 105                 110

Ile Ile Leu Val Gly Thr Lys Leu Asp Leu Arg Asp Asp Lys Gln Phe
        115                 120                 125

Phe Val Asp His Pro Gly Ala Val Pro Ile Ser Thr Ala Gln Gly Glu
    130                 135                 140

Glu Leu Arg Lys Leu Ile Gly Ala Ala Ala Tyr Ile Glu Cys Ser Ser
145                 150                 155                 160

Lys Ile Gln Gln Asn Ile Lys Ala Val Phe Asp Ala Ala Ile Lys Val
                165                 170                 175

Val Leu Gln Pro Pro Lys Gln Lys Lys Arg Lys Lys Lys Val Gln Lys
            180                 185                 190

Gly Cys Thr Ile Leu
        195

<210> SEQ ID NO 9
<211> LENGTH: 1059
<212> TYPE: DNA
<213> ORGANISM: Zea mays
<220> FEATURE:
<221> NAME/KEY: CDS
<222> LOCATION: (169)...(804)

<400> SEQUENCE: 9
```

-continued

```
tcgacccacg cgtccgggag aagataagca aggcaaggca accgttgtcg ttgtctctgt      60
ccctccgctt cctgctctct tgcttgctgc ttgccctcgg agcagtgcct tctgccgccg     120
ccgccgccgc cgcctgttgt gagaaggaga ggccggggct gggaggag atg agc gtg      177
                                                     Met Ser Val
                                                      1
```

| | | | | | | | | | | | | | | | |
|--|--|--|--|--|--|--|--|--|--|--|--|--|--|--|--|
| acc | aag | ttc | atc | aag | tgc | gtc | acg | gtg | ggg | gac | ggc | gcg | gtg | ggc | aag | 225 |
| Thr | Lys | Phe | Ile | Lys | Cys | Val | Thr | Val | Gly | Asp | Gly | Ala | Val | Gly | Lys | |
| | 5 | | | | 10 | | | | | 15 | | | | | | |

```
acc tgc atg ctc atc tgc tac acc agc aac aag ttc ccc acg gat tac      273
Thr Cys Met Leu Ile Cys Tyr Thr Ser Asn Lys Phe Pro Thr Asp Tyr
 20              25                  30                  35 atc ccc acg gtg ttc gac aac ttc agc gcc aac gtc tcc gtg gac ggc      321
Ile Pro Thr Val Phe Asp Asn Phe Ser Ala Asn Val Ser Val Asp Gly
                 40                  45                  50 agc atc gtc aac ctg ggc ctc tgg gac act gca gga caa gag gac tac      369
Ser Ile Val Asn Leu Gly Leu Trp Asp Thr Ala Gly Gln Glu Asp Tyr
             55                  60                  65 agc aga ttg cgg cca ctg agc tac agg ggc gcg gac gtg ttc gtg ctg      417
Ser Arg Leu Arg Pro Leu Ser Tyr Arg Gly Ala Asp Val Phe Val Leu
         70                  75                  80 gcc ttc tcc ttg atc agc agg gcg agc tat gag aac gtc ctt aag aag      465
Ala Phe Ser Leu Ile Ser Arg Ala Ser Tyr Glu Asn Val Leu Lys Lys
 85                  90                  95 tgg gtg cca gag ctt cgc aga ttc gcg ccc gac gtc ccg gtc gtt ctt      513
Trp Val Pro Glu Leu Arg Arg Phe Ala Pro Asp Val Pro Val Val Leu
100                 105                 110                 115 gtc ggg acc aag tta gat ctc cgt gac cac agg gcc tac ctt gct gac      561
Val Gly Thr Lys Leu Asp Leu Arg Asp His Arg Ala Tyr Leu Ala Asp
                120                 125                 130 cat cct gga gcg tcg acg atc acg acg gca cag ggc gaa gaa ctg agg      609
His Pro Gly Ala Ser Thr Ile Thr Thr Ala Gln Gly Glu Glu Leu Arg
            135                 140                 145 agg cag atc ggc gct gcg gct tac atc gag tgc agt tcc aaa acg cag      657
Arg Gln Ile Gly Ala Ala Ala Tyr Ile Glu Cys Ser Ser Lys Thr Gln
        150                 155                 160 cag aat gtc aag tcg gtc ttc gac aca gcc atc aaa gtg gtc ctt cag      705
Gln Asn Val Lys Ser Val Phe Asp Thr Ala Ile Lys Val Val Leu Gln
165                 170                 175 ccc ccg cgg agg agg gag gcg acg cct gcc agg agg aag aac agg cgt      753
Pro Pro Arg Arg Arg Glu Ala Thr Pro Ala Arg Arg Lys Asn Arg Arg
180                 185                 190                 195 ggc tcc ggg tgc tct atc atg aac ctc atg tgt ggc agc acg tgc gct      801
Gly Ser Gly Cys Ser Ile Met Asn Leu Met Cys Gly Ser Thr Cys Ala
                200                 205                 210 gct taggagtcta gaacactgat ctggaaggag gtgaaggtga aggcatggtg           854
Ala tctatgtgct atggcgactg gcaagttaat ggggccgcat ggatgactgc tgctcttgtt     914 ttttaagct cgtctgccgt atgctttgtt tttttaggct tcaaggactg acaattgcaa     974
gaatgcagtg tttatgtaag aggttgtttg ctggaatagg attgctgtaa ctgtaatgtt    1034
gttctccgaa aaaaaaaaaa aaaaa                                          1059
```

<210> SEQ ID NO 10
<211> LENGTH: 212
<212> TYPE: PRT
<213> ORGANISM: Zea mays

<400> SEQUENCE: 10

```
Met Ser Val Thr Lys Phe Ile Lys Cys Val Thr Val Gly Asp Gly Ala
 1               5                  10                  15

Val Gly Lys Thr Cys Met Leu Ile Cys Tyr Thr Ser Asn Lys Phe Pro
             20                  25                  30

Thr Asp Tyr Ile Pro Thr Val Phe Asp Asn Phe Ser Ala Asn Val Ser
             35                  40                  45

Val Asp Gly Ser Ile Val Asn Leu Gly Leu Trp Asp Thr Ala Gly Gln
         50                  55                  60

Glu Asp Tyr Ser Arg Leu Arg Pro Leu Ser Tyr Arg Gly Ala Asp Val
 65              70                  75                  80

Phe Val Leu Ala Phe Ser Leu Ile Ser Arg Ala Ser Tyr Glu Asn Val
                 85                  90                  95

Leu Lys Lys Trp Val Pro Glu Leu Arg Arg Phe Ala Pro Asp Val Pro
                100                 105                 110

Val Val Leu Val Gly Thr Lys Leu Asp Leu Arg Asp His Arg Ala Tyr
            115                 120                 125

Leu Ala Asp His Pro Gly Ala Ser Thr Ile Thr Thr Ala Gln Gly Glu
        130                 135                 140

Glu Leu Arg Arg Gln Ile Gly Ala Ala Ala Tyr Ile Glu Cys Ser Ser
145                 150                 155                 160

Lys Thr Gln Gln Asn Val Lys Ser Val Phe Asp Thr Ala Ile Lys Val
                165                 170                 175

Val Leu Gln Pro Pro Arg Arg Arg Glu Ala Thr Pro Ala Arg Arg Lys
                180                 185                 190

Asn Arg Arg Gly Ser Gly Cys Ser Ile Met Asn Leu Met Cys Gly Ser
                195                 200                 205

Thr Cys Ala Ala
    210

<210> SEQ ID NO 11
<211> LENGTH: 17
<212> TYPE: PRT
<213> ORGANISM: Zea mays

<400> SEQUENCE: 11

Ser Arg Lys Gly Cys Ser Met Met Asn Ile Phe Gly Gly Arg Lys Met
 1               5                  10                  15

Leu

<210> SEQ ID NO 12
<211> LENGTH: 16
<212> TYPE: PRT
<213> ORGANISM: Zea mays

<400> SEQUENCE: 12

Lys Ala Lys Lys Lys Lys Val Gln Arg Gly Ala Cys Ser Ile Leu
 1               5                  10                  15

<210> SEQ ID NO 13
<211> LENGTH: 18
<212> TYPE: PRT
<213> ORGANISM: Zea mays

<400> SEQUENCE: 13

Met Lys Thr Ser Ser Asn Gln Ser Leu Arg Arg Tyr Leu Cys Gly Ser
 1               5                  10                  15

Gly Cys
```

<210> SEQ ID NO 14
<211> LENGTH: 16
<212> TYPE: PRT
<213> ORGANISM: Zea mays

<400> SEQUENCE: 14

```
Lys Gln Lys Lys Arg Lys Lys Val Gln Lys Gly Cys Thr Ile Leu
 1               5                  10                  15
```

<210> SEQ ID NO 15
<211> LENGTH: 1127
<212> TYPE: DNA
<213> ORGANISM: Zea mays
<220> FEATURE:
<221> NAME/KEY: CDS
<222> LOCATION: (190)...(831)

<400> SEQUENCE: 15

```
gtcgacccac gcgtccgccc agaagtcacg caccaaacac caccaccaaa gaaggcgaga      60
acgtactccg tccctccccct ccctcccct cccttcccc tcgaggctcc aggaccgtct     120
cctcgcctgc tcatccgccg ctgcttccct tctctgggct cggagaaccg gagagaagcg    180 cgcgcggcc atg gcg tcc agc gcc tct cgg ttc atc aag tgc gtc acg gtc    231
          Met Ala Ser Ser Ala Ser Arg Phe Ile Lys Cys Val Thr Val
            1               5                  10 ggc gac gtg gcc gtg ggc aag aca tgt atg ctc atc tgc tac acc agc      279
Gly Asp Val Ala Val Gly Lys Thr Cys Met Leu Ile Cys Tyr Thr Ser
 15              20                  25                  30 aac aag ttc ccc act gac tac ata cct acg gtg ttc gac aat ttc agt      327
Asn Lys Phe Pro Thr Asp Tyr Ile Pro Thr Val Phe Asp Asn Phe Ser
                 35                  40                  45 gca aat gta gtt gtg gat ggc acc act gtg aat ttg ggc ctt tgg gat      375
Ala Asn Val Val Val Asp Gly Thr Thr Val Asn Leu Gly Leu Trp Asp
             50                  55                  60 acc gct ggg cag gaa gat tac aac cgc ctg agg cct cta agc tac cga      423
Thr Ala Gly Gln Glu Asp Tyr Asn Arg Leu Arg Pro Leu Ser Tyr Arg
 65                  70                  75 ggt gca gat gtt ttc gtg ctt gca ttc tca ctt gtg agc cga gct agc      471
Gly Ala Asp Val Phe Val Leu Ala Phe Ser Leu Val Ser Arg Ala Ser
     80                  85                  90 tat gag aat atc atg aag aag tgg ata cca gag ctt caa cat tat gca      519
Tyr Glu Asn Ile Met Lys Lys Trp Ile Pro Glu Leu Gln His Tyr Ala
 95                 100                 105                 110 cct ggg gtg ccc gtt gtt ttg gca ggc aca aaa ttg gat ctt cgt gaa      567
Pro Gly Val Pro Val Val Leu Ala Gly Thr Lys Leu Asp Leu Arg Glu
                115                 120                 125 gac aag cac tac ttg atg gac cat cct gga ttg gtg cct gtt acc act      615
Asp Lys His Tyr Leu Met Asp His Pro Gly Leu Val Pro Val Thr Thr
            130                 135                 140 gca cag ggg gag gaa ctt cgt aga caa att ggt gct atg tat tac att      663
Ala Gln Gly Glu Glu Leu Arg Arg Gln Ile Gly Ala Met Tyr Tyr Ile
145                 150                 155 gaa tgc agc tca aag aca cag cag aat gtc aaa gct gtg ttc gat gct      711
Glu Cys Ser Ser Lys Thr Gln Gln Asn Val Lys Ala Val Phe Asp Ala
    160                 165                 170 gcc atc aag gta gta atc cag cct cca act aaa ata aga gaa aag aag      759
Ala Ile Lys Val Val Ile Gln Pro Pro Thr Lys Ile Arg Glu Lys Lys
175                 180                 185                 190 aag aaa aaa tca cgc aaa gga tgt tct atg atg aac atc ttc ggt gga      807
Lys Lys Lys Ser Arg Lys Gly Cys Ser Met Met Asn Ile Phe Gly Gly
```

```
aga aaa atg cta tgc ttc aag tcc tgaatggttc aaggggtct tacatggact       861
Arg Lys Met Leu Cys Phe Lys Ser
            210 gataccacga gtgtgacccc gagtttgcga agcttgaaat cttgatgtgc tcgttgcgca       921 tgtgtatatt tgcacctttg gttattaatg actagaggta ggtaattgaa actagtctgc       981 ttaagcgttc tgcactgctg gtgtggttag ctctatgagt taagcagttc gacagaggcc      1041 aaaccgacag tgagattttg ttctttcatg gaaatgtgcc aatgtcacag ctttttcgtg      1101 aaaaaaaaaa aaaaaaaaaa aaaaa                                            1127

<210> SEQ ID NO 16
<211> LENGTH: 214
<212> TYPE: PRT
<213> ORGANISM: Zea mays

<400> SEQUENCE: 16

Met Ala Ser Ser Ala Ser Arg Phe Ile Lys Cys Val Thr Val Gly Asp
 1               5                  10                  15

Val Ala Val Gly Lys Thr Cys Met Leu Ile Cys Tyr Thr Ser Asn Lys
                20                  25                  30

Phe Pro Thr Asp Tyr Ile Pro Thr Val Phe Asp Asn Phe Ser Ala Asn
            35                  40                  45

Val Val Asp Gly Thr Thr Val Asn Leu Gly Leu Trp Asp Thr Ala
        50                  55                  60

Gly Gln Glu Asp Tyr Asn Arg Leu Arg Pro Leu Ser Tyr Arg Gly Ala
65                  70                  75                  80

Asp Val Phe Val Leu Ala Phe Ser Leu Val Ser Arg Ala Ser Tyr Glu
                85                  90                  95

Asn Ile Met Lys Lys Trp Ile Pro Glu Leu Gln His Tyr Ala Pro Gly
            100                 105                 110

Val Pro Val Leu Ala Gly Thr Lys Leu Asp Leu Arg Glu Asp Lys
        115                 120                 125

His Tyr Leu Met Asp His Pro Gly Leu Val Pro Val Thr Thr Ala Gln
    130                 135                 140

Gly Glu Glu Leu Arg Arg Gln Ile Gly Ala Met Tyr Tyr Ile Glu Cys
145                 150                 155                 160

Ser Ser Lys Thr Gln Gln Asn Val Lys Ala Val Phe Asp Ala Ala Ile
                165                 170                 175

Lys Val Val Ile Gln Pro Pro Thr Lys Ile Arg Glu Lys Lys Lys Lys
            180                 185                 190

Lys Ser Arg Lys Gly Cys Ser Met Met Asn Ile Phe Gly Gly Arg Lys
        195                 200                 205

Met Leu Cys Phe Lys Ser
    210

<210> SEQ ID NO 17
<211> LENGTH: 1393
<212> TYPE: DNA
<213> ORGANISM: Zea mays
<220> FEATURE:
<221> NAME/KEY: CDS
<222> LOCATION: (398)...(988)

<400> SEQUENCE: 17
gtcgacccac gcgtccgcgg acgcgtgggc ggacgcgtgg gtccccaccc accaccgcgc        60
```

-continued

```
cgggccacca ccacccactc taccctcccc tccccaccac cactagcacc caccgtcccg    120
gcgcggagac cgcttccctc cctccgcctc cgcaaccctc tcccgcctcg cccgcgcctc    180
cctccatttg tccgcggctc ccctccctcc cgatcttaac cacccgccac ccggcttcct    240
ctccccctc ttcctccctc aaaccagacg ctcgcccccc tttcctccac gcctatcttc    300
ttcagacgac cagcaggagg tacgaggaag accacctagg aggcctctct ctctctctcc    360
ccagccaccc ccgtagcgag agggagggcg gaagagg atg agc gcg tcc agg ttc    415
                                        Met Ser Ala Ser Arg Phe
                                         1               5
ata aag tgc gtc acg gtc ggg gac gtc gcc gtc ggc aag acc tgc atg      463
Ile Lys Cys Val Thr Val Gly Asp Val Ala Val Gly Lys Thr Cys Met
            10                  15                  20
ctc atc tcc tac acc tcc aac acc ttc ccc acc gac tat gtt ccg aca      511
Leu Ile Ser Tyr Thr Ser Asn Thr Phe Pro Thr Asp Tyr Val Pro Thr
        25                  30                  35
gtg ttt gat aac ttc agt gcc aac gtt gtg gtt gat ggt aat act gtc      559
Val Phe Asp Asn Phe Ser Ala Asn Val Val Val Asp Gly Asn Thr Val
    40                  45                  50
aac ctc ggc ctc tgg gac act gca ggt caa gag gat tac aac aga ctg      607
Asn Leu Gly Leu Trp Asp Thr Ala Gly Gln Glu Asp Tyr Asn Arg Leu
 55                  60                  65                  70
aga cca ctg agc tat cgt gga gct gat gtt ttt ctt ctg gct ttc tca      655
Arg Pro Leu Ser Tyr Arg Gly Ala Asp Val Phe Leu Leu Ala Phe Ser
                75                  80                  85
ctg atc agt aag gcc agc tat gag aat gtt tcg aag aag tgg ata cct      703
Leu Ile Ser Lys Ala Ser Tyr Glu Asn Val Ser Lys Lys Trp Ile Pro
            90                  95                 100
gaa ctg aag cat tat gca cct ggt gtg cca att att ctc gta ggg aca      751
Glu Leu Lys His Tyr Ala Pro Gly Val Pro Ile Ile Leu Val Gly Thr
        105                 110                 115
aag ctt gat ctt cga gac gac aag cag ttc ttt gtg gac cat cct ggt      799
Lys Leu Asp Leu Arg Asp Asp Lys Gln Phe Phe Val Asp His Pro Gly
    120                 125                 130
gct gtc cct atc act act gct cag gga gag gag cta aga aag caa ata      847
Ala Val Pro Ile Thr Thr Ala Gln Gly Glu Glu Leu Arg Lys Gln Ile
135                 140                 145                 150
ggc gct cca tac tac atc gaa tgc agc tcg aag acc caa cta aac gtg      895
Gly Ala Pro Tyr Tyr Ile Glu Cys Ser Ser Lys Thr Gln Leu Asn Val
                155                 160                 165
aag ggc gtc ttc gat gcg gcg ata aag gtt gtg ctg cag ccg cct aag      943
Lys Gly Val Phe Asp Ala Ala Ile Lys Val Val Leu Gln Pro Pro Lys
            170                 175                 180
gcg aag aag aag aaa aag gtg cag agg ggg gcg tgc tcc att ttg          988
Ala Lys Lys Lys Lys Lys Val Gln Arg Gly Ala Cys Ser Ile Leu
        185                 190                 195
tgatctaatc atcggtagat gaagaaacaa gggcgaaggt gccatggctt tatcatcgtc   1048
gcgtcttgct tcagtggaac agcatgaatg gtccccaccc cctctaggtt tactggcggc   1108
tcggctgcag cgagttctca tctctttgtc gaggcattga gcgatatgtt tgtttcattt   1168
tcctccttcc tgccttgtga ttatctggtg tgtgtgtgtg tgtgactgac gaagtcgcgg   1228
cgattaggta actcgcttag aaggtatttc ccgtgtttga gcaaaagaaa gtatccctgt   1288
tatctctgtt ccataagtta gacatgatgt aatcgtacta agtttatttt tacttatttc   1348
acttgaatgg aaaagtatgc ttcccattta aaaaaaaaaa aaaaa                   1393
```

<210> SEQ ID NO 18
<211> LENGTH: 197

-continued

```
<212> TYPE: PRT
<213> ORGANISM: Zea mays

<400> SEQUENCE: 18

Met Ser Ala Ser Arg Phe Ile Lys Cys Val Thr Val Gly Asp Val Ala
 1               5                  10                  15

Val Gly Lys Thr Cys Met Leu Ile Ser Tyr Thr Ser Asn Thr Phe Pro
            20                  25                  30

Thr Asp Tyr Val Pro Thr Val Phe Asp Asn Phe Ser Ala Asn Val Val
        35                  40                  45

Val Asp Gly Asn Thr Val Asn Leu Gly Leu Trp Asp Thr Ala Gly Gln
    50                  55                  60

Glu Asp Tyr Asn Arg Leu Arg Pro Leu Ser Tyr Arg Gly Ala Asp Val
65                  70                  75                  80

Phe Leu Leu Ala Phe Ser Leu Ile Ser Lys Ala Ser Tyr Glu Asn Val
                85                  90                  95

Ser Lys Lys Trp Ile Pro Glu Leu Lys His Tyr Ala Pro Gly Val Pro
            100                 105                 110

Ile Ile Leu Val Gly Thr Lys Leu Asp Leu Arg Asp Asp Lys Gln Phe
        115                 120                 125

Phe Val Asp His Pro Gly Ala Val Pro Ile Thr Thr Ala Gln Gly Glu
    130                 135                 140

Glu Leu Arg Lys Gln Ile Gly Ala Pro Tyr Tyr Ile Glu Cys Ser Ser
145                 150                 155                 160

Lys Thr Gln Leu Asn Val Lys Gly Val Phe Asp Ala Ala Ile Lys Val
                165                 170                 175

Val Leu Gln Pro Pro Lys Ala Lys Lys Lys Lys Val Gln Arg Gly
            180                 185                 190

Ala Cys Ser Ile Leu
        195

<210> SEQ ID NO 19
<211> LENGTH: 1045
<212> TYPE: DNA
<213> ORGANISM: Zea mays
<220> FEATURE:
<221> NAME/KEY: CDS
<222> LOCATION: (45)...(704)

<400> SEQUENCE: 19
gaattcggca cgagctggct cgtgcagcgg cggcagtgag agcg atg agc gcg gcg    56
                                              Met Ser Ala Ala
                                               1 gca gcg gcg gcg gcg agc tcg gtc acc aag ttc atc aag tgc gtc acg    104
Ala Ala Ala Ala Ala Ser Ser Val Thr Lys Phe Ile Lys Cys Val Thr
 5                  10                  15                  20 gtc ggc gat gtg gcc gtc ggg aag acc tgc atg ctc atc tgc tac acc    152
Val Gly Asp Val Ala Val Gly Lys Thr Cys Met Leu Ile Cys Tyr Thr
                25                  30                  35 tgc aac aag ttc ccc acg gat tac atc ccc acc gta ttt gac aac ttc    200
Cys Asn Lys Phe Pro Thr Asp Tyr Ile Pro Thr Val Phe Asp Asn Phe
            40                  45                  50 agc gcc aat gtc tcc gtg ggt ggg agc atc gtc aac ttg ggc ctc tgg    248
Ser Ala Asn Val Ser Val Gly Gly Ser Ile Val Asn Leu Gly Leu Trp
        55                  60                  65 gac acg gca ggc cag gag gat tac agc agg ttg agg cct ctc agc tac    296
Asp Thr Ala Gly Gln Glu Asp Tyr Ser Arg Leu Arg Pro Leu Ser Tyr
    70                  75                  80
```

-continued

```
agg ggt gct gat gtg ttc atc ctc tcc ttc tcc ctg gtc agc agg gcg      344
Arg Gly Ala Asp Val Phe Ile Leu Ser Phe Ser Leu Val Ser Arg Ala
 85                  90                  95                 100 agc tat gag aac gtc ctg aag aag tgg atg cca gag ctt cgc cga ttt      392
Ser Tyr Glu Asn Val Leu Lys Lys Trp Met Pro Glu Leu Arg Arg Phe
                105                 110                 115 tca cct act gtt cct gta gtt ctt gtt gga acc aaa cta gat ctc cgt      440
Ser Pro Thr Val Pro Val Val Leu Val Gly Thr Lys Leu Asp Leu Arg
            120                 125                 130 gaa gac aga tct tac ctt gct gac cat tct gct gct tcc atc atc tct      488
Glu Asp Arg Ser Tyr Leu Ala Asp His Ser Ala Ala Ser Ile Ile Ser
        135                 140                 145 act gaa cag gga gaa gag ctc agg aag cag ata ggt gct gtg gcg tac      536
Thr Glu Gln Gly Glu Glu Leu Arg Lys Gln Ile Gly Ala Val Ala Tyr
    150                 155                 160 ata gaa tgc agc tca aag aca cag agg aac gta aag gct gtg ttc gac      584
Ile Glu Cys Ser Ser Lys Thr Gln Arg Asn Val Lys Ala Val Phe Asp
165                 170                 175                 180 act gca att aaa gta gtg ctg caa cca ccg agg aga aga gaa gtt acc      632
Thr Ala Ile Lys Val Val Leu Gln Pro Pro Arg Arg Arg Glu Val Thr
                185                 190                 195 agg aag aaa atg aag aca agt tcg aat cag tct ctg aga aga tac ctc      680
Arg Lys Lys Met Lys Thr Ser Ser Asn Gln Ser Leu Arg Arg Tyr Leu
            200                 205                 210 tgt gga agc gga tgt ttc aca tcg taaagcacag actcttctgc gactgttgta    734
Cys Gly Ser Gly Cys Phe Thr Ser
        215                 220 ctggacttgc tagatggttg cagctctatg aatgagtagt cccctccgca gccactggga    794
acttctggtt ctctgctacc ttccgataga gtgctctttt gcgttcacca gctgagaaaa    854
atgaagcgag gttctagttt ataaattccc tacgaggtgt accttcttta gtatgaatgg    914
tgggctattt agcagttcag caaagtgtga agtgacccct ctatgcatgt tttgtttcca    974
aaaactgatg ttgctaaatg gctaatgaat ggttatggtc gcaccggaag aaaaaaaaaa   1034
aaaaaaaaaa a                                                        1045
```

<210> SEQ ID NO 20
<211> LENGTH: 220
<212> TYPE: PRT
<213> ORGANISM: Zea mays

<400> SEQUENCE: 20

```
Met Ser Ala Ala Ala Ala Ala Ala Ser Ser Val Thr Lys Phe Ile
 1               5                  10                  15

Lys Cys Val Thr Val Gly Asp Val Ala Val Gly Lys Thr Cys Met Leu
                20                  25                  30

Ile Cys Tyr Thr Cys Asn Lys Phe Pro Thr Asp Tyr Ile Pro Thr Val
            35                  40                  45

Phe Asp Asn Phe Ser Ala Asn Val Ser Val Gly Gly Ser Ile Val Asn
        50                  55                  60

Leu Gly Leu Trp Asp Thr Ala Gly Gln Glu Asp Tyr Ser Arg Leu Arg
65                  70                  75                  80

Pro Leu Ser Tyr Arg Gly Ala Asp Val Phe Ile Leu Ser Phe Ser Leu
                85                  90                  95

Val Ser Arg Ala Ser Tyr Glu Asn Val Leu Lys Lys Trp Met Pro Glu
            100                 105                 110

Leu Arg Arg Phe Ser Pro Thr Val Pro Val Val Leu Val Gly Thr Lys
        115                 120                 125
```

```
Leu Asp Leu Arg Glu Asp Arg Ser Tyr Leu Ala Asp His Ser Ala Ala
    130                 135                 140

Ser Ile Ile Ser Thr Glu Gln Gly Glu Leu Arg Lys Gln Ile Gly
145                 150                 155                 160

Ala Val Ala Tyr Ile Glu Cys Ser Ser Lys Thr Gln Arg Asn Val Lys
                165                 170                 175

Ala Val Phe Asp Thr Ala Ile Lys Val Val Leu Gln Pro Arg Arg
            180                 185                 190

Arg Glu Val Thr Arg Lys Lys Met Lys Thr Ser Ser Asn Gln Ser Leu
            195                 200                 205

Arg Arg Tyr Leu Cys Gly Ser Gly Cys Phe Thr Ser
    210                 215                 220

<210> SEQ ID NO 21
<211> LENGTH: 1058
<212> TYPE: DNA
<213> ORGANISM: Zea mays
<220> FEATURE:
<221> NAME/KEY: CDS
<222> LOCATION: (176)...(766)

<400> SEQUENCE: 21
gaattcggca cgagagctct caagacggcc gacggccggc ttgcctacct gctcccatcc      60
ttcccgaggg accgagaaag ataagaaagg cggtggtcaa cttgtgtcct gaggtgcccg     120
tagaagccca aggacaagaa acaaggagaa gagtagatct acatctactc caccg atg     178
                                                                Met
                                                                  1 agc gcg tct cgg ttc atc aag tgc gtc acc gtg ggg gac gtg gcc gtc     226
Ser Ala Ser Arg Phe Ile Lys Cys Val Thr Val Gly Asp Val Ala Val
          5                  10                  15 gga aag acc tgc atg ctc atc tcc tac aca tcc aac act ttc ccc act     274
Gly Lys Thr Cys Met Leu Ile Ser Tyr Thr Ser Asn Thr Phe Pro Thr
         20                  25                  30 gac tat gtt cca act gtg ttc gac aac ttc agt gcc aat gtt gtg gtt     322
Asp Tyr Val Pro Thr Val Phe Asp Asn Phe Ser Ala Asn Val Val Val
     35                  40                  45 gac ggg agc act gtc aac ttg ggt ctg tgg gat aca gca gga caa gaa     370
Asp Gly Ser Thr Val Asn Leu Gly Leu Trp Asp Thr Ala Gly Gln Glu
 50                  55                  60                  65 gat tac aat aga ctg cgt ccg ttg agc tat cgt ggt gct gat gtt ttt     418
Asp Tyr Asn Arg Leu Arg Pro Leu Ser Tyr Arg Gly Ala Asp Val Phe
                 70                  75                  80 ctg ctc gcc ttt tct ctt atc agc aaa gca agc tat gag aat gtc tct     466
Leu Leu Ala Phe Ser Leu Ile Ser Lys Ala Ser Tyr Glu Asn Val Ser
             85                  90                  95 aag aag tgg gtt cct gaa tta agg cac tat gct cct ggc gtg ccc ata     514
Lys Lys Trp Val Pro Glu Leu Arg His Tyr Ala Pro Gly Val Pro Ile
        100                 105                 110 atc ctt gtt ggg aca aaa ctt gat ctg cgt gat gat aag cag ttt ttt     562
Ile Leu Val Gly Thr Lys Leu Asp Leu Arg Asp Asp Lys Gln Phe Phe
    115                 120                 125 gtt gat cac cct ggt gct gtt cca att tcc act gcc cag ggc gaa gag     610
Val Asp His Pro Gly Ala Val Pro Ile Ser Thr Ala Gln Gly Glu Glu
130                 135                 140                 145 ctg agg aag cta att ggt gct gcc gcc tac atc gaa tgc agt tca aaa     658
Leu Arg Lys Leu Ile Gly Ala Ala Ala Tyr Ile Glu Cys Ser Ser Lys
                150                 155                 160 atc cag cag aac ata aaa gca gtg ttt gac gca gca att aag gtg gtt     706
```

```
Ile Gln Gln Asn Ile Lys Ala Val Phe Asp Ala Ala Ile Lys Val Val
            165                 170                 175 ctc cag cca cca aag caa aag agg aag aag aag gtg cag aag gga        754
Leu Gln Pro Pro Lys Gln Lys Lys Arg Lys Lys Lys Val Gln Lys Gly
        180                 185                 190 tgc acc att ttg taactacaaa cggtagaggg caacagtctg gctgcggcgc        806
Cys Thr Ile Leu
    195 tgctgccaat gataaccatc gcctccttgc tgtataatat atcgcctgat catgccacca   866 gcatgcacaa gggagatggt ggttttagga tccttgtcct actgtgttgt gtagaccacc   926 gggtgtagtt gactgtatct ggttgtttgt atgtatggac aagacaaaac tagcactgca   986 gatggtatgg taaggcgtaa gcaaatacaa tatgacattg gtccagttcc aggaaaaaaa   1046 aaaaaaaaaa aa                                                      1058

<210> SEQ ID NO 22
<211> LENGTH: 197
<212> TYPE: PRT
<213> ORGANISM: Zea mays

<400> SEQUENCE: 22

Met Ser Ala Ser Arg Phe Ile Lys Cys Val Thr Val Gly Asp Val Ala
1               5                   10                  15

Val Gly Lys Thr Cys Met Leu Ile Ser Tyr Thr Ser Asn Thr Phe Pro
            20                  25                  30

Thr Asp Tyr Val Pro Thr Val Phe Asp Asn Phe Ser Ala Asn Val Val
        35                  40                  45

Val Asp Gly Ser Thr Val Asn Leu Gly Leu Trp Asp Thr Ala Gly Gln
    50                  55                  60

Glu Asp Tyr Asn Arg Leu Arg Pro Leu Ser Tyr Arg Gly Ala Asp Val
65                  70                  75                  80

Phe Leu Leu Ala Phe Ser Leu Ile Ser Lys Ala Ser Tyr Glu Asn Val
                85                  90                  95

Ser Lys Lys Trp Val Pro Glu Leu Arg His Tyr Ala Pro Gly Val Pro
            100                 105                 110

Ile Ile Leu Val Gly Thr Lys Leu Asp Leu Arg Asp Asp Lys Gln Phe
        115                 120                 125

Phe Val Asp His Pro Gly Ala Val Pro Ile Ser Thr Ala Gln Gly Glu
    130                 135                 140

Glu Leu Arg Lys Leu Ile Gly Ala Ala Ala Tyr Ile Glu Cys Ser Ser
145                 150                 155                 160

Lys Ile Gln Gln Asn Ile Lys Ala Val Phe Asp Ala Ala Ile Lys Val
                165                 170                 175

Val Leu Gln Pro Pro Lys Gln Lys Lys Arg Lys Lys Lys Val Gln Lys
            180                 185                 190

Gly Cys Thr Ile Leu
        195

<210> SEQ ID NO 23
<211> LENGTH: 1062
<212> TYPE: DNA
<213> ORGANISM: Zea mays
<220> FEATURE:
<221> NAME/KEY: CDS
<222> LOCATION: (172)...(807)

<400> SEQUENCE: 23
```

```
gggtcgaccc acgcgtccgg gagaagataa gcaaggcaag gcaaccgttg tcgttgtctc      60
tgtccctccg cttcctgctc tcttgcttgc tgcttgccct cggagcagtg ccttctgccg     120
ccgccgccgc cgccgcctgt tgtgagaagg agaggccggg gctgggagga g atg agc     177
                                                        Met Ser
                                                          1 gtg acc aag ttc atc aag tgc gtc acg gtg ggg gac gtg gcg gtg ggc      225
Val Thr Lys Phe Ile Lys Cys Val Thr Val Gly Asp Val Ala Val Gly
      5              10                  15 aag acc tgc atg ctc atc tgc tac acc agc aac aag ttc ccc acg gat      273
Lys Thr Cys Met Leu Ile Cys Tyr Thr Ser Asn Lys Phe Pro Thr Asp
 20                  25                  30 tac atc ccc acg gtg ttc gac aac ttc agc gcc aac gtc tcc gtg gac      321
Tyr Ile Pro Thr Val Phe Asp Asn Phe Ser Ala Asn Val Ser Val Asp
 35                  40                  45                  50 ggc agc atc gtc aac ctg ggc ctt tgg gac act gca gga caa gag gac      369
Gly Ser Ile Val Asn Leu Gly Leu Trp Asp Thr Ala Gly Gln Glu Asp
              55                  60                  65 tac agc aga ttg cgg cca ctg agc tac agg ggc gcg gac gtg ttc gtg      417
Tyr Ser Arg Leu Arg Pro Leu Ser Tyr Arg Gly Ala Asp Val Phe Val
          70                  75                  80 ctg gcc ttc tcc ttg atc agc agg gcg agc tat gag aac gtc ctt aag      465
Leu Ala Phe Ser Leu Ile Ser Arg Ala Ser Tyr Glu Asn Val Leu Lys
              85                  90                  95 aag tgg gtg cca gag ctt cgc aga ttc gcg ccc gac gtc ccg gtc gtt      513
Lys Trp Val Pro Glu Leu Arg Arg Phe Ala Pro Asp Val Pro Val Val
100                 105                 110 ctt gtc ggg acc aag tta gat ctc cgt gac cac agg gcc tac ctt gct      561
Leu Val Gly Thr Lys Leu Asp Leu Arg Asp His Arg Ala Tyr Leu Ala
115                 120                 125                 130 gac cat cct gga gcg tcg acg atc acg acg gca cag ggc gaa gaa ctg      609
Asp His Pro Gly Ala Ser Thr Ile Thr Thr Ala Gln Gly Glu Glu Leu
                135                 140                 145 agg agg cag atc ggc gct gcg gct tac atc gag tgc agt tcc aaa acg      657
Arg Arg Gln Ile Gly Ala Ala Ala Tyr Ile Glu Cys Ser Ser Lys Thr
150                 155                 160 cag cag aat gtc aag tcg gtc ttc gac aca gcc atc aaa gtg gtc ctt      705
Gln Gln Asn Val Lys Ser Val Phe Asp Thr Ala Ile Lys Val Val Leu
            165                 170                 175 cag ccc ccg cgg agg agg gag gcg acg cct gcc agg agg aag aac agg      753
Gln Pro Pro Arg Arg Arg Glu Ala Thr Pro Ala Arg Arg Lys Asn Arg
180                 185                 190 cgt ggc tcc ggg tgc tct atc atg aac ctc atg tgt ggc agc acg tgc      801
Arg Gly Ser Gly Cys Ser Ile Met Asn Leu Met Cys Gly Ser Thr Cys
195                 200                 205                 210 gct gct taggagtcta gaacactgat ctggaaggag gtgaaggtga aggcatggtg       857
Ala Ala tctatgtgct atggcgactg gcaagttaat ggggccgcat ggatgactgc tgctcttgtt      917
tttttaagct cgtctgccgt atgctttgtt tttttaggct tcaaggactg acaattgcaa      977
gaatgcagtg tttatgtaag aggttgtttg ctggaatagg attgctgtaa ctgtaatgtt     1037
gttctccgaa aaaaaaaaaa aaaaa                                          1062

<210> SEQ ID NO 24
<211> LENGTH: 212
<212> TYPE: PRT
<213> ORGANISM: Zea mays

<400> SEQUENCE: 24
```

-continued

```
Met Ser Val Thr Lys Phe Ile Lys Cys Val Thr Val Gly Asp Val Ala
 1               5                  10                  15

Val Gly Lys Thr Cys Met Leu Ile Cys Tyr Thr Ser Asn Lys Phe Pro
            20                  25                  30

Thr Asp Tyr Ile Pro Thr Val Phe Asp Asn Phe Ser Ala Asn Val Ser
        35                  40                  45

Val Asp Gly Ser Ile Val Asn Leu Gly Leu Trp Asp Thr Ala Gly Gln
 50                  55                  60

Glu Asp Tyr Ser Arg Leu Arg Pro Leu Ser Tyr Arg Gly Ala Asp Val
 65                  70                  75                  80

Phe Val Leu Ala Phe Ser Leu Ile Ser Arg Ala Ser Tyr Glu Asn Val
                85                  90                  95

Leu Lys Lys Trp Val Pro Glu Leu Arg Arg Phe Ala Pro Asp Val Pro
            100                 105                 110

Val Val Leu Val Gly Thr Lys Leu Asp Leu Arg Asp His Arg Ala Tyr
            115                 120                 125

Leu Ala Asp His Pro Gly Ala Ser Thr Ile Thr Thr Ala Gln Gly Glu
        130                 135                 140

Glu Leu Arg Arg Gln Ile Gly Ala Ala Ala Tyr Ile Glu Cys Ser Ser
145                 150                 155                 160

Lys Thr Gln Gln Asn Val Lys Ser Val Phe Asp Thr Ala Ile Lys Val
                165                 170                 175

Val Leu Gln Pro Pro Arg Arg Arg Glu Ala Thr Pro Ala Arg Arg Lys
            180                 185                 190

Asn Arg Arg Gly Ser Gly Cys Ser Ile Met Asn Leu Met Cys Gly Ser
            195                 200                 205

Thr Cys Ala Ala
        210
```

<210> SEQ ID NO 25
<211> LENGTH: 1127
<212> TYPE: DNA
<213> ORGANISM: Zea mays
<220> FEATURE:
<221> NAME/KEY: CDS
<222> LOCATION: (190)...(831)

<400> SEQUENCE: 25

```
gtcgacccac gcgtccgccc agaagtcacg caccaaacac caccaccaaa gaaggcgaga       60
acgtactccg tccctcccct ccccctccct ccccttcccc tcgaggctcc aggaccgtct      120
cctcgcctgc tcatccgccg ctgcttccct tctctgggct cggagaaccg gagagaagcg      180 cgcgcggcc atg gcg tcc agc gcc tct cgg ttc atc aag tgc gtc acg gtc    231
          Met Ala Ser Ser Ala Ser Arg Phe Ile Lys Cys Val Thr Val
           1               5                  10 ggc gac ggt gcc gtg ggc aag aac tgt atg ctc atc tgc tac acc agc      279
Gly Asp Gly Ala Val Gly Lys Asn Cys Met Leu Ile Cys Tyr Thr Ser
 15                  20                  25                  30 aac aag ttc ccc act gac tac ata cct acg gtg ttc gac aat ttc agt      327
Asn Lys Phe Pro Thr Asp Tyr Ile Pro Thr Val Phe Asp Asn Phe Ser
                 35                  40                  45 gca aat gta gtt gtg gat ggc acc act gtg aat ttg ggc ctt tgg gat      375
Ala Asn Val Val Val Asp Gly Thr Thr Val Asn Leu Gly Leu Trp Asp
             50                  55                  60 acc gct ggg cag gaa gat tac aac cgc ctg agg cct cta agc tac cga      423
Thr Ala Gly Gln Glu Asp Tyr Asn Arg Leu Arg Pro Leu Ser Tyr Arg
         65                  70                  75
```

```
ggt gca gat gtt ttc gtg ctt gca ttc tca ctt gtg agc cga gct agc    471
Gly Ala Asp Val Phe Val Leu Ala Phe Ser Leu Val Ser Arg Ala Ser
    80                  85                  90 tat gag aat atc atg aag aag tgg ata cca gag ctt caa cat tat gca    519
Tyr Glu Asn Ile Met Lys Lys Trp Ile Pro Glu Leu Gln His Tyr Ala
 95                 100                 105                 110 cct ggg gtg ccc gtt gtt ttg gca ggc aca aaa ttg gat ctt cgt gaa    567
Pro Gly Val Pro Val Val Leu Ala Gly Thr Lys Leu Asp Leu Arg Glu
                115                 120                 125 gac aag cac tac ttg atg gac cat cct gga ttg gtg cct gtt acc act    615
Asp Lys His Tyr Leu Met Asp His Pro Gly Leu Val Pro Val Thr Thr
            130                 135                 140 gca cag ggg gag gaa ctt cgt aga caa att ggt gct atg tat tac att    663
Ala Gln Gly Glu Glu Leu Arg Arg Gln Ile Gly Ala Met Tyr Tyr Ile
        145                 150                 155 gaa tgc agc tca aag aca cag cag aat gtc aaa gct gtg ttc gat gct    711
Glu Cys Ser Ser Lys Thr Gln Gln Asn Val Lys Ala Val Phe Asp Ala
    160                 165                 170 gcc atc aag gta gta atc cag cct cca act aaa ata aga gaa aag aag    759
Ala Ile Lys Val Val Ile Gln Pro Pro Thr Lys Ile Arg Glu Lys Lys
175                 180                 185                 190 aag aaa aaa tca cgc aaa gga tgt tct atg atg aac atc ttc ggt gga    807
Lys Lys Lys Ser Arg Lys Gly Cys Ser Met Met Asn Ile Phe Gly Gly
                195                 200                 205 aga aaa atg cta tgc ttc aag tcc tgaatggttc aagggggtct tacatggact    861
Arg Lys Met Leu Cys Phe Lys Ser
            210 gataccacga gtgtgacccc gagtttgcga agcttgaaat cttgatgtgc tcgttgcgca    921 tgtgtatatt tgcacctttg gttattaatg actagaggta ggtaattgaa actagtctgc    981 ttaagcgttc tgcactgctg gtgtggttag ctctatgagt taagcagttc gacagaggcc   1041 aaaccgacag tgagattttg ttctttcatg gaaatgtgcc aatgtcacag cttttttcgtg   1101 aaaaaaaaaa aaaaaaaaa aaaaaa                                        1127

<210> SEQ ID NO 26
<211> LENGTH: 214
<212> TYPE: PRT
<213> ORGANISM: Zea mays

<400> SEQUENCE: 26

Met Ala Ser Ser Ala Ser Arg Phe Ile Lys Cys Val Thr Val Gly Asp
 1               5                  10                  15

Gly Ala Val Gly Lys Asn Cys Met Leu Ile Cys Tyr Thr Ser Asn Lys
                20                  25                  30

Phe Pro Thr Asp Tyr Ile Pro Thr Val Phe Asp Asn Phe Ser Ala Asn
            35                  40                  45

Val Val Val Asp Gly Thr Thr Val Asn Leu Gly Leu Trp Asp Thr Ala
        50                  55                  60

Gly Gln Glu Asp Tyr Asn Arg Leu Arg Pro Leu Ser Tyr Arg Gly Ala
65                  70                  75                  80

Asp Val Phe Val Leu Ala Phe Ser Leu Val Ser Arg Ala Ser Tyr Glu
                85                  90                  95

Asn Ile Met Lys Lys Trp Ile Pro Glu Leu Gln His Tyr Ala Pro Gly
            100                 105                 110

Val Pro Val Val Leu Ala Gly Thr Lys Leu Asp Leu Arg Glu Asp Lys
        115                 120                 125

His Tyr Leu Met Asp His Pro Gly Leu Val Pro Val Thr Thr Ala Gln
```

```
                130             135             140
Gly Glu Glu Leu Arg Arg Gln Ile Gly Ala Met Tyr Tyr Ile Glu Cys
145                 150                 155                 160

Ser Ser Lys Thr Gln Gln Asn Val Lys Ala Val Phe Asp Ala Ala Ile
                165                 170                 175

Lys Val Val Ile Gln Pro Pro Thr Lys Ile Arg Glu Lys Lys Lys Lys
            180                 185                 190

Lys Ser Arg Lys Gly Cys Ser Met Met Asn Ile Phe Gly Gly Arg Lys
        195                 200                 205

Met Leu Cys Phe Lys Ser
    210

<210> SEQ ID NO 27
<211> LENGTH: 1393
<212> TYPE: DNA
<213> ORGANISM: Zea mays
<220> FEATURE:
<221> NAME/KEY: CDS
<222> LOCATION: (398)...(988)

<400> SEQUENCE: 27
gtcgacccac gcgtccgcgg acgcgtgggc ggacgcgtgg gtccccaccc accaccgcgc     60
cgggccacca ccaccactc taccctcccc tccccaccac cactagcacc caccgtcccg    120
gcgcggagac cgcttccctc cctccgcctc cgcaaccctc tcccgcctcg cccgcgcctc    180
cctccatttg tccgcggctc ccctccctcc cgatcttaac caccccgccac ccggcttcct   240 ctccccttc ttcctccctc aaaccagacg ctcgcccccc tttcctccac gcctatcttc    300
ttcagacgac cagcaggagg tacgaggaag accaccctagg aggcctctct ctctctctcc   360
ccagccaccc ccgtagcgag agggagggcg gaagagg atg agc gcg tcc agg ttc    415
                                         Met Ser Ala Ser Arg Phe
                                         1               5 ata aag tgc gtc acg gtc ggg gac ggc gcc gtc ggc aag aac tgc atg    463
Ile Lys Cys Val Thr Val Gly Asp Gly Ala Val Gly Lys Asn Cys Met
            10                  15                  20 ctc atc tcc tac acc tcc aac acc ttc ccc acc gac tat gtt ccg aca    511
Leu Ile Ser Tyr Thr Ser Asn Thr Phe Pro Thr Asp Tyr Val Pro Thr
        25                  30                  35 gtg ttt gat aac ttc agt gcc aac gtt gtg gtt gat ggt aat act gtc    559
Val Phe Asp Asn Phe Ser Ala Asn Val Val Val Asp Gly Asn Thr Val
    40                  45                  50 aac ctc ggc ctc tgg gac act gca ggt caa gag gat tac aac aga ctg    607
Asn Leu Gly Leu Trp Asp Thr Ala Gly Gln Glu Asp Tyr Asn Arg Leu
55                  60                  65                  70 aga cca ctg agc tat cgt gga gct gat gtt ttt ctt ctg gct ttc tca    655
Arg Pro Leu Ser Tyr Arg Gly Ala Asp Val Phe Leu Leu Ala Phe Ser
                75                  80                  85 ctg atc agt aag gcc agc tat gag aat gtt tcg aag aag tgg ata cct    703
Leu Ile Ser Lys Ala Ser Tyr Glu Asn Val Ser Lys Lys Trp Ile Pro
            90                  95                  100 gaa ctg aag cat tat gca cct ggt gtg cca att att ctc gta ggg aca    751
Glu Leu Lys His Tyr Ala Pro Gly Val Pro Ile Ile Leu Val Gly Thr
        105                 110                 115 aag ctt gat ctt cga gac gac aag cag ttc ttt gtg gac cat cct ggt    799
Lys Leu Asp Leu Arg Asp Asp Lys Gln Phe Phe Val Asp His Pro Gly
    120                 125                 130 gct gtc cct atc act act gct cag gga gag gag cta aga aag caa ata    847
Ala Val Pro Ile Thr Thr Ala Gln Gly Glu Glu Leu Arg Lys Gln Ile
135                 140                 145                 150
```

```
ggc gct cca tac tac atc gaa tgc agc tcg aag acc caa cta aac gtg      895
Gly Ala Pro Tyr Tyr Ile Glu Cys Ser Ser Lys Thr Gln Leu Asn Val
            155                 160                 165 aag ggc gtc ttc gat gcg gcg ata aag gtt gtg ctg cag ccg cct aag      943
Lys Gly Val Phe Asp Ala Ala Ile Lys Val Val Leu Gln Pro Pro Lys
            170                 175                 180 gcg aag aag aag aaa aag gtg cag agg ggg gcg tgc tcc att ttg          988
Ala Lys Lys Lys Lys Lys Val Gln Arg Gly Ala Cys Ser Ile Leu
            185                 190                 195 tgatctaatc atcggtagat gaagaaacaa gggcgaaggt gccatggctt tatcatcgtc   1048
gcgtcttgct tcagtggaac agcatgaatg gtccccaccc cctctaggtt tactggcggc   1108
tcggctgcag cgagttctca tctctttgtc gaggcattga gcgatatgtt tgtttcattt   1168
tcctccttcc tgccttgtga ttatctggtg tgtgtgtgtg tgtgactgac gaagtcgcgg   1228
cgattaggta actcgcttag aaggtatttc ccgtgtttga gcaaaagaaa gtatccctgt   1288
tatctctgtt ccataagtta gacatgatgt aatcgtacta agtttatttt tacttatttc   1348
acttgaatgg aaaagtatgc ttcccattta aaaaaaaaaa aaaaa                   1393

<210> SEQ ID NO 28
<211> LENGTH: 197
<212> TYPE: PRT
<213> ORGANISM: Zea mays

<400> SEQUENCE: 28

Met Ser Ala Ser Arg Phe Ile Lys Cys Val Thr Val Gly Asp Gly Ala
 1               5                  10                  15

Val Gly Lys Asn Cys Met Leu Ile Ser Tyr Thr Ser Asn Thr Phe Pro
                20                  25                  30

Thr Asp Tyr Val Pro Thr Val Phe Asp Asn Phe Ser Ala Asn Val Val
            35                  40                  45

Val Asp Gly Asn Thr Val Asn Leu Gly Leu Trp Asp Thr Ala Gly Gln
        50                  55                  60

Glu Asp Tyr Asn Arg Leu Arg Pro Leu Ser Tyr Arg Gly Ala Asp Val
65                  70                  75                  80

Phe Leu Leu Ala Phe Ser Leu Ile Ser Lys Ala Ser Tyr Glu Asn Val
                85                  90                  95

Ser Lys Lys Trp Ile Pro Glu Leu Lys His Tyr Ala Pro Gly Val Pro
                100                 105                 110

Ile Ile Leu Val Gly Thr Lys Leu Asp Leu Arg Asp Asp Lys Gln Phe
            115                 120                 125

Phe Val Asp His Pro Gly Ala Val Pro Ile Thr Thr Ala Gln Gly Glu
        130                 135                 140

Glu Leu Arg Lys Gln Ile Gly Ala Pro Tyr Tyr Ile Glu Cys Ser Ser
145                 150                 155                 160

Lys Thr Gln Leu Asn Val Lys Gly Val Phe Asp Ala Ala Ile Lys Val
                165                 170                 175

Val Leu Gln Pro Pro Lys Ala Lys Lys Lys Lys Val Gln Arg Gly
            180                 185                 190

Ala Cys Ser Ile Leu
        195

<210> SEQ ID NO 29
<211> LENGTH: 1045
<212> TYPE: DNA
<213> ORGANISM: Zea mays
```

<220> FEATURE:
<221> NAME/KEY: CDS
<222> LOCATION: (45)...(704)

<400> SEQUENCE: 29

```
gaattcggca cgagctggct cgtgcagcgg cggcagtgag agcg atg agc gcg gcg           56
                                                  Met Ser Ala Ala
                                                    1 gca gcg gcg gcg gcg agc tcg gtc acc aag ttc atc aag tgc gtc acg          104
Ala Ala Ala Ala Ala Ser Ser Val Thr Lys Phe Ile Lys Cys Val Thr
  5              10                  15                  20 gtc ggc gat ggg gcc gtc ggg aag aac tgc atg ctc atc tgc tac acc          152
Val Gly Asp Gly Ala Val Gly Lys Asn Cys Met Leu Ile Cys Tyr Thr
                      25                  30                  35 tgc aac aag ttc ccc acg gat tac atc ccc acc gta ttt gac aac ttc          200
Cys Asn Lys Phe Pro Thr Asp Tyr Ile Pro Thr Val Phe Asp Asn Phe
                  40                  45                  50 agc gcc aat gtc tcc gtg ggt ggg agc atc gtc aac ttg ggc ctc tgg          248
Ser Ala Asn Val Ser Val Gly Gly Ser Ile Val Asn Leu Gly Leu Trp
              55                  60                  65 gac acg gca ggc cag gag gat tac agc agg ttg agg cct ctc agc tac          296
Asp Thr Ala Gly Gln Glu Asp Tyr Ser Arg Leu Arg Pro Leu Ser Tyr
 70                  75                  80 agg ggt gct gat gtg ttc atc ctc tcc ttc tcc ctg gtc agc agg gcg          344
Arg Gly Ala Asp Val Phe Ile Leu Ser Phe Ser Leu Val Ser Arg Ala
 85                  90                  95                 100 agc tat gag aac gtc ctg aag aag tgg atg cca gag ctt cgc cga ttt          392
Ser Tyr Glu Asn Val Leu Lys Lys Trp Met Pro Glu Leu Arg Arg Phe
                105                 110                 115 tca cct act gtt cct gta gtt ctt gtt gga acc aaa cta gat ctc cgt          440
Ser Pro Thr Val Pro Val Val Leu Val Gly Thr Lys Leu Asp Leu Arg
                120                 125                 130 gaa gac aga tct tac ctt gct gac cat tct gct gct tcc atc atc tct          488
Glu Asp Arg Ser Tyr Leu Ala Asp His Ser Ala Ala Ser Ile Ile Ser
            135                 140                 145 act gaa cag gga gaa gag ctc agg aag cag ata ggt gct gtg gcg tac          536
Thr Glu Gln Gly Glu Glu Leu Arg Lys Gln Ile Gly Ala Val Ala Tyr
        150                 155                 160 ata gaa tgc agc tca aag aca cag agg aac gta aag gct gtg ttc gac          584
Ile Glu Cys Ser Ser Lys Thr Gln Arg Asn Val Lys Ala Val Phe Asp
165                 170                 175                 180 act gca att aaa gta gtg ctg caa cca ccg agg aga aga gaa gtt acc          632
Thr Ala Ile Lys Val Val Leu Gln Pro Pro Arg Arg Arg Glu Val Thr
                185                 190                 195 agg aag aaa atg aag aca agt tcg aat cag tct ctg aga aga tac ctc          680
Arg Lys Lys Met Lys Thr Ser Ser Asn Gln Ser Leu Arg Arg Tyr Leu
                200                 205                 210 tgt gga agc gga tgt ttc aca tcg taaagcacag actcttctgc gactgttgta         734
Cys Gly Ser Gly Cys Phe Thr Ser
            215                 220 ctggacttgc tagatggttg cagctctatg aatgagtagt cccctccgca gccactggga        794
acttctggtt ctctgctacc ttccgataga gtgctctttt gcgttcacca gctgagaaaa        854
atgaagcgag gttctagttt ataaattccc tacgaggtgt accttcttta gtatgaatgg        914
tgggctattt agcagttcag caaagtgtga agtgacccct ctatgcatgt tttgtttcca        974
aaaactgatg ttgctaaatg gctaatgaat ggttatggtc gcaccggaag aaaaaaaaaa       1034
aaaaaaaaaa a                                                            1045
```

```
<210> SEQ ID NO 30
<211> LENGTH: 220
<212> TYPE: PRT
<213> ORGANISM: Zea mays

<400> SEQUENCE: 30

Met Ser Ala Ala Ala Ala Ala Ser Ser Val Thr Lys Phe Ile
 1               5                  10                  15

Lys Cys Val Thr Val Gly Asp Gly Ala Val Gly Lys Asn Cys Met Leu
                20                  25                  30

Ile Cys Tyr Thr Cys Asn Lys Phe Pro Thr Asp Tyr Ile Pro Thr Val
            35                  40                  45

Phe Asp Asn Phe Ser Ala Asn Val Ser Val Gly Gly Ser Ile Val Asn
 50                  55                  60

Leu Gly Leu Trp Asp Thr Ala Gly Gln Glu Asp Tyr Ser Arg Leu Arg
65                  70                  75                  80

Pro Leu Ser Tyr Arg Gly Ala Asp Val Phe Ile Leu Ser Phe Ser Leu
                85                  90                  95

Val Ser Arg Ala Ser Tyr Glu Asn Val Leu Lys Lys Trp Met Pro Glu
            100                 105                 110

Leu Arg Arg Phe Ser Pro Thr Val Pro Val Val Leu Val Gly Thr Lys
        115                 120                 125

Leu Asp Leu Arg Glu Asp Arg Ser Tyr Leu Ala Asp His Ser Ala Ala
130                 135                 140

Ser Ile Ile Ser Thr Glu Gln Gly Glu Glu Leu Arg Lys Gln Ile Gly
145                 150                 155                 160

Ala Val Ala Tyr Ile Glu Cys Ser Ser Lys Thr Gln Arg Asn Val Lys
                165                 170                 175

Ala Val Phe Asp Thr Ala Ile Lys Val Val Leu Gln Pro Pro Arg Arg
            180                 185                 190

Arg Glu Val Thr Arg Lys Lys Met Lys Thr Ser Ser Asn Gln Ser Leu
        195                 200                 205

Arg Arg Tyr Leu Cys Gly Ser Gly Cys Phe Thr Ser
210                 215                 220

<210> SEQ ID NO 31
<211> LENGTH: 1058
<212> TYPE: DNA
<213> ORGANISM: Zea mays
<220> FEATURE:
<221> NAME/KEY: CDS
<222> LOCATION: (176)...(766)

<400> SEQUENCE: 31
gaattcggca cgagagctct caagacggcc gacggccggc ttgcctacct gctcccatcc     60
ttcccgaggg accgagaaag ataagaaagg cggtggtcaa cttgtgtcct gaggtgcccg    120
tagaagccca aggacaagaa acaaggagaa gagtagatct acatctactc caccg atg    178
                                                                Met
                                                                 1 agc gcg tct cgg ttc atc aag tgc gtc acc gtg ggg gac ggt gcc gtc    226
Ser Ala Ser Arg Phe Ile Lys Cys Val Thr Val Gly Asp Gly Ala Val
          5                  10                  15 gga aag aac tgc atg ctc atc tcc tac aca tcc aac act ttc ccc act    274
Gly Lys Asn Cys Met Leu Ile Ser Tyr Thr Ser Asn Thr Phe Pro Thr
     20                  25                  30 gac tat gtt cca act gtg ttc gac aac ttc agt gcc aat gtt gtg gtt    322
Asp Tyr Val Pro Thr Val Phe Asp Asn Phe Ser Ala Asn Val Val Val
 35                  40                  45
```

```
gac ggg agc act gtc aac ttg ggt ctg tgg gat aca gca gga caa gaa    370
Asp Gly Ser Thr Val Asn Leu Gly Leu Trp Asp Thr Ala Gly Gln Glu
 50                  55                  60                  65 gat tac aat aga ctg cgt ccg ttg agc tat cgt ggt gct gat gtt ttt    418
Asp Tyr Asn Arg Leu Arg Pro Leu Ser Tyr Arg Gly Ala Asp Val Phe
                 70                  75                  80 ctg ctc gcc ttt tct ctt atc agc aaa gca agc tat gag aat gtc tct    466
Leu Leu Ala Phe Ser Leu Ile Ser Lys Ala Ser Tyr Glu Asn Val Ser
                     85                  90                  95 aag aag tgg gtt cct gaa tta agg cac tat gct cct ggc gtg ccc ata    514
Lys Lys Trp Val Pro Glu Leu Arg His Tyr Ala Pro Gly Val Pro Ile
            100                 105                 110 atc ctt gtt ggg aca aaa ctt gat ctg cgt gat gat aag cag ttt ttt    562
Ile Leu Val Gly Thr Lys Leu Asp Leu Arg Asp Asp Lys Gln Phe Phe
        115                 120                 125 gtt gat cac cct ggt gct gtt cca att tcc act gcc cag ggc gaa gag    610
Val Asp His Pro Gly Ala Val Pro Ile Ser Thr Ala Gln Gly Glu Glu
130                 135                 140                 145 ctg agg aag cta att ggt gct gcc gcc tac atc gaa tgc agt tca aaa    658
Leu Arg Lys Leu Ile Gly Ala Ala Ala Tyr Ile Glu Cys Ser Ser Lys
                150                 155                 160 atc cag cag aac ata aaa gca gtg ttt gac gca gca att aag gtg gtt    706
Ile Gln Gln Asn Ile Lys Ala Val Phe Asp Ala Ala Ile Lys Val Val
                    165                 170                 175 ctc cag cca cca aag caa aag aag agg aag aag aag gtg cag aag gga    754
Leu Gln Pro Pro Lys Gln Lys Lys Arg Lys Lys Lys Val Gln Lys Gly
                180                 185                 190 tgc acc att ttg taactacaaa cggtagaggg caacagtctg gctgcggcgc       806
Cys Thr Ile Leu
            195 tgctgccaat gataaccatc gcctccttgc tgtataatat atcgcctgat catgccacca  866 gcatgcacaa gggagatggt ggttttagga tccttgtcct actgtgttgt gtagaccacc  926 gggtgtagtt gactgtatct ggttgtttgt atgtatggac aagacaaaac tagcactgca  986 gatggtatgg taaggcgtaa gcaaatacaa tatgacattg gtccagttcc aggaaaaaaa  1046 aaaaaaaaaa aa                                                     1058

<210> SEQ ID NO 32
<211> LENGTH: 197
<212> TYPE: PRT
<213> ORGANISM: Zea mays

<400> SEQUENCE: 32

Met Ser Ala Ser Arg Phe Ile Lys Cys Val Thr Val Gly Asp Gly Ala
 1               5                  10                  15

Val Gly Lys Asn Cys Met Leu Ile Ser Tyr Thr Ser Asn Thr Phe Pro
            20                  25                  30

Thr Asp Tyr Val Pro Thr Val Phe Asp Asn Phe Ser Ala Asn Val Val
        35                  40                  45

Val Asp Gly Ser Thr Val Asn Leu Gly Leu Trp Asp Thr Ala Gly Gln
 50                  55                  60

Glu Asp Tyr Asn Arg Leu Arg Pro Leu Ser Tyr Arg Gly Ala Asp Val
65                  70                  75                  80

Phe Leu Leu Ala Phe Ser Leu Ile Ser Lys Ala Ser Tyr Glu Asn Val
                85                  90                  95

Ser Lys Lys Trp Val Pro Glu Leu Arg His Tyr Ala Pro Gly Val Pro
            100                 105                 110
```

```
Ile Ile Leu Val Gly Thr Lys Leu Asp Leu Arg Asp Asp Lys Gln Phe
        115                 120                 125

Phe Val Asp His Pro Gly Ala Val Pro Ile Ser Thr Ala Gln Gly Glu
130                 135                 140

Glu Leu Arg Lys Leu Ile Gly Ala Ala Ala Tyr Ile Glu Cys Ser Ser
145                 150                 155                 160

Lys Ile Gln Gln Asn Ile Lys Ala Val Phe Asp Ala Ala Ile Lys Val
                165                 170                 175

Val Leu Gln Pro Pro Lys Gln Lys Arg Lys Lys Lys Val Gln Lys
                180                 185                 190

Gly Cys Thr Ile Leu
        195

<210> SEQ ID NO 33
<211> LENGTH: 1062
<212> TYPE: DNA
<213> ORGANISM: Zea mays
<220> FEATURE:
<221> NAME/KEY: CDS
<222> LOCATION: (172)...(807)

<400> SEQUENCE: 33
gggtcgaccc acgcgtccgg gagaagataa gcaaggcaag gcaaccgttg tcgttgtctc      60
tgtccctccg cttcctgctc tcttgcttgc tgcttgccct cggagcagtg ccttctgccg     120
ccgccgccgc cgccgcctgt tgtgagaagg agaggccggg gctgggagga g atg agc     177
                                                           Met Ser
                                                             1 gtg acc aag ttc atc aag tgc gtc acg gtg ggg gac ggc gcg gtg ggc     225
Val Thr Lys Phe Ile Lys Cys Val Thr Val Gly Asp Gly Ala Val Gly
        5                   10                  15 aag aac tgc atg ctc atc tgc tac acc agc aac aag ttc ccc acg gat     273
Lys Asn Cys Met Leu Ile Cys Tyr Thr Ser Asn Lys Phe Pro Thr Asp
    20                  25                  30 tac atc ccc acg gtg ttc gac aac ttc agc gcc aac gtc tcc gtg gac     321
Tyr Ile Pro Thr Val Phe Asp Asn Phe Ser Ala Asn Val Ser Val Asp
35                  40                  45                  50 ggc agc atc gtc aac ctg ggc ctt tgg gac act gca gga caa gag gac     369
Gly Ser Ile Val Asn Leu Gly Leu Trp Asp Thr Ala Gly Gln Glu Asp
            55                  60                  65 tac agc aga ttg cgg cca ctg agc tac agg ggc gcg gac gtg ttc gtg     417
Tyr Ser Arg Leu Arg Pro Leu Ser Tyr Arg Gly Ala Asp Val Phe Val
        70                  75                  80 ctg gcc ttc tcc ttg atc agc agg gcg agc tat gag aac gtc ctt aag     465
Leu Ala Phe Ser Leu Ile Ser Arg Ala Ser Tyr Glu Asn Val Leu Lys
    85                  90                  95 aag tgg gtg cca gag ctt cgc aga ttc gcg ccc gac gtc ccg gtc gtt     513
Lys Trp Val Pro Glu Leu Arg Arg Phe Ala Pro Asp Val Pro Val Val
100                 105                 110 ctt gtc ggg acc aag tta gat ctc cgt gac cac agg gcc tac ctt gct     561
Leu Val Gly Thr Lys Leu Asp Leu Arg Asp His Arg Ala Tyr Leu Ala
115                 120                 125                 130 gac cat cct gga gcg tcg acg atc acg acg gca cag ggc gaa gaa ctg     609
Asp His Pro Gly Ala Ser Thr Ile Thr Thr Ala Gln Gly Glu Glu Leu
            135                 140                 145 agg agg cag atc ggc gct gcg gct tac atc gag tgc agt tcc aaa acg     657
Arg Arg Gln Ile Gly Ala Ala Ala Tyr Ile Glu Cys Ser Ser Lys Thr
        150                 155                 160 cag cag aat gtc aag tcg gtc ttc gac aca gcc atc aaa gtg gtc ctt     705
Gln Gln Asn Val Lys Ser Val Phe Asp Thr Ala Ile Lys Val Val Leu
```

```
Gln Gln Asn Val Lys Ser Val Phe Asp Thr Ala Ile Lys Val Val Leu
        165                 170                 175 cag ccc ccg cgg agg agg gag gcg acg cct gcc agg agg aag aac agg        753
Gln Pro Pro Arg Arg Arg Glu Ala Thr Pro Ala Arg Arg Lys Asn Arg
    180                 185                 190 cgt ggc tcc ggg tgc tct atc atg aac ctc atg tgt ggc agc acg tgc        801
Arg Gly Ser Gly Cys Ser Ile Met Asn Leu Met Cys Gly Ser Thr Cys
195                 200                 205                 210 gct gct taggagtcta gaacactgat ctggaaggag gtgaaggtga aggcatggtg         857
Ala Ala tctatgtgct atggcgactg gcaagttaat ggggccgcat ggatgactgc tgctcttgtt     917
tttttaagct cgtctgccgt atgctttgtt tttttaggct tcaaggactg acaattgcaa    977
gaatgcagtg tttatgtaag aggttgtttg ctggaatagg attgctgtaa ctgtaatgtt    1037
gttctccgaa aaaaaaaaaa aaaaa                                          1062
```

<210> SEQ ID NO 34
<211> LENGTH: 212
<212> TYPE: PRT
<213> ORGANISM: Zea mays

<400> SEQUENCE: 34

```
Met Ser Val Thr Lys Phe Ile Lys Cys Val Thr Val Gly Asp Gly Ala
1               5                   10                  15

Val Gly Lys Asn Cys Met Leu Ile Cys Tyr Thr Ser Asn Lys Phe Pro
            20                  25                  30

Thr Asp Tyr Ile Pro Thr Val Phe Asp Asn Phe Ser Ala Asn Val Ser
        35                  40                  45

Val Asp Gly Ser Ile Val Asn Leu Gly Leu Trp Asp Thr Ala Gly Gln
    50                  55                  60

Glu Asp Tyr Ser Arg Leu Arg Pro Leu Ser Tyr Arg Gly Ala Asp Val
65                  70                  75                  80

Phe Val Leu Ala Phe Ser Leu Ile Ser Arg Ala Ser Tyr Glu Asn Val
                85                  90                  95

Leu Lys Lys Trp Val Pro Glu Leu Arg Arg Phe Ala Pro Asp Val Pro
            100                 105                 110

Val Val Leu Val Gly Thr Lys Leu Asp Leu Arg Asp His Arg Ala Tyr
        115                 120                 125

Leu Ala Asp His Pro Gly Ala Ser Thr Ile Thr Thr Ala Gln Gly Glu
    130                 135                 140

Glu Leu Arg Arg Gln Ile Gly Ala Ala Ala Tyr Ile Glu Cys Ser Ser
145                 150                 155                 160

Lys Thr Gln Gln Asn Val Lys Ser Val Phe Asp Thr Ala Ile Lys Val
                165                 170                 175

Val Leu Gln Pro Pro Arg Arg Arg Glu Ala Thr Pro Ala Arg Arg Lys
            180                 185                 190

Asn Arg Arg Gly Ser Gly Cys Ser Ile Met Asn Leu Met Cys Gly Ser
        195                 200                 205

Thr Cys Ala Ala
    210
```

<210> SEQ ID NO 35
<211> LENGTH: 29
<212> TYPE: DNA
<213> ORGANISM: Artificial Sequence
<220> FEATURE:
<223> OTHER INFORMATION: Primer designed to generate G to V mutation.

<400> SEQUENCE: 35
tcacggtcgg cgacgtggcc gtgggcaag					29

<210> SEQ ID NO 36
<211> LENGTH: 27
<212> TYPE: DNA
<213> ORGANISM: Artificial Sequence
<220> FEATURE:
<223> OTHER INFORMATION: Primer designed to generate T to N mutation

<400> SEQUENCE: 36
gccgtgggca agaactgtat gctcatc					27

<210> SEQ ID NO 37
<211> LENGTH: 46
<212> TYPE: DNA
<213> ORGANISM: Artificial Sequence
<220> FEATURE:
<223> OTHER INFORMATION: Primer designed for PCR cloning.

<400> SEQUENCE: 37
gaattcggat ccacacgaca ccatggcgtc cagcgcctct cggttc					46

<210> SEQ ID NO 38
<211> LENGTH: 45
<212> TYPE: DNA
<213> ORGANISM: Artificial Sequence
<220> FEATURE:
<223> OTHER INFORMATION: Primer designed for PCR cloning.

<400> SEQUENCE: 38
tctagagtta acacgacact caggacttga agcatagcat ttttc					45

<210> SEQ ID NO 39
<211> LENGTH: 29
<212> TYPE: DNA
<213> ORGANISM: Artificial Sequence
<220> FEATURE:
<223> OTHER INFORMATION: Primer designed to generate G to V mutation

<400> SEQUENCE: 39
tcacggtcgg ggacgtcgcc gtcggcaag					29

<210> SEQ ID NO 40
<211> LENGTH: 27
<212> TYPE: DNA
<213> ORGANISM: Artificial Sequence
<220> FEATURE:
<223> OTHER INFORMATION: Primer designed to generate T to N mutation

<400> SEQUENCE: 40
gccgtcggca agaactgcat gctcatc					27

<210> SEQ ID NO 41
<211> LENGTH: 46
<212> TYPE: DNA
<213> ORGANISM: Artificial Sequence
<220> FEATURE:
<223> OTHER INFORMATION: Primer designed for PCR cloning.

<400> SEQUENCE: 41
gaattcggat ccacacgaca ccatgagcgc gtccaggttc ataaag					46

<210> SEQ ID NO 42

```
<211> LENGTH: 46
<212> TYPE: DNA
<213> ORGANISM: Artificial Sequence
<220> FEATURE:
<223> OTHER INFORMATION: Primer designed for PCR cloning.

<400> SEQUENCE: 42
tctagagtta acacgacact cacaaaatgg agcacgcccc cctctg                        46

<210> SEQ ID NO 43
<211> LENGTH: 30
<212> TYPE: DNA
<213> ORGANISM: Artificial Sequence
<220> FEATURE:
<223> OTHER INFORMATION: Primer designed to generate G to V mutation

<400> SEQUENCE: 43
cacggtcggc gatgtggccg tcgggaagac                                          30

<210> SEQ ID NO 44
<211> LENGTH: 30
<212> TYPE: DNA
<213> ORGANISM: Artificial Sequence
<220> FEATURE:
<223> OTHER INFORMATION: Primer designed to generate T to N mutation

<400> SEQUENCE: 44
gccgtcggga agaactgcat gctcatctgc                                          30

<210> SEQ ID NO 45
<211> LENGTH: 46
<212> TYPE: DNA
<213> ORGANISM: Artificial Sequence
<220> FEATURE:
<223> OTHER INFORMATION: Primer designed for PCR cloning.

<400> SEQUENCE: 45
gaattcggat ccacacgaca ccatgagcgc ggcggcagcg gcggcg                        46

<210> SEQ ID NO 46
<211> LENGTH: 47
<212> TYPE: DNA
<213> ORGANISM: Artificial Sequence
<220> FEATURE:
<223> OTHER INFORMATION: Primer designed for PCR cloning

<400> SEQUENCE: 46
tctagagtta acacgacact tacgatgtga acatccgct tccacag                        47

<210> SEQ ID NO 47
<211> LENGTH: 32
<212> TYPE: DNA
<213> ORGANISM: Artificial Sequence
<220> FEATURE:
<223> OTHER INFORMATION: Primer designed to generate G to V mutation

<400> SEQUENCE: 47
gtcaccgtgg gggacgtggc cgtcggaaag ac                                       32

<210> SEQ ID NO 48
<211> LENGTH: 29
<212> TYPE: DNA
<213> ORGANISM: Artificial Sequence
<220> FEATURE:
<223> OTHER INFORMATION: Primer designed to generate T to N mutation

<400> SEQUENCE: 48
```

```
gccgtcggaa agaactgcat gctcatctc                                    29

<210> SEQ ID NO 49
<211> LENGTH: 46
<212> TYPE: DNA
<213> ORGANISM: Artificial Sequence
<220> FEATURE:
<223> OTHER INFORMATION: Primer designed for PCR cloning.

<400> SEQUENCE: 49
gaattcggat ccacacgaca ccatgagcgc gtctcggttc atcaag              46

<210> SEQ ID NO 50
<211> LENGTH: 46
<212> TYPE: DNA
<213> ORGANISM: Artificial Sequence
<220> FEATURE:
<223> OTHER INFORMATION: Primer designed for PCR cloning.

<400> SEQUENCE: 50
tctagagtta acacgacact tacaaaatgg tgcatccctt ctgcac              46

<210> SEQ ID NO 51
<211> LENGTH: 36
<212> TYPE: DNA
<213> ORGANISM: Artificial Sequence
<220> FEATURE:
<223> OTHER INFORMATION: Oligo used to remove clones containing poly A
      tail but no cDNA.

<400> SEQUENCE: 51
tcgacccacg cgtccgaaaa aaaaaaaaaa aaaaaa                          36
```

RAC-LIKE GENES AND METHODS OF USE

CROSS REFERENCE TO RELATED APPLICATION

This application claims the benefit of U.S. Provisional Application No. 60/111,919 filed Dec. 11, 1998 and U.S. Provisional Application No. 60/100,284 filed Sep. 14, 1998 and both of which are hereby incorporated by reference.

TECHNICAL FIELD

The present invention relates generally to plant molecular biology. More specifically, it relates to nucleic acids and methods for modulating their expression in plants to enhance disease resistance.

BACKGROUND OF THE INVENTION

Rho, rac, and cdc42 are members of a family of small GTP (guanosine triphosphate) binding proteins which function as molecular switches in regulating a variety of cellular processes in both plants and animals. One such process is the regulation of NADPH oxidase and the oxidative burst response which are involved in the defense response of both plants and animals to pathogens (Kwong, et al., *Journal of Biol Chem*, 270, No. 34: 19868–19872 (1995); Dusi, et al., *Biochem J*, 314: 409–412 (1996); Diekmann, et al., *Science* 265: 531–533 (1994); Purgin, et al., *The Plant Cell* 9: 2077–2091 (1997); Kleinberg, et al., *Biochemistry*, 33: 2490–2495 (1994); Prigmore, et al., *Journal of Biol Chem* 27, No. 18: 10717–10722 (1995); Irani, et al., *Science* 275: 1649–1652 (1997); Low, et al., *Advances in Molecular Genetics of Plant-Microbe Interactions* 3: 361–369 (1994) eds. M. J. Daniels, Kluwer Acadmic Publishers, Netherlands; Mehdy, et al., *Plant Physiol*. 105: 467472 (1994); Sundaresan, et al., *Biochem J* 318: 379–382 (1996)). The GTP binding proteins also function in altering the cytoskeleton and in cell transformation (for a review see Symon, M., *TIBS* 21: 178–181 (1996)). In plants, a Rho-like GTPase has been found to control pollen tube growth (Lin et al, *The Plant Cell* 9:1647–1659 (1997). Additionally, the GTP-binding proteins have been found to be regulators of transciptional activation (Hill, et al., *Cell* 81: 1159–1170 (1995); Chandra, et at., *Proc. Natl. Acad. Sci. USA* 93: 13393–13397 (1996)). Recently, it has been shown in mice that Rac proteins are involved in the growth and death of mammalian T cells (Lores, et al., *Oncogene* 15: 601–605 (1997)). Clearly, this family of GTP binding proteins control multiple functions in a plant or animal cell and are integral in the cellular defense against pathogens.

In plants, the Rho family is restricted to one large family of Rac-like proteins (Winge, et al., *Plant Molec Biology*, 35: 483–495 (1997)). Recently, it has been proposed that these proteins be given their own Rho subfamily designation, Rop (Lin, et al., supra). The plant Rac proteins are small, approximately 200 amino acid, soluble and show sequence homology. Plant Racs are activated by the binding of GTP and also have GTPase activity that allows them to cycle off to the inactive state. Various effector proteins can either increase or decrease the level of activation of Rac by promoting or inhibiting GTPase activity. In addition, single amino acid changes in Rac itself can alter the ability of Rac to cycle between active and inactive states. A change of glycine to valine at residue 12 in the highly conserved mammalian Racs results in total loss of GTPase activity, so that when the mutant Rac binds GTP it stays activated permanently, in other words a "dominant positive Rac is formed". Conversely, changing residue 18 from threonine to alanine causes loss of ability to bind GTP and hence causes permanent inactivation of Rac, in other words a "dominant negative Rac is formed". (See for example, Xuemi, et al., *Biochemistry*, 36: 626–632 (1997).)

The Rac proteins from plants show sequence homology with other Rac family members. In *Arabidopsis thaliana*, five Rac cDNAs have been cloned and sequenced. The Rac proteins in *A. thaliana* are all highly conserved, and the N-terminal portion, including the effector domain, share considerable homology to the animal Rac proteins (Winge, et al., supra). In plants the Rac proteins seem to be involved in the oxidative burst observed when plants are infected by a pathogen or an avirulent strain of a pathogen, inducing the disease response pathway, sometimes including the hypersensitivity response (HR). In the hypersensitivity response, cells contacted by the pathogen, and often neighboring cells, rapidly collapse and dry in a necrotic fleck. Other HR responses include the deposition of callose, the physical thickening of cell walls by lignification, and the synthesis of various antibiotic small molecules and proteins. Genetic factors in both the host and the pathogen determine the specificity of these local responses, which can be very effective in limiting the spread of infection.

Disease in plants is caused by biotic and abiotic causes. Biotic causes include fungi, viruses, bacteria, and nematodes. Of these, fungi are the most frequent causative agent of disease on plants. Abiotic causes of disease in plants include extremes in temperature, water, oxygen, soil pH, plus nutrient-element deficiencies and imbalances, excess heavy metals, and air pollution. A host of cellular processes enables plants to defend themselves from disease caused by pathogenic agents. These processes apparently form an integrated set of resistance mechanisms that is activated by initial infection and then limits further spread of the invading pathogenic microorganism.

As noted, among the causative agents of infectious disease of crop plants, the phytopathogenic fungi play the dominant role. Phytopathogenic fungi cause devastating epidemics, as well as causing significant annual crop yield losses. All of the approximately 300,000 species of flowering plant species can be host to only a few fungal species, and similarly, most fungi usually have a limited-host range.

Plant disease outbreaks have resulted in catastrophic crop failures that have triggered famines and caused major social change. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight. Accordingly, molecular methods are needed to supplement traditional breeding methods to protect plants from pathogen attack. Therefore molecular regulation of the plant Rac proteins is important in improving disease resistance in plants. The present invention provides five newly identified plant Rac genes and methods for modulating the expression of the plant Rac genes.

SUMMARY OF THE INVENTION

Generally, it is the object of the present invention to provide nucleic acids and proteins relating to Rac proteins that function as molecular switches. It is an object of the present invention to provide antigenic fragments of the proteins of the present invention. It is an object of the present invention to provide transgenic plants comprising the nucleic acids of the present invention. Additionally, it is an object of the present invention to provide methods for modulating, in a transgenic plant, the expression of the nucleic acids of the present invention.

Therefore, in one aspect, the present invention relates to an isolated nucleic acid comprising a member selected from the group consisting of (a) a polynucleotide encoding a polypeptide of the present invention; (b) a polynucleotide amplified from a *Zea mays* nucleic acid library using the primers of the present invention; (c) a polynucleotide comprising at least 25 contiguous bases of the polynucleotides of the present invention; (d) a polynucleotide having at least 64% sequence identity to the polynucleotides of the present invention; (e) a polynucleotide which hybridizes under stringent hybridization conditions to the polynucleotides of the present invention; (f) a polynucleotide selected from SEQ ID NOS: 1, 3, 5, 7, 9, 15, 17, 19, 21, 23, 25, 27, 29, 31, and 33 (g) a polynucleotide encoding a maize Rac polypeptide and (h) a polynucleotide complementary to a polynucleotide of (a) through (g). The isolated nucleic acid can be DNA. The isolated nucleic acid can also be RNA.

In another aspect, the present invention relates to vectors comprising the polynucleotides of the present invention. Also the present invention relates to recombinant expression cassettes, comprising a nucleic acid of the present invention operably linked to a promoter. In some embodiments, the nucleic acid is operably linked in antisense orientation to the promoter.

In another aspect, the present invention is directed to a host cell into which has been introduced the recombinant expression cassette. Examples of host cells included, but are not limited to, bacterial, yeast insect, plant, mammalian, and the like.

In yet another aspect, the present invention relates to a transgenic plant or plant cell comprising a polynucleotide of the present invention. Preferred plants containing the recombinant expression cassette of the present invention include but are not limited to maize, soybean, sunflower, sorghum, canola, wheat, alfalfa, cotton, rice, barley, and millet. The present invention also provides transgenic seed from the transgenic plant.

In another aspect, the present invention relates to an isolated protein selected from (a) a polypeptide comprising at least 25 contiguous amino acids of polypeptide of the present invention; (b) a polypeptide comprising at least 55% sequence identity to a polypeptide of the present invention; (d) a polypeptide encoded by a nucleic acid of the present invention; and (e) a polypeptide having the sequence of SEQ ID NOS: 2, 4, 6, 8, 10, 16, 18, 20, 22, 24, 26, 28, 30, 32, or 34. The present invention also relates to maize Rac proteins that have been mutated to either the dominant positive or dominant negative form.

In a further aspect, the present invention relates to a method of modulating expression of maize Rac proteins in a plant in order to modulate the oxidative burst, comprising the steps of (a) transforming a plant cell with a recombinant expression cassette comprising a maize Rac polynucleotide operably linked to a promoter; (b) growing the plant cell under plant growing conditions; and (c) inducing expression of the polynucleotide for a time sufficient to modulate expression of the genes in the plant. In some embodiments, the plant is maize. Expression of the maize Rac polynucleotide can be increased or decreased relative to a non-transformed control plant. Along with modulating the oxidative burst, transgenic plants expressing a maize Rac polynucleotide can induce defensive genes that provide the framework for plant defenses against environmental stress conditions. In addition by placing the polynucleotide of the present invention under a tissue preferred of tissue specific promoter, one can regulate programmed cell death. Another embodiment is the method of increasing transformation efficiency by transforming a cell with a maize Rac polynucleotide and regenerating said transformed cells into a transformed plant.

In an additional aspect, the present invention relates to the peptides illustrated in SEQ ID NOS: 11–14, and antibodies that recognize the epitopes of said peptides.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substance capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., *Science* 246: 1275–1281 (1989); and Ward, et al., *Nature* 341: 544–546 (1989); and Vaughan et al., *Nature Biotech.* 14: 309–314 (1996).

As used herein, "antisense orientation" includes reference to a duplex polynucleotide sequence which is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of chromosome which may be measured by reference to the linear segment of DNA which it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein which encodes a polypeptide also describes every possible silent variation of the nucleic acid. One of ordinary skill will recognize that each codon in a nucleic acid (except AUG, which is ordinarily the only codon for methionine) can be modified to yield a functionally identical molecule. Accordingly, each silent variation of a nucleic acid which encodes a polypeptide of the present invention is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for it's native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W. H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.* (*USA*), 82: 2306–2309 (1985)), or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477–498 (1989)). Thus, the maize preferred codon for a particular amino acid may be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, catalytically active form of the specified protein. A full-length sequence can be determined by size comparison relative to a control which is a native (non-synthetic) endogenous cellular form of the specified nucleic acid or protein. Methods to determine whether a sequence is full-length are well known in the art including such exemplary techniques as northern or western blots, primer extension, Si protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN<u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the expression vector. Host cells may be prokaryotic cells such as *E. coli*, or eukaryotic cells such as yeast, insect, amphibian, or mammalian cells. Preferably, host cells are monocotyledonous or dicotyledenous plant cells. A particularly preferred monocotyledonous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, generated to a particular epitope, to bind to that epitope to a detectably greater degree (e.g., at least 2-fold over background) than the antibody binds to substantially all other epitopes in a reaction mixture comprising the particular epitope. Immunologically reactive conditions are dependent upon the format of the antibody binding reaction and typically are those utilized in immunoassay protocols. See Harlow and Lane, *Antibodies, A Laboratory Manual*, Cold Spring Harbor Publications, New York (1988), for a description of immunoassay formats and conditions.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replica, or transiently expressed (e.g., transfected mRNA).

The terms "isolated" refers to material, such as a nucleic acid or a protein, which is: (1) substantially or essentially free from components which normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by non-natural, synthetic (i.e., "man-made") methods performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

Unless otherwise stated, the term "Rac nucleic acid" means a nucleic acid comprising a polynucleotide ("Rac polynucleotide") encoding a Rac polypeptide. A "Rac gene" refers to a non-heterologous genomic form of a full-length Rac polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994 Supplement).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. A particularly preferred plant is *Zea mays*.

As used herein, "polynucleotide" includes reference to a deoxyribopolynucleotide, ribopolynucleotide, or analogs thereof, that have the essential nature of a natural ribonucleotide in that they hybridize to nucleic acids in a manner similar to naturally occurring nucleotides. A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Exemplary modifications are described in most basic texts, such as, *Proteins—Structure and Molecular Properties*, 2nd ed., T. E. Creighton, W. H. Freeman and Company, New York (1993). Many detailed reviews are available on this subject, such as, for example, those provided by Wold, F., Posttranslational Protein Modifications: Perspectives and Prospects, pp. 1–12 in *Posttranslational Covalent Modification of Proteins*, B. C. Johnson, Ed., Academic Press, New York (1983); Seifter et al., *Meth. Enymol.* 182: 626–646 (1990) and Rattan et al., *Protein Synthesis: Posttranslational Modifications and Aging*, Ann. N.Y Acad. Sci. 663: 48–62 (1992). It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionineless amino terminal variants of the protein of the invention. In general, as used herein, the term polypeptide encompasses all such modifications, particularly those that are present in polypeptides synthesized by expressing a polynucleotide in a host cell.

Fragments and variants of the disclosed nucleotide sequences and proteins encoded thereby are also encompassed by the present invention. By "fragment" is intended a protion of the nucleotide sequence or a protein of the amino acid sequence and hence protein encoded thereby. Fragments of a nucleotide sequence may encode protein fragments that retain the biological activity of the native protein and hence affect defense responses, transformation efficiency, regulation of programmed cell death, and regulation of cytoskeleton reorganization. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a Rac nucleotide sequence that encodes a biologically active portion of a Rac protein of the invention will encode at least 15, 25, 30, 50, 100, 150, 200, 250, or 300 contiguous amino acids, or up to the total number of amino acids present in a full-length Rac protein of the invention. Fragments of a Rac nucleotide sequence that are useful as hybridization probes for PCR primers generally need not encode a biologically active portion of a Rac protein.

Thus, a fragment of a Rac nucleotide sequence may encode a biologically active portion of a Rac protein, or it may be a fragment that can be used as a hybridization probe or PCR primer using methods disclosed below. A biologically active portion of a Rac protein can be prepared by isolating a portion of one of the Rac nucleotide sequences of the invention, expressing the encoded portion of the Rac protein, and assessing the activity of the encoded portion of the Rac protein. Nucleic acid molecules that are fragments of a Rac nucleotide sequence comprise at least 15, 20, 25, 30, 40, 50, 60, 70, 80, 90, 100, 150, 200, 250, 300, 350, 400, 450, 500, 550, 600, 650, 700, 800, or 900 nucleotides, or up to the number of nucleotides present in a full-length Rac nucleotide sequence disclosed herein.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such Agrobacterium or Rhizobium. Examples of promoters under developmental control include promoters that preferentially initiate transcription in certain tissues, such as leaves, roots, seeds, fibres, xylem vessels, tracheids, or sclerenchyma. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

The term "Rac polypeptide" refer to one or more amino acid sequences, in glycosylated or non-glycosylated form. The term is also inclusive of fragments, variants, homologs, alleles or precursors (e.g., preproproteins or proproteins) thereof. A "Rac protein" comprises a Rac polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under tringent hybridization conditions, of a nucleic acid sequence to a specified nucleic acid arget sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC 3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267–284 (1984): $T_m = 81.5°$ C. $+16.6$ (log M)$+0.41$ (%GC)$-0.61$ (% form)$-500/L$; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

By "disease resistance" or "pathogen resistance" is intended that the plants avoid the disease symptoms which are the outcome of plant-pathogen interactions. That is, pathogens are prevented from causing plant diseases and the associated disease symptoms, or alternatively, the disease symptoms caused by the pathogen is minimized or lessened. The methods of the invention can be utilized to protect plants from disease, particularly those diseases that are caused by plant pathogens.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

GAP uses the algorithm of Needleman and Wunsch (J. Mol. Biol. 48: 443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively, for protein sequences. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50, 60, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89:10915).

Unless otherwise stated, sequence identity/similarity values provided herein refer to the value obtained using the BLAST 2.0 suite of programs using default parameters. Altschul et al., *Nucleic Acids Res.* 25:3389–3402 (1997) or GAP version 10 of Wisconsin Genetic Software Package using default parameters. Software for performing BLAST analyses is publicly available, e.g., through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

DETAILED DESCRIPTION OF THE INVENTION

Overview

The present invention provides, inter alia, compositions and methods for modulating (i.e., increasing or decreasing) the total levels of proteins of the present invention and/or altering their ratios in plants. Thus, the present invention provides utility in such exemplary applications as disease resistance or modification of the oxidative burst, improvement of plant transformation efficiency, regulation of programmed cell death, or regulation of cytoskeleton reorganization. In particular, the polypeptides of the present invention can be expressed at times or in quantities, which are not characteristic of non-recombinant plants.

The present invention also provides isolated nucleic acid comprising polynucleotides of sufficient length and complementarity to a Rac gene to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms) of the gene, or for use as molecular markers in plant breeding programs. The isolated nucleic acids of the present invention can also be used for recombinant expression of Rac polypeptides, or for use as immunogens in the preparation and/or screening of antibodies. The isolated nucleic acids of the present invention can also be employed for use in sense or antisense suppression of one or more Rac genes in a host cell, tissue, or plant. Attachment of chemical agents which bind, intercalate, cleave and/or crosslink to the isolated nucleic acids of the present invention can also be used to modulate transcription or translation. Further, using a primer specific to an insertion sequence (e.g., transposon) and a primer which specifically hybridizes to an isolated nucleic acid of the present invention, one can use nucleic acid amplification to identity insertion sequence inactivated Rac genes from a cDNA library prepared from insertion sequence mutagenized plants. Progeny seed from the plants comprising the desired inactivated gene can be grown to a plant to study the phenotypic changes characteristic of that inactivation. See, *Tools to Determine the Function of Genes*, 1995 Proceedings of the Fiftieth Annual Corn and Sorghum Industry Research Conference, American Seed Trade Association, Washington, D.C., 1995. Additionally, non-translated 5' or 3' regions of the polynucleotides of the present invention can be used to modulate turnover of heterologous mRNAs and/or protein synthesis. Further, the codon preference characteristic of the polynucleotides of the present invention can be employed in heterologous sequences, or altered in homologous or heterologous sequences, to modulate translational level and/or rates.

The present invention also provides isolated proteins comprising polypeptides including an amino acid sequence from the Rac polypeptides (e.g., preproenzyme, proenzyme, or enzymes) as disclosed herein. The present invention also provides proteins comprising at least one epitope from a Rac polypeptide. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, or for purification of Rac polypeptides.

The isolated nucleic acids of the present invention can be used over a broad range of plant types, including species from the genera Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea, and Populus.

Pathogens of the invention include, but are not limited to, viruses or viroids, bacteria, insects, fungi, and the like. Viruses include tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotrichum. truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphaniderrnatum, Pythium ultimum, Pythium debaryanum,* Tomato spotted wilt virus, *Heterodera glycines Fusarium solani;* Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis,* Fusar-atrum, *Xanthomonas campestris* p.v. *alfalfae, Aphanomyces euteiches, Stemphylium herbarum, Stemphylium alfalfae;* Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* p.v. *Carotovora, Cephalosporium acremonium, Phytophthora cryptogea, Albugo tragopogonis,* Maize: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatie-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganese* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* p.v. Zea, *Erwinia corotovora,* Cornstunt spiroplasma, *Diplodia macrospora, Sclerophthora macrospora, Peronosclerospora sorghi, Peronosclerospora philippinesis, Peronosclerospora maydis, Peronosclerospora sacchari, Spacelotheca reiliana, Physopella zeae, Cephalosporium maydis, Caphalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternate, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nucleic Acids

The present invention provides, inter alia, isolated nucleic acids of RNA, DNA, and analogs and/or chimeras thereof, comprising a Rac polynucleotide encoding such enzymes as:

(a) a polynucleotide encoding a Rac polypeptide of SEQ ID NOS: 2, 4, 6, 8, 10, 16, 18, 20, 22, 24, 26, 28, 30, 32 and 34, and conservatively modified and polymorphic variants thereof, including exemplary polynucleotides of SEQ ID NOS: 1, 3, 5, 7, 9, 15, 17, 19, 21, 23, 25, 27, 29, 31, and 33;

(b) a polynucleotide which selectively hybridizes to a polynucleotide of (a);

(c) a polynucleotide having at least 64% sequence identity with polynucleotides of (a) or (b);

(d) a polynucleotide encoding a protein having a specified number of contiguous amino acids from a prototype polypeptide;

(e) complementary sequences of polynucleotides of (a), (b), (c), or (d); and (f) a polynucleotide comprising at least 25 contiguous nucleotides from a polynucleotide of (a), (b), (c), (d), or (e).

Plasmids containing the polynucleotide sequences of the invention were deposited with American Type Culture Collection (ATCC), Manassas, Va., and assigned Accession Nos. 98796, 98797, 98798, 98799, and 98800. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. § 112.

A. Polynucleotides Encoding A Polypeptide of the Present Invention or Conservatively Modified or Polymorphic Variants Thereof As indicated in (a), supra, the present invention provides isolated heterologous nucleic acids comprising a Rac polynucleotide, wherein the polynucleotide encodes a Rac polypeptide, disclosed herein in SEQ ID NOS: 2, 4, 6, 8, 10, 16, 18, 20, 22, 24, 26, 28, 30, 32, and 34, or conservatively modified or polymorphic variants thereof. Those of skill in the art will recognize that the degeneracy of the genetic code allows for a plurality of polynucleotides to encode for the identical amino acid sequence. Such "silent variations" can be used, for example, to selectively hybridize and detect allelic variants of polynucleotides of the present invention. Accordingly, the present invention includes polynucleotides of SEQ ID NOS: 1, 3, 5, 7, 9, 15, 17, 19, 21, 23, 25, 27, 29, 31, and 33, and silent variations of polynucleotides encoding a polypeptide of SEQ ID NOS: 2, 4, 6, 8, 10, 16, 18, 20, 22, 24, 26, 28, 30, 32, and 34. The present invention further provides isolated nucleic acids comprising polynucleotides encoding conservatively modified variants of a polypeptide of SEQ ID NOS: 2, 4, 6, 8, 10, 16, 18, 20, 22, 24, 26, 28, 30, 32, and 34. Conservatively modified variants can be used to generate or select antibodies immunoreactive to the non-variant polypeptide. Additionally, the present invention further provides isolated nucleic acids comprising polynucleotides encoding one or more polymorphic (allelic) variants of polypeptides/polynucleotides. Polymorphisms are frequently used to follow segregation of chromosomal regions in, for example, marker assisted selection methods for crop improvement.

B. Polynucleotides Amplified from a *Zea mays* Nucleic Acid Library

As indicated, the present invention provides isolated nucleic acids comprising Rac polynucleotides, wherein the polynucleotides are amplified from a *Zea mays* nucleic acid library. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). The nucleic acid library may be a cDNA library, a genomic library, or a library generally constructed from nuclear transcripts at any stage of intron processing. Generally, a cDNA nucleic acid library will be constructed to comprise a majority of full-length cDNAs. Often, cDNA libraries will be normalized to increase the representation of relatively rare cDNAs. In preferred embodiments, the cDNA library is constructed using a full-length cDNA synthesis method. Examples of such methods include Oligo-Capping (Maruyama, et al., *Gene*, 138: 171–174 (1994)), Biotinylated CAP Trapper (Carninci, et al., *Genomics*, 37: 327–336 (1996)), and CAP Retention Procedure (Edery, et al., *Molec and Cellular Bio* 15: 3363–3371 (1995). CDNA synthesis is preferably catalyzed at 50–55 degree Celsius to prevent formation of RNA secondary structure. Examples of reverse transcriptases that relatively stable at these temperatures are SuperScript II Reverse Transcriptase (Life Technologies, Inc.), AMV Reverse Transcriptase (Boehringer Mannheim) and RetroAmp Reverse Transcriptase (Epicentre). Rapidly growing tissues, or rapidly dividing cells are preferably used as sources.

The present invention also provides subsequences of full-length nucleic acids. Any number of subsequences can be obtained by reference to SEQ ID NOS: 1, 3, 5, 7, and 9, and using primers which selectively amplify, under stringent conditions to: at least two sites to the polynucleotides of the present invention, or to two sites within the nucleic acid which flank and comprise a polynucleotide of the present invention, or to a site within a polynucleotide of the present invention and a site within the nucleic acid which comprises it. A variety of methods for obtaining 5' and/or 3' ends is well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego, 1990), pp. 28–38.); see also, U.S. Pat. No. 5,470,722, and *Current Protocols in Molecular Biology*, Unit 15.6, Ausubel, et al., Eds., Greene Publishing and Wiley-Interscience, New York (1995). Thus the present invention provides Rac polynucleotides having the sequence of the Rac gene, nuclear transcript, cDNA, or complementary sequences and/or subsequences thereof.

Primer sequences can be obtained by reference to a contiguous subsequence of a polynucleotide of the present invention. Primers are chosen to selectively hybridize, under PCR ampification conditions, to a polynucleotide of the present invention in an amplification mixture comprising a genomic and/or cDNA library from the same species. Generally, the primers are complementary to a subsequence of the amplicon they yield. In some embodiments, the primers will be constructed to anneal at their 5' terminal end's to the codon encoding the carboxy or amino terminal amino acid residue (or the complements thereof) of the polynucleotides of the present invention. The primer length in nucleotides is selected from the group of integers consisting of from at least 15 to 50. Thus, the primers can be at least 15, 18, 20, 25, 30, 40, or 50 nucleotides in length. A non-annealing sequence at the 5'end of the primer (a "tail") can be added, for example, to introduce a cloning site at the terminal ends of the amplicon.

The amplification primers may optionally be elongated in the 3' direction with additional contiguous nucleotides from the polynucleotide sequences, such as SEQ ID NOS: 1, 3, 5, 7, and 9, from which they are derived. The number of nucleotides by which the primers can be elongated is selected from the group of integers consisting of from at least 1 to 25. Thus, for example, the primers can be elongated with an additional 1, 5, 10, or 15 nucleotides. Those of skill will recognize that a lengthened primer sequence can be employed to increase specificity of binding (i.e., annealing) to a target sequence.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes which are specific to a polypeptide of the present invention. Methods for protein synthesis from PCR derived templates are known in the art and available commercially. See, e.g., Amersham Life Sciences, Inc, Catalog 1997, p.354.

C. Polynucleotides Which Selectively Hybridize to a Polynucleotide of (A) or (B)

As indicated in (c), supra, the present invention provides isolated nucleic acids comprising Rac polynucleotides, wherein the polynucleotides selectively hybridize, under selective hybridization conditions, to a polynucleotide of paragraphs (A) or (B) as discussed, supra. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated from a Zea mays nucleic acid library. Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having at Least 60% Sequence Identity with the Polynucleotides of (A), (B) or (C)

As indicated in (d), supra, the present invention provides isolated nucleic acids comprising Rac polynucleotides, wherein the polynucleotides have a specified identity at the nucleotide level to a polynucleotide as disclosed above in paragraphs (A), (B), or (C). The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90%, or 95%.

Optionally, the polynucleotides of this embodiment will share an epitope with a polypeptide encoded by the polynucleotides of (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment embrace nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Nos. 91/17271, 91/18980, 91/19818, and 93/08278. Other systems for generating libraries of peptides have aspects of both in vitro chemical synthesis and recombinant methods. See, PCT Patent publication Nos. 92/05258, 92/14843, and 96/19256. See also, U.S. Pat. Nos. 5,658,754; and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and is Cross-Reactive to the Prototype Polypeptide As indicated in (e), supra, the present invention provides isolated nucleic acids comprising Rac polynucleotides, wherein the polynucleotides encode a protein having a subsequence of contiguous amino acids from a prototype Rac polypeptide. Exemplary prototype Rac polypeptides are provided in SEQ ID NOS: 2, 4, 6, 8, 10, 16, 18, 20, 22, 24, 26, 28, 30, 32, and 34. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as, but not limited to, a polypeptide encoded by the polynucleotide of (b), supra, or exemplary polypeptides of SEQ ID NOS: 2, 4, 6, 8, 10, 16, 18, 20, 22, 24, 26, 28, 30, 32, and 34. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

F. Polynucleotides Complementary to the Polynucleotides of (A)–(E)

As indicated in (f), supra, the present invention provides isolated nucleic acids comprising Rac polynucleotides, wherein the polynucleotides are complementary to the polynucleotides of paragraphs A–E, above. As those of skill in the art will recognize, complementary sequences base-pair throughout the entirety of their length with the polynucleotides of (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides Which are Subsequences of the Polynucleotides of (A)–(F)

As indicated in (g), supra, the present invention provides isolated nucleic acids comprising Rac polynucleotides, wherein the polynucleotide comprises at least 25 contiguous bases from the polynucleotides of (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75, 100, 150, 200, 250, 300, 350, 400, 450, 500, 550, 600, 650, 700, 800, 900, or up to the full length of a maize Rac polynucleotide of contiguous nucleotides in length from the polynucleotides of (A)–(F). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The subsequences of the present invention can comprise structural characteristics of the sequence from which it is derived. Alternatively, the subsequences can lack certain structural characteristics of the larger sequence from which it is derived. For example, a subsequence from a polynucleotide encoding a polypeptide having at least one linear epitope in common with a prototype sequence, such as SEQ ID NOS: 2, 4, 6, 8 and 10, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In preferred embodiments the monocot is *Zea mays*. Particularly preferred is the use of *Zea mays* tissue.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is generally a vector, adapter, or linker for cloning and/or expression of a polynucleotide of the present invention. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pOPRSVI CAT, pOPI3 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, pGEX, lambda MOSSlox, and lambda MOSElox. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. While isolation of RNA, and construction of cDNA and genomic libraries is well known to those of ordinary skill in the art, the following highlights some of the methods employed.

A1. mRNA Isolation and Purification

Total RNA from plant cells comprises such nucleic acids as mitochondrial RNA, chloroplastic RNA, rRNA, tRNA, hnRNA and mRNA. Total RNA preparation typically involves lysis of cells and removal of proteins, followed by precipitation of nucleic acids. Extraction of total RNA from plant cells can be accomplished by a variety of means. Frequently, extraction buffers include a strong detergent such as SDS and an organic deanturant such as guanidinium isothiocyanate, guanidine hydrochloride or phenol. Following total RNA isolation, poly(A)$^+$ mRNA is typically purified from the remainder RNA using oligo(dT) cellulose. Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-lnterscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'–3' (Paoli, Pa.). See also, U.S. Pat. Nos. 5,614,391; and, 5,459,253. The mRNA can be fractionated into populations with size ranges of about 0.5, 1.0, 1.5, 2.0, 2.5 or 3.0 kb. The cDNA synthesized for each of these fractions can be size selected to the same size range as its mRNA prior to vector insertion. This method helps eliminate truncated cDNA formed by incompletely reverse transcribed mRNA.

A2. Construction of a cDNA Library

Construction of a cDNA library generally entails five steps. First, first strand cDNA synthesis is initiated from a poly(A)+ mRNA template using a poly(dT) primer or random hexanucleotides. Second, the resultant RNA-DNA hybrid is converted into double stranded cDNA, typically by a combination of RNAse H and DNA polymerase I (or Klenow fragment). Third, the termini of the double stranded cDNA are ligated to adaptors. Ligation of the adaptors will produce cohesive ends for cloning. Fourth, size selection of the double stranded cDNA eliminates excess adaptors and primer fragments, and eliminates partial cDNA molecules due to degradation of mRNAs or the failure of reverse transcriptase to synthesize complete first strands. Fifth, the cDNAs are ligated into cloning vectors and packaged. cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). cDNA synthesis kits are available from a variety of commercial vendors such as: Stratagene, and Pharmacia.

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13, or more kilobase pairs. Vectors to accommodate inserts of these sizes are known in the art and available commercially. See, e.g., Stratagene's lambda ZAP Express (cDNA cloning vector with 0 to 12 kb cloning capacity).

An exemplary method of constructing a greater than 95% pure full-length cDNA library is described by Carninci et al., *Genomics*, 37:327–336 (1996). In that protocol, the cap-structure of eukaryotic mRNA is chemically labeled with biotin. By using streptavidin-coated magnetic beads, only the full-length first-strand cDNA/mRNA hybrids are selectively recovered after RNase I treatment. The method provides a high yield library with an unbiased representation of the starting mRNA population. Other methods for producing full-length libraries are known in the art. See, e.g., Edery et al., *Mol. Cell Biol.*, 15(6):3363–3371 (1995); and, PCT Application WO 96/34981.

A3. Nonnalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented.

A number of approaches to normalize cDNA libraries are known in the art. One approach is based on hybridization to genomic DNA. The frequency of each hybridized cDNA in the resulting normalized library would be proportional to that of each corresponding gene in the genomic DNA. Another approach is based on kinetics. If cDNA reannealing follows second-order kinetics, rarer species anneal less rapidly and the remaining single-stranded fraction of cDNA becomes progressively more normalized during the course of the hybridization. Specific loss of any species of cDNA, regardless of its abundance, does not occur at any Cot value. Construction of normalized libraries is described in Ko, *Nucl. Acids. Res.*, 18(19):5705–5711 (1990); Patanjali et al., *Proc. Natl. Acad. U.S.A.*, 88:1943–1947 (1991); U.S. Pat. Nos. 5,482,685, and 5,637,685. In an exemplary method described by Soares et al., normalization resulted in reduction of the abundance of clones from a range of four orders of magnitude to a narrow range of only 1 order of magnitude. *Proc. Natl. Acad. Sci. USA*, 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybrdized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, *Technique*, 3(2):58–63 (1991); Sive and St. John, *Nucl. Acids Res.*, 16(22):10937 (1988); *Current Protocols in Molecular Biology*, Ausubel, et al., Eds., Greene Publishing and Wiley-Interscience, New York (1995); and, Swaroop et al., *Nucl. Acids Res.*, 19)8):1954 (1991). cDNA subtraction kits are commercially available. See, e.g., PCR-Select (Clontech).

A4. Construction of a Genomic Library

To construct genomic libraries, large segments of genomic DNA are generated by random fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques*, 22(3): 481–486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, supra.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.*, 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A number of promoters can be used in the practice of the invention. A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter (Christensen, et at. *Plant Mol Biol* 18, 675–689 (1992); Bruce, et at., *Proc Natl Acad Sci USA* 86, 9692–9696 (1989)), the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known to those of skill.

Where low level expression is desired, weak promoters will be used. It is recognized that weak inducible promoters may be used. Additionally, either a weak constitutive or a weak tissue specific promoter may be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompass promoters that are expressed in only a few cells and not in others to give a total low level of expression. Such weak constitutive promoters include, for example, the core promoter of the Rsyn7 (WO 97/44756), the core 35S CaMV promoter, and the like. Where a promoter is expressed at unacceptably high levels, portions of the promoter sequence can be deleted or modified to decrease expression levels. Additionally, to obtain a varied series in the level of expression, one can also make a set of transgenic plants containing the polynucleotides of the present invention with a strong constitutive promoter, and then rank the transgenic plants according to the observed level of expression. The transgenic plants will show a variety in performance, from high expression to low expression. Factors such as chromosomal position effect, cosuppression, and the like will affect the expression of the polynucleotide.

Alternatively, the plant promoter can direct expression of a polynucleotide of the present invention under environmental control. Such promoters are referred to here as "inducible" promoters. Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light. Examples of pathogen-inducible promoters include those from proteins, which are induced following infection by a pathogen; e.g., PR proteins, SAR proteins, beta-1,3-glucanase, chitinase, etc. See, for example, Redolfi, et al., *Neth J. Plant Pathol.* 89:245–254 (1983); Uknes, et al., *The Plant Cell* 4:645–656 (1992); Van Loon, *Plant Mol. Virol.* 4:111–116 (1985); copending U.S. application Ser. No. 60/076,100, filed Feb. 26, 1998; and copending U.S. application Ser. No. 60/079, 648, filed Mar. 27, 1998.

Of interest are promoters that are expressed locally at or near the site of pathogen infection. See, for example, Marineau, et al., *Plant Mol Biol* 9:335–342 (1987); Matton, et al., *Molecular Plant-Microbe Interactions* 2:325–342 (1987); Somssich et al., *Proc Natl Acad Sci USA* 83:2427–2430 (1986); Somssich et al., *Mole Gen Genetics* 2:93–98 (1988); Yang, *Proc Natl Acad Sci USA* 93:14972–14977. See also, Chen, et al., *Plant J* 10:955–966 (1996); Zhang and Sing, *Proc Natl Acad Sci USA* 91:2507–2511 (1994); Warner, et al., *Plant J* 3:191–201 (1993); and Siebertz, et al., *Plant Cell* 1:961–968 (1989), all of which are herein incorporated by reference. Of particular interest is the inducible promoter for the maize PRms gene, whose expression is induced by the pathogen *Fusarium moniliforme* (see, for example, Cordero, et al., *Physiol Molec Plant Path* 41:189–200 (1992) and is herein incorporated by reference.

Additionally, as pathogens find entry into plants through wounds or insect damage, a wound inducible promoter may be used in the constructs of the invention. Such wound inducible promoters include potato proteinase inhibitor (pin II) gene (Ryan, *Annu Rev Phytopath* 28:425–449 (1990); Duan, et a., *Nat Biotech* 14:494–498 (1996)); wun1 and wun 2, U.S. Pat. No. 5,428,148; win1 and win2 (Stanford, et al., *Mol Gen Genet* 215:200–208 (1989)); systemin (McGurl, et al., *Science* 225:1570–1573 (1992)); WIP1 (Rohmeier, et al., *Plant Mol Biol* 22:783–792 (1993); Eckelkamp, et al., *FEB Letters* 323:73–76 (1993)); MPI gene (Corderok, et al., *The Plant J* 6(2):141–150(1994)); and the like, herein incorporated by reference.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and gamma-zein promoter. An exemplary promoter for leaf- and stalk-preferred expression is MS8–15 (WO 98/00533). Examples of seed-preferred promoters included, but are not limited to, 27 kD gamma zein promoter and waxy promoter (Boronat, et al., *Plant Sci*, 47:95–102 (1986); Reina, et al., *Nucleic Acids Res* 18(21):6426 (1990); and Kloesgen, et al., *Mol Gen Genet* 203: 237–244 (1986)). Promoters that express in the embryo, pericarp, and endosperm are disclosed in U.S. applications Ser. Nos. 60/097,233 filed Aug. 20, 1998 and 60/098,230 filed Aug. 28, 1998, both of which are hereby incorporated by reference. The operation of a promoter may also vary depending on its location in the genome. Thus, a developmentally regulated promoter may become fully or partially constitutive in certain locations. A developmentally regulated promoter can also be modified, if necessary, for weak expression.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea mays*, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8: 4395–4405 (1988); Callis et al., *Genes Dev.* 1: 1183–1200 (1987). Such intron enhancement of gene expression is typically greatest when placed near the 5' end of the transcription unit. Use of maize introns Adhl-S intron 1, 2, and 6, the Bronze-1 intron are known in the art. See generally, *The Maize Handbook*, Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., Meth. in Enzymol., 153:253–277 (1987). These vectors are.plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., Gene, 61:1–11 (1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to gene expression in plants. To accomplish this, a nucleic acid segment from the desired gene is cloned and operably linked to a promoter such that the anti-sense strand of RNA will be transcribed. The construct is then transformed into plants and the anti-sense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci.* (USA) 85: 8805–8809 (1988); and Hiatt et al., U.S. Pat. No. 4,801,540.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2: 279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., Nature 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Proteins

The isolated proteins of the present invention comprise a polypeptide having at least 10 amino acids encoded by any one of the polynucleotides of the present invention as discussed more fully, supra, or polypeptides which are conservatively modified variants thereof. Exemplary polypeptide sequences are provided in SEQ ID NOS: 2, 4, 6, 8, 10, 16, 18, 20, 22, 24, 26, 28, 30, 32, and 34. The proteins of the present invention or variants thereof can comprise any number of contiguous amino acid residues from a polypeptide of the present invention, wherein that number is selected from the group of integers consisting of from 10 to the number of residues in a full-length Rac polypeptide. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

As those of skill will appreciate, the present invention includes catalytically active polypeptides of the present invention (i.e., enzymes). Catalytically active polypeptides have a specific activity at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention encoded by a polynucleotide of the present invention as described, supra. Exemplary polypeptides include those which are full-length, such as those disclosed in SEQ ID NOS: 2, 4, 6, 8, 10, 16, 18, 20, 22, 24, 26, 28, 30, 32, and 34. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of- the present invention for such exemplary utilities as immunoassays or protein purification techniques (see for example, SEQ ID NOS: 11–14).

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A. Expression in Prokaryotes

Prokaryotic cells may be used as hosts for expression. Prokaryotes most frequently are represented by various strains of E. coli; however, other microbial strains may also be used. Conmmonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in E. coli is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva, et al., Gene 22: 229–235 (1983); Mosbach, et al., Nature 302: 543–545 (1983)).

B. Expression in Eukaryotes

A variety of eukaryotic expression systems such as yeast, insect cell lines, plant and mammalian cells, are known to those of skill in the art. As explained briefly below, the polynucleotides of the present invention can be expressed in these eukaryotic systems. In some embodiments, transformeditransfected plant cells, as discussed infta, are employed as expression systems for production of the proteins of the instant invention.

Synthesis of heterologous proteins in yeast is well known. Sherman, F., et al., *Methods in Yeast Genetics*, Cold Spring Harbor Laboratory (1982) is a well recognized work describing the various methods available to produce the protein in yeast. Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., Gene 8: 17–24 (1979); Broach, et al., Gene 8: 121–133 (1979)).

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89: 49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See Schneider, *J. Embryol. Exp. Morphol.* 27: 353–365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach*, D. M. Glover, Ed., IRL Press, Arlington, Va. pp. 213–238 (1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method, which provides for efficient transformation/transfection, may be employed.

A. Plant Transformation

The genes of the present invention can be used to transform any plant. In this manner, genetically modified plants, plant cells, plant tissue, seed, and the like can be obtained. Transformation protocols may vary depending on the type of plant cell, i.e. monocot or dicot, targeted for transformation. Suitable methods of transforming plant cells include microinjection (Crossway et al. (1986) Biotechniques 4:320–334), electroporation (Riggs et al (1986) *Proc. Natl. Acad. Sci. USA* 83:5602–5606, Agrobacterium mediated transformation (Hinchee et al. (1988) *Biotechnology* 6:915–921), direct gene transfer (Paszkowski et al (1984) *EMBO J.* 3:2717–2722), and ballistic particle acceleration (see, for example, Sanford et al. U.S. Pat. No. 4,945,050; Tomes et al. "Direct DNA Transfer into Intact Plant Cells via Microprojectile Bombardment" In Gamborg and Phillips (Eds.) *Plant Cell, Tissue and Organ Culture: Fundamental Methods*, Springer-Verlag, Berlin (1995); and McCabe et al. (1988) *Biotechnology* 6:923–926). Also see, Weissinger et al. (1988) *Annual Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes et al. "Direct DNA Transfer into Intact Plant Cells via Microprojectile Bombardment" In Gamborg and Phillips (Eds.) *Plant Cell, Tissue and Organ Culture: Fundamental Methods*, Springer-Verlag, Berlin (1995) (maize); Klein et al. (1988) *Plant Physiol.* 91:440–444 (maize) Fromm et al. (1990) *Biotechnology* 8:833–839 (maize); Hooydaas-Van Slogteren & Hooykaas (1984) *Nature* (London) 311:763–764; Bytebier et al. (1987) *Proc. Natl. Acad. Sci. USA* 84:5345–5349 (Liliaceae); De Wet et al. (1985) In *The Experimental Manipulation of Ovule Tissues* ed. G. P. Chapman et al. pp. 197–209. Longman, N.Y. (pollen); Kaeppler et al. (1990) *Plant Cell Reports* 9:415–418; and Kaeppler et al. (1992) *Theor. Appl. Genet.* 84:560–566 (whisker-mediated transformation); D'Halluin et al. (1992) *Plant Cell* 4:1495–1505 (electroporation); LI et al. (1993) *Plant Cell Reports* 12:250–255 and Christou and Ford (1995) *Annals of Botany* 75:745–750 (maize via *Agrobacterium tumefaciens*); all of which are herein incorporated by reference.

The cells, which have been transformed, may be grown into plants in accordance with conventional ways. See, for example, McCormick et al. (1986) *Plant Cell Reports*, 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved. One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non- transgenic plant are also contemplated.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Synthesis of Proteins

The proteins of the present invention can be constructed using noncellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology. Vol*, 2. *Special Methods in Peptide Synthesis, Part A*.; Merrifield, et al., *J. Am. Chem. Soc.* 85: 2149–2156 (1963), and *Stewart et al., Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Modulating Rac Content and/or Composition

The present invention further provides a method for modulating (i.e., increasing or decreasing) Rac content or composition in a plant or part thereof. Modulation can be effected by increasing or decreasing the Rac content (i.e., the total amount of Rac) and/or the Rac composition (the ratio of various Rac monomers in the plant) in a plant. The method comprises transforming a plant cell with a recombinant expression cassette comprising a polynucleotide of the present invention as described above to obtain a transformed plant cell, growing the transformed plant cell under plant forming conditions, and inducing expression of a polynucleotide of the present invention in the plant for a time sufficient to modulate Rac content and/or composition in the plant or plant part.

In some embodiments, disease resistance in a plant may be modulated by altering, in vivo or in vitro, the promoter of a non-isolated Rac gene to up- or down-regulate gene expression. In some embodiments, the coding regions of native Rac genes can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate Rac content and/or composition in the plant. Plant forming conditions are well known in the art and discussed briefly, supra.

In general, content or composition is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, disease resistance is modulated in monocots, particularly maize.

Molecular Markers

The present invention provides a method of genotyping a plant comprising a polynucleotide of the present invention. Preferably, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H.

Paterson 1996 (Chapter 2) in: Genome Mapping in Plants (ed. Andrew H. Paterson) by Academic Press/R. G. Landis Company, Austin, Tex., pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a Rac gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a Rac gene.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or Pst I genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the E. coli mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTR's and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.* 15:8125 (1987)) and the 5<G>7 methyl GpppG cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. 96/19256. See also, Zhang, J. H., et al. *Proc. Natl. Acad. Sci. USA* 94:4504–4509 (1997) and Zhao, et al., *Nature Biotech* 16:258–261 (1998). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a change in $K_m$ and/or $K_{cat}$ over the wild-type protein as provided herein. In other embodiments, a protein or polynculeotide generated from sequence shuffling will have a ligand binding affinity greater than the non-shuffled wild-type polynucleotide. The increase in such properties can be at least 110%, 120%, 130%, 140% or 150% of the wild-type value.

Use of the Rac Genes and Proteins in Plant Disease Resistance

The present invention relates to the use of Rac polypeptide and polynucleotide sequences in controlling plant disease. Cytoskeletal modifications in host cells are closely associated with pathogen attack. It is known that Rac-related proteins mediate cytoskeletal reorganization in response to various stimuli. Thus, it is possible that Rac-related proteins play an important role during a disease response by altering the cytoskeleton reorganization. In fact, CDC42 protein was shown to be required for Salmonella induced cytoskeletal and nuclear responses (Chen el. al., *Science* 274:2115–2118 (1996)). It is possible that similar mechanisms might be operating in plant cells undergoing pathogen attack.

Thus the present invention is useful in protecting plants from pathogens. Once a plant is transformed with a polynucleotide sequence encoding a Rac polypeptide, expression of the polypeptide in the plant confers resistance to infection by plant pathogens. There are at least two different modes of action of the Rac genes which can confer disease resistance: 1) altering levels of reactive oxygen species or 2) by modulation of the signal transduction pathway responsible for turning on the MAP kinase cascade. The MAP kinase cascade is responsible for activating many cellular processes including defense gene expression, and cell division.

The oxidative burst, a rapid, production of ROS (reactive oxygen species) is one of the earliest observable aspects of a plant's defense strategy. ROS play a central role in disease resistance by directly killing the invading pathogens and by regulating a number of biochemical events during pathogen attack. These biochemical events include the production of antimicrobial compounds called phytoalexins, systemic acquired resistance, immobilization of plant cell wall proteins, changes in ion fluxes, induction of defense-related gene expression and initiation of localized programmed cell death also termed "hypersensitive response" (HR). In fact increased production of ROS in transgenic plants by overexpression of glucose oxidase and oxalate oxidase has been shown to confer disease resistance phenotype in plants (Wu, et al., *Plant Cell*, 7: 1357–1368 (1995) and U.S. Pat. No. 5,516,671, filed on Nov. 3, 1994; PCT publication No. WO 92/14824, published in Sep. 3, 1992 and PCT publication No. WO 92/15685 published in Sep. 17, 1992). The activation of Rac proteins and the associated induction of NADPH oxidase activity has been shown to be correlated with a hypersensitivity response during a resistance response (Xing, et al., *The Plant Cell*, 9: 249–259 (1997); Kieffer, et al., *FEBS Let*, 403: 149–153 (1997)). Transgenic plants expressing dominant (+) forms of the Rac genes can generate a high level of ROS and consequently will display enhanced resistance to pathogens.

It has been shown in yeast, and mammalian cell systems that Rac/Rho proteins are regulators of stress activated MAP kinase cascade. In plants, MAP kinases are important for mediating defense gene expression in response to wounding, salicylic acid, jasmonic acid, ethylene, pathogen-derived elicitors and other abiotic stresses. Thus by extending the analogy between plants and other systems, it is predicted that Rac proteins will be proven to be important regulators of MAP kinase cascades and associated defense gene expression in response to environmental stresses. (Zhang, et al., *The Plant Cell* 10:435–449 (1998))

Improving Transformation Efficiency

As described earlier, one common method of plant transformation is the biolistic method. Unfortunately, to get the foreign DNA into the plant cell, the cell is often wounded and frequently dies. Any method that prevents cell death, will increase the transformation rate of the plant cell by allowing plant cells containing foreign DNA to survive. The present invention, by inducing the defense gene response, prevents cell death and therefore improving transformation efficiency. By "improving transformation efficiency" is intended that the number of transformed plants recovered by a transformation event is increased. Generally, the number of transformed plants recovered is increased at least two-fold, preferably at least five-fold, more preferably at least ten-fold.

There is evidence to support that Rac/Rho control signal transduction pathways are essential for cell growth. When microinjected into quiescent fibroblasts, Rac/Rho proteins stimulated cell cycle progression and subsequent DNA synthesis (Olson, et al., *Science*, 269: 1270–1272 (1995). Overexpression of RacA dominant (−) version in maize cells resulted in multinucleate phenotype, suggesting a role for RacA in cell division/cytokinesis (see Example 5). Regulation of the cell cycle is of immense importance to increase the transformation efficiency in corn. Factors that induce cell division should positively improve the number of transformation events.

Thus, plant tissue expressing the Rac genes of the present invention either stably or transiently would improve transformation efficiency. In order to express the Rac genes, the genes would be incorporated into a expression vector and co-introduced with the gene of interest. Alternatively, the Rac gene can be previously incorporated into the plant tissue either stably or transiently and then the gene of interest introduced. The preferable method is to introduce the dominant positive version of a Rac gene (SEQ ID NOS: 15, 17, 19, or 21) into the plant tissue.

By altering the expression of the Rac genes of the present invention, the level of ROI can be manipulated to increase cell viability or induce cell death. Methods of altering levels of expression are well known in the art, for example, using a weak constitutive promoter, a tissue specific promoter, a pathogen-inducible promoter or a developmentally regulated promoter, see also the section in the present application entitled "Recombinant Expression Cassettes". The emerging data suggests that the downstream effects of Rac genes on cell growth depends on the intensity of the Rac induced signal and the tissue type. For example, in mammalian cells high level of signal causes apoptosis, while low level of signal has anti-apoptotic effects (Dafna Bar-Sagi, Keystone symposia on "Specificity in Signal Transduction", 1998). Thus, by fine tuning the Rac expression in transgenic tissue and organisms, one can either stimulate or inhibit cell growth.

Regulating Programmed Cell Death

Programmed cell death is an integral step during development and in response to environmental stress conditions. It has been shown that overexpression of dominant positive Rac proteins in transgenic mice results in cell death in a tissue-specific manner (Lores, et al., *Oncogene*, 15: 601–605 (1997)). The sequences of the invention are also useful for genetically targeted cell ablations. In this manner, dominant negative nucleotide sequences can be utilized for cell ablation by expressing such negative nucleotide sequences with specific tissue promoters. For example, stamen promoters can be utilized to drive the negative alleles to achieve male sterile plants. (See, for example, DPA0344029 and U.S. Pat. No. 5,470,359, herein incorporated by reference). In this manner, very specific or general patterns of cell ablations can be created. Additionally, to provide specific cell ablation, antisense oligonucleotides for Rac or other genes of the invention can be expressed in target cells disrupting the translation, which produces the cell death suppressor proteins.

Regulation of Cytoskeleton Reorganization

Rac proteins are known to control cytoskeleton organization in diverse organisms. Furthermore, in plants, Rac-related proteins have been co-localized with actin distribution during pollen tube growth (Lin et al., *Plant Cell* 9: 1647–1659 (1997)). Expression of another Rac-related gene (cdc42) was shown to be essential for cytoskeleton reorganization and defense against bacterial attack (Dutartre, et al., *J of Cell Science* 109: 367–377 (1996); Nobles, et al., *Cell* 81: 53–62 (1995)). These results strongly suggest that Rac proteins play a very important role in regulating cytoskeleton organization during plant development and under stress conditions. Therefore, modulation the expression of a maize Rac polynucleotide in transgenic plants can be used to alter the cytoskeletal response during development or under stress conditions. For example, regulation of the pollen tube growth can increase or decrease male fertility. By transforming a Rac gene of the present invention operably linked to the appropriate tissue specific promoter one can alter pollen tube growth. A transgenic plant containing the desired traits and expressing the Rac gene in a tissue specific manner, would be able to out compete other non-transgenic pollen, containing non-desirable traits, and fertilize the ovum, thus improving the number of transgenic progeny.

Although the present invention has been described in some detail by way of illustration and example for purposes of clarity of understanding, it will be obvious that certain changes and modifications may be practiced within the scope of the appended claims.

EXAMPLE 1

This example describes the construction cDNA libraries.

Total RNA Isolation

Total RNA was isolated from maize tissues with TRIzol Reagent (Life Technology Inc. Gaithersburg, Md.) using a modification of the guanidine isothiocyanate/acid-phenol procedure described by Chomczynski and Sacchi [Chomczynski, P., and Sacchi, *N. Anal. Biochem.* 162, 156 (1987)]. In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+ RNA Isolation

The selection of poly(A)+ RNA from total RNA was performed using PolyATact system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.

cDNA Library Construction cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites.

EXAMPLE 2

This example describes cDNA sequencing and library subtraction.

Sequencing Template Preparation

Individual colonies were picked and DNA was prepared either by PCR with M13 forward primers and M13 reverse primers, or by plasmid isolation. All the cDNA clones were sequenced using M13 reverse primers.

Q-bot Subtraction Procedure cDNA libraries subjected to the subtraction procedure were plated out on 22×22 cm$^2$ agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22×22 cm$^2$ nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., [in Molecular Cloning: A laboratory Manual, 2$^{nd}$ Edition). The following probes were used in colony hybridization:

1. First strand cDNA from the same tissue as the library was made from to remove the most redundant clones.
2. 48–192 most redundant cDNA clones from the same library based on previous sequencing data.
3. 192 most redundant cDNA clones in the entire corn EST database.
4. A Sal-A20 oligo nucleotide: TCG ACC CAC GCG TCC GM AAA AAA AAA AAA AAA AAA (SEQ ID NO: 51) removes clones containing a poly A tail but no cDNA.

5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

EXAMPLE 3

Identification and sequencing of Maize Rac cDNAs (A to E)

Five Rac homologues, designated RacA-E (SEQ ID NOS: 1, 3, 5, 7, and 9), were identified from the maize genomics database described above, based on their sequence homology to known Rac genes in other organisms. These cDNAs were completely sequenced on both strands by automated sequencing methods. Internal primers were designed and synthesized to walk through the cDNA sequences.

A GCG software package containing GAP, under default settings, was used to align the amino acid sequences of the four maize Rac proteins with Rac/Rho related proteins sequences in the public databases from other organisms including plants. The percent identity and similarity of the maize Rac A–E protein sequences compared to the Human Rac2 protein sequence can be found in Table 1. A comparison of the maize Racs A–E protein sequences with each other can be found in Table 2.

TABLE 1

BestFit "Similarity" and "Identity" Scores Between Human Rac2 and Maize RacA–E

|  | % Similarity | % Identity |
|---|---|---|
| RacA | 69.78 | 59.34 |
| RacB | 70.33 | 63.187 |
| RacC | 69.23 | 60.989 |
| RacD | 69.23 | 62.637 |
| RacE | 68.16 | 60.335 |

TABLE 2

% Similarity and Identity between Maize Rac proteins

|  | ZmRacA | ZmRacB | ZmRacC | ZmRacD | ZmRacE |
|---|---|---|---|---|---|
| ZmRacA | 100 | 88.78 (82.65)* | 82.72 (76.96)* | 88.27 (80.61)* | 84.73 (77.34)* |
| ZmRacB |  | 100 | 82.61 (75.00)* | 92.39 (90.36)* | 84.29 (77.49)* |
| ZmRacC |  |  | 100 | 82.20 (74.34)* | 87.44 (83.58)* |
| ZmRacD |  |  |  | 100 | 87.03 (80.54)* |

*Identity Scores in parenthesis

Motifs were found that defined the positions of G1-elements GXXXXGKS/T, G3-elements IWDTAGQ, G4-elements NKXD, G5 elements EXSA, and putative G2/effector regions.

From Table 1, it is clear that the maize Rac polypeptides at best have only 63.187% identity to the Human Rac2 gene. In comparing the maize Rac polypeptides, RacB and RacD showed the highest similarity (92.39%) and RacC and RacD show the lowest similarity (82.20%).

It has been shown that all regions known to be involved in GTP/GDP binding are conserved between plant Rac proteins and mammalian Ras proteins. In addition, it seems that the 3-dimensional structure of both Ras and Rac/Rho proteins is similar. The predicted secondary structures of plant Rac proteins and mammalian Ras proteins are also very similar. The primary structures of plant and mammalian Rac proteins exhibit a high level of similarity throughout the amino acid sequence, with loop 1, loop 4, loop 8, the effector region, the $\alpha_1$-, $\alpha_2$-helix, $\beta_3$-, $\beta_5$-sheet, as the most conserved regions (Winge, et al., supra). The deduced amino acid sequence of maize Rac proteins also revealed the presence of four sequence motifs G1, G3, G4 and G5 that are found to be conserved in the small GTP binding (SMG) protein superfamily (Borg, et al., *The Plant J*, 11(2): 237–250 (1997)). These motifs together are responsible for nucleotide binding and GTP hydrolysis. The maize Rac proteins also contain the characteristic G2 effector region, which is fairly conserved within each subfamily, but less so between different subfamilies. The C-terminus region of these proteins contain the most varied sequence. The CXXL motif at the C-terminus, was present in RacA, B, C and D, however only two amino acids were found to be present after a Cys residue in RacE. The CXXL motif is known to be required for isoprenylation and geranygeranylation of the C-terminal Cys residu. These modifications of the C-termini of Rac proteins are important for membrane localization. Rac proteins also contain a stretch of 6–8 amino acids just upstream of the CXXL motif which is highly basic and consists of lysine and arginine residues. This basic region at the C-terminus is also found in human Ki-Ras proteins and is reported to facilitate membrane anchoring (Winge, et al., supra)

EXAMPLE 4

Site-directed Mutagenesis and Cloning of the Mutated Rac

As discussed earlier, a single amino acid change in the Rac amino acid sequence can alter the ability of Rac to cycle between active and inactive states. A change of glycine to valine at residue 12 in the highly conserved mammalian Racs results in total loss of GTPase activity, so that when the mutant Rac binds GTP it stays activated permanently, in other words a dominant positive form of Rac. Conversely, changing residue 18 from threonine to alanine causes loss of ability to bind GTP and hence causes permanent inactivation of Rac, in other words a dominant negative form of Rac.

Transformer™ Site-Directed Mutagenesis Kit from Clontech was used to generate dominant positive (G to V) and dominant negative versions (T to N) of the RacA–D cDNAs.

The primers used to generate the dominant positive and dominant negative versions of RacA–D were:

RacA

CBPBE14RB_u5, to generate G to V mutation
TCACGGTCGGCGACGTGGCCGTGGGCAAG (SEQ ID NO: 35)
CBPBE14RB_u6, to generate T to N mutation
GCCGTGGGCAAGAACTGTATGCTCATC (SEQ ID NO: 36)
CBPBE14C_u7, for PCR cloning in P7770
GAATTCGGATCCACACGACACCATG-GCGTCCAGCGCCTCTCGGTTC (SEQ ID NO: 37)
CBPBE14C_d5, for PCR cloning in P7770
TCTAGAGTTAACACGACACTCAGGACT-TGAAGCATAGCATTTTTC (SEQ ID NO: 38)

RacB

CRCBS75Ru3, to generate G to V mutation
TCACGGTCGGGGACGTCGCCGTCGGCAAG (SEQ ID NO: 39)
CRCBS75Ru4, to generate T to N mutation
GCCGTCGGCAAGAACTGCATGCTCATC (SEQ ID NO: 40)
CRCBS75RC_u5, for PCR cloning in P7770
GAATTCGGATCCACACGACACCAT-GAGCGCGTCCAGGTTCATAAAG (SEQ ID NO: 41)
CRCBS75C_d1, for PCR cloning in P7770
TCTAGAGTTAACACGACACTCA-CAAAATGGAGCACGCCCCCCTCTG (SEQ ID NO: 42)

RacC

CGEVL32RB_u1, to generate G to V mutation
CACGGTCGGCGATGTGGCCGTCGGGAAGAC (SEQ ID NO: 43)
CGEVL32RB_u2, to generate T to N mutation
GCCGTCGGGAAGAACTGCATGCTCATCTGC (SEQ ID NO: 44)
CGEVL32C_u3, for PCR cloning in P7770
GAATTCGGATCCACACGACACCAT-GAGCGCGGCGGCAGCGGCGGCG (SEQ ID NO: 45)
CGEVL32C_d1, for PCR cloning in P7770
TCTAGAGTTAACACGACACTTACGATGT-GAAACATCCGCTTCCACAG (SEQ ID NO: 46)

RacD

CB1FL19RB_u5, to generate G to V mutation
GTCACCGTGGGGGACGTGGCCGTCGGAAAGAC (SEQ ID NO: 47)
CB1FL19RB_u6, to generate T to N mutation
GCCGTCGGAAAGAACTGCATGCTCATCTC (SEQ ID NO: 48) CB1FL19C_u7, for PCR cloning in P770
GAATTCGGATCCACACGACACCAT-GAGCGCGTCTCGGTTCATCAAG (SEQ ID NO: 49)
CB1FL19C_d5, for PCR cloning in P7770
TCTAGAGTTAACACGACACTTA-CAAAATGGTGCATCCCTTCTGCAC (SEQ ID NO: 50)

The mutated Racs were then cloned in a P7770 transformation vector containing the ubiquitin promoter (U.S. Pat. No. 5,683,439) operably linked to the Rac polynucleotide of interest and followed by a PinII terminator. Primers were designed to introduce BamH1 and HpaI sites at the 5' and 3' end of the open reading frames of the mutated Rac cDNAs. Subsequently, these were cloned in the BamHI-HpaI site of the plasmid P7770. This allowed the placement of mutant Rac ORFs under the control of the ubiquitin promoter.

EXAMPLE 5

Transient Gene Expression Assay Using Biolistic Particle Bombardment:

A transient gene expression assay, as described by Nelson, et al., *Transgenic Research*, 6: 233–244 (1997) and hereby incorporated by reference, was used to evaluate the ability of an introduced Rac gene, whose expression product would induce expression of an unknown resident resistance gene in a host plant cell, to confer a hypersensitive response within the host cell. In the method, a particle bombardment system was used to simultaneously introduce a construct comprising a reporter gene driven by a constitutive promoter and a construct comprising a Rac gene with its promoter into maize cells for the purpose of studying physiological processes, foremost amongst them the plant defense response.

In this example, the first construct comprised a ubiquitin promoter driving the expression of the reporter CRC fusion protein gene, which when expressed causes cells to turn red due to anthocyanin production. Other reporter genes, such as GUS, luciferase, or green fluorescent protein, can be used in this assay. Mature embryos were dissected from the kernels and co-bombarded with mutant Rac versions in P7770 and with a CRC reporter gene also in P7770, driven by the ubiquitin promoter. The number of red spots representing anthocyanin biosynthesis and transgenic events were counted under a dissecting microscope 48 hours after bombardment. If expression of the Rac gene causes a hypersensitive-type disease response involving cell death, or at the very least radically redirected gene expression, the expression of the reporter gene will be disrupted and the visible, anthocyanin-containing phenotypes is suppressed. A positive control for induction of a hypersensitive-type disease response involving cell death was done by co-bombarding with the ubi:CRC construct and a ubi:avrRxv construct. The avrRxv nucleotide sequence is published. (See Whalen, et al., *Mol. Plant Microb. Interact.* 6:616–627; Accession No. L20423) Expression of the avr-Rxv gene product causes interaction of that gene product with a resident maize resistance gene, termed Rxv, resulting in a hypersensitive-type disease response and subsequent suppression of the anthocyanin-containing phenotype.

The results of co-bombardment of the Rac genes with the ubi:CRC construct into embryos can be seen in Table 3.

TABLE 3

Functional testing of dominant (+) maize Rac mutants in embryo bombardment assay:

| Constructs | Exp. 1 (# of red spots) | Exp. 2 (# of red spots) | Exp. 3 (# of red spots) | Exp. 4 (# of re spots) |
|---|---|---|---|---|
| CRC alone | 8 | 35 | 110 | 31 |
| +RacA GV | 35 | ND | 324 | 270 |
| +RacB GV | 9 | ND | ND | ND |
| +RacC GV | 20 | ND | ND | ND |
| +RacD GV | 16 | 54 | 61 | ND |
| +RacA TN | ND | ND | ND | 78 |
| +avrRxv | ND | ND | 1 | 5 |

ND: not determined,
GV = dominant positive,
TN = dominant negative

As can be seen in Table 3, embryos bombarded with the dominant positive form of a Rac gene in almost all cases showed a greater number of red spots than the control. The most dramatic increase can be seen in the experiments with the dominant positive form of RacA GV.

Leaf tissue was also bombarded with the ubi::+RacA construct, and tested for changes in the expression of defense genes. Protein extracts were made from the bombarded leaf tissues and Western analysis was performed according to Towbin, et al., *Proc. Nat'l. Acad. Sci.* (USA), 76(9): 4350–4354 (1979); and Anderson, et al.,

*Electrophoresis*, 3(3): 135–142 (1982), and hereby incorporated by reference, using antisera raised against purified tobacco PR-1b, and chitinase. Leaf tissue bombarded with the ubi::+RacA construct showed significantly higher levels of both PR-1b and chitinase, as compared to control leaf tissue. Control leaf tissue was leaf tissue bombarded with the CRC construct and the P7770 vector without a Rac polypeptide.

In addition to embryo transformation and leaf bombardment, protoplast transformation was also performed. Polyethylene glycol method was used to transform protoplasts obtained from Hi II suspension cells (Lyznik, et al., *The Maize Handbook*, eds. Freeling and Walbot, Springer-Verlag, New York, Inc. (1994) and hereby incorporated by reference). Protoplast transformation efficiency was monitored by transforming an aliquot of the protoplast preparation with Ubi:GUS construct (PHP3953). In the experiment, $10^5$ protoplasts were used per transformation. Two days after transformation, the protoplast were fixed in glutaraldehyde and stained for nuclear stain (DAPI) and observed with a light microscope under UV illumination.

When observed two days after transformation, a number of protoplasts transformed with RacA (−) exhibited multinucleate phenotype. In contrast protoplasts transformed with RacA (+) or control plasmid contained only a single nucleus.

The results of the embryo bombardment and protoplast transformation clearly show that the Rac genes plays an important role in cell division, increasing the number of transformed cells and thus improving the number of transformation events. The leaf bombardment assay indicates that the Rac genes are also able to turn on defense related genes. A combination of increased cell number and improved cell viability result in a significant increase in transformation events. The dominant positive form of RacA is the construct best able to turn on the defense response and improve transformation efficiency.

EXAMPLE 6

ROS Measurements in Mammalian Cells

The mammalian NIH 3T3 cells were seeded on 35 mm plates at the density $0.3 \times 10^6$/plate (12–24 hours before transfection). Transient transfection was performed using the cationic-liposome-mediated transfection (DOTAP Liposomal Transfection Reagent from Boehringer Mannheim, Cat. # 1202 375). Four Rac-dominant positives [Rac A (G→V), Rac B (G→V), Rac C (G→V) and Rac D (G→V)] and their dominant negative counterparts [Rac A (T→N), Rac B(T→N), Rac C (T→N) and Rac D (T→N)] were subcloned in the mammalian expression vector pZeoSv2 (+/−) (Invitrogen) containing the SV40 promoter and transiently transfected into NIH 3T3 cells.

Five μg of the plasmid-containing Rac or mutated Racs was transfected/35 mm plate. The 5 μg of DNA was diluted to the concentration of 0.1 μg/μl (50 μl) with Hepes buffer (20 mM, pH 7.4) in a sterile reaction tube. In a separate sterile reaction tube, 30 μl DOTAP was mixed with Hepes buffer to the final volume of 100 μl. The nucleic acid solution (50 μl) was transferred to the reaction tube already containing the DOTAP in Hepes buffer (100 μl) and mixed with the transfection mixture by gently pipetting the mixture several times. The transfection mixture was then incubated for 15 min at room temp then mixed with the DOTAP/nucleic acid mixture with 1.5 ml DMEM medium (Dulbecco's Modified Eagle Medium, GIBCO-BRL # 10569–010) containing 10% Fetal Bovine Serum. The old culture medium was removed from the plate and new culture medium containing the DOTAP/nucleic acid mixture was added. The cells were incubated overnight (about 20 hours). On the second day, the media containing the mixture was removed and replaced by fresh culture medium and incubated for an additional 20–24 hours. On the third day, the culture medium was removed and replaced with culture medium containing 0.5% serum and incubated overnight (15–20 hours) for EPR spectroscopy assay.

For the EPR assay, the medium was removed and the cells were washed with 1×PBS (Phosphate Buffered Saline, GIBCO__BRL # 14200-075) treated with chelating agent (Chelex 100 Resin, from Bio-Rad Cat # 142-2822) to remove metal ions that may give false signals. The cells were collected using plastic scrapers in the presence of 1 ml of 1×PBS buffer and spun down at 1200 rpm, then resuspended in 250 μl of 1×PBS buffer. About 25–50 μl of the cell suspension was used for the EPR assay. The volume was brought up to 200 μl with 1×PBS buffer and the spin trap, DEPMPO [5-(diethoxyphosphory)-5-methyl-1-pyrroline N-oxide), was added to the final concentration, 100 mM (10) at 0.0 time. The samples were assayed in EPR spectroscopy at different time points (i.e. 2, 15, 30 and 60 minutes) upon the addition of the DEPMPO.

Previous studies showed that NIH 3T3 cells stably transformed with a constitutively active isoform of p21Ras (H-Ras $^{V12}$), produced large amounts of reactive oxygen species (Irani, et al. Science. 275: 1649–1652). Superoxide dismutase (SOD) quenched the observed signals, whereas catalase had no effect. This result suggested that the observed signals were attributable to $0.0_2$ trapping rather than to 0.0H derived from $H_2O_2$. Production of $0.0_2$ by NIH 3T3 stably transformed with H-Ras$^{V12}$ (A6 cells) was confirmed by a Lucigenin-enhanced chemiluminescence (LUCL) assay, which has specificity for $0.0_2$ (Gyllenhammar. J. Immunol Methods. 97(2):209–213, 1987) This $0.0_2$ production was suppressed by the expression of dominant negative isoforms of Ras or Rac1 as well as by treatment with farnesyl protein transferase (FPTase), which inhibits Ras-dependent transformation and results in morphological reversion of Ras-transformed cells (Kohl, et al. Science 260:1934–1937 (1993), This observation showed that $0.0_2$ in A6 cells is dependent on oncogenic Ras. The results also showed, Ras-transformed cells have the ability to progress through the cell cycle even under conditions of confluence and growth factors deprivation and these cells displayed a greater rate of DNA synthesis than the controls (Irani, supra). Treating cells with the antioxidant N-acetyl-L-cysteine (NAC) which inhibits DNA synthesis inhibited the Ras-induced mitogenic response of A6 cells. Furthermore, the mitogenic-activated protein kinase (MAPK) activity was decreased and c-Jun N-terminal kinase (JNK) was not activated in H-Ras-transformed cells. In conclusion, these results indicate that H-Ras$^{V12}$-induced transformation can lead to the production of $0.0_2$ through one or more pathways involving Rac1. The implication of a reactive oxygen species, probably $0.0_2$, as a mediator of Ras-induced cell cycle progression independent of MAPK and JNK (perhaps JAK/STAT pathway) suggests a possible mechanism for the effects of antioxidants against Ras-induced cellular transformation.

The transient expression of a constitutively active mutant of Rac1 (Rac1$^{V12}$) in NIH 3T3 cells leads to a significant increase in ROS as detected by electron paramagnetic resonance (EPR) spectroscopy and the spin trapping DEMPMPO [5-(diethoxyphosophory)-5-methyl-1-pyrroline N-oxide] (Farnsworth, et al. Mol. Cell. Biol. 11:4822–4829, 1991) however, the expression of a dominant-negative Rac1 mutant (Rac1$^{N17}$) inhibits the production of ROS in HIH 3T3 cells induced to produce ROS because Rac$^{N17}$ could act as a dominant inhibitor of endogenous Rac function. By analogy to N17 H-ras mutant, it is probably that Rac $^{N17}$ in its inactive conformation competitively inhibits the interaction of the normal endogenous counterparts with a guanine nucleotide exchange factor.

Using EPR, NIH 3T3 cells transiently transfected with the dominant positive plant Rac isoforms markedly increased the level of ROS production and the levels were much higher in Rac A and Rac D than Rac B. However, cells transfected with the matching dominant-negative isoforms had no detectable level of ROS as shown by EPR spectroscopy. These results suggest that the Rac gene has been conserved throughout evolution, such that the molecule would regulate the production of ROS in most cells and can transduce its signal pathway in mammals as well as in plants. This technique may be used as screening assay for selecting the Rac isoform that produce high level of ROS which may help to develop the disease resistant plants.

EXAMPLE 7

Production of Antibodies to the Rac genes

The immugen for antibody production was a MAP synthesized peptide as seen below. The immugen was injected into rabbits using standard techniques. The antibodies produced can be used for a variety of assays including an Elisa (see Butler (ed.), *Immunochemistry of Solid-Phase Immunoassay*, CRC Press, (1991), and hereby incorporated by reference) and Western blotting.

Zea mays Rac peptides for making antibodies.

RacA (SEQ ID NO: 11) SRKGCSMMNIFGGRKML
RacB (SEQ ID NO: 12) KAKKKKKVQRGACSIL
RacC (SEQ ID NO: 13) MKTSSNQSLRRYLCGSGC
RacD (SEQ ID NO: 14) KQKKRKKKVQKGCTIL

EXAMPLE 8

The Effect of Rac Expression on the Reorganization of the Actin Cytoskeleton

Microinjection of Rac1$^{V12}$ into fibroblasts induces membrane ruffling activity, a process that requires the reorganization of the actin cytoskeleton. (Ridley et al., *Cell* 70, 401–410 (1992)) Therefore, the experiment was performed to find out whether activated ZmRac could induce a similar response in Swiss 3T3 cells. Cells were transfected with ZmRacs (dominant-positive) or Rac1$^{V12}$ and stained with FITC-phalloidin, in order to study actin organization. FITC-phalloidin assay: Cells were fixed with 4% formaldehyde in PBS for 10 min, permeabilized with 0.1% Triton X-100 in PBS for 10 min, stained with 0.66 μM FITC-Phalloidin (Molecular Probes, Eugene, Oreg.), rinsed with PBS, mounted, and examined with a Nikon Eclipse 800 fluorescence microscope, at an excitation of 580 nm. (Crawford, et al., *J. Biol. Chem.* 271, 26863–26867 (1996), and herein incorporated by reference).

Rac1 $^{V12}$, and ZmRac B, C, and D, all induced membrane ruffles. ZmRac A (dominant positive) had no detectable effect on membrane ruffling.

Ruffle formation results from both de novo polymerization of actin filaments and reorganization of existing filaments at the cell edge, resulting in liquid phase pinocytosis. The Alexa-568-labeled actin incorporation into cells transfected with the plasmids encoding Rac1 or its maize homologues was measured using a flow cytometry assay. Actin turnover assay: Cells were rinsed with buffer (20 mM HEPES, pH 7.5, 138 mM KCl, 4mM MgCl$_2$, 3 mM EGTA), then incubated with the same buffer supplemented with 0.2% saponin and 1 μM Alexa-568-Actin (Molecular Probes, Eugene, Oreg.), for 5 min, at room temperature (Symons, et al., *J. Cell Biol.* 114, 503–513 (1991), and herein incorporated by reference). Then cells were gently rinsed with HEPES, treated with 0.25% Trypsin-EDTA for 3 min, then Trypsin Inhibiting Solution (Clonetics, San Diego, Calif.) was added in amounts sufficient to block Trypsin activity. The resuspended cells were analyzed in FACS Calibur flow cytometer (Beckton Dickinson Immunocytometry Systems, San Jose, Calif.).

It was found that Rac $^{V12}$ and activated ZmRac B, C, and D induced G-actin incorporation, while ZmRac A (dominant-positive) had no detectable effect on actin incorporation. The dominant negative isoforms of ZmRacs and Rac1$^{N17}$ had no significant effect on actin uptake nor ruffle formation. Lack of effect of ZmRac A (dominate positive) on actin incorporation was consistent with its inability to induce membrane ruffling which requires actin re-organization.

Swiss 3T3 transiently transfected with the activated ZmRac isoforms, as well as their dominant negative counterparts, showed no significant differences in [$^3$H] thymidine incorporation. The rate of apoptosis of cells transfected with ZmRacs was not altered either, as assessed by TUNEL assay and Annexin V staining. (Guido, et al., *AmJ.Pathol.* 146: 3–8, 1995 (1995), Gorczyca, et al. *Cancer Res.* 53, 1945–1951 (1993), Martin, et al., *J. Exp. Med.* 182, 1545–1556 (1995)).

Although not intending to be limited by theory, the results suggest that activated ZmRac A and ZmRac D can be used as strong activators of the oxidative burst and to promote the defense response of plants against infectious agents. Furthermore, the structure of the Rac gene has been highly conserved throughout evolution, such that a maize Rac gene product is capable of regulating the generation of superoxide in mammalian cells. This effect of Rac seems remarkably conserved, and suggests that the Rac binding domain of superoxide generating enzyme complex must be also highly conserved. Other functions of Racs, such as the regulation of the actin cytoskeleton appear more selective. The results also support that the G2 region (amino acids 26–45), which is highly conserved between plants and animals, could be essential for ROS production. In contrast it was not found that the insert region (amino acids 124–135) was needed for ROS generation, nor actin regulation. This region is not conserved in plant Racs, and therefore, does not seem to be required for ROS production. This observation confirms data obtained with a reconstituted system in vitro, where the insert region was found to be expandable for ROS production. However, other domains of Rac, and in particular the positively charged amino acids, Histidine 103 and Lysine 166, shown to be important for NADPH oxidase activation in vitro, are conserved in Rac1 and ZmRacs, although, Histidine 103 of ZmRac C is replaced with the positively charged amino acid Arginine. These conserved amino acids appeared to have a synergistic effect with the G2 region for ROS production. (Martin, et al., *Biochemistry* 37, 7147–7156 (1998)).

This approach for testing ZmRacs could be used as a screening assay for selecting the Rac isoforms and other conserved regulators of ROS production, which will help in revealing superoxide generating mechanisms in plants and eventually in the development of disease resistant transgenic plants.

The above examples are provided to illustrate the invention but not to limit its scope. Other variants of the invention will be readily apparent to one of ordinary skill in the art and are encompassed by the appended claims. All publications, patents, and patent applications cited herein are indicative of the level of those skilled in the art to which this invention pertains. All publications, patents, and patent applications are hereby incorporated by reference to the same extent as if each individual publication or patent application was specifically and individually indicated to be incorporated by reference.

What is claimed is:

1. An isolated polynucleotide selected from the group consisting of:
   (a) a polynucleotide consisting essentially of at least 25 contiguous bases of a polynucleotide selected from the group consisting of SEQ ID NOS:3, 5, 7, 9, 17, 19, 21, 23, 27, 29, 31, and 33; and
   (b) a polynucleotide consisting essentially of at least 50 contiguous bases of a polynucleotide selected from the group consisting of SEQ ID NOS: 1, 15, and 25.

2. An isolated nucleic acid comprising a polynucleotide selected from the group consisting of:
   (a) a polynucleotide encoding a polypeptide selected from the group consisting of SEQ ID NOS:2, 4, 6, 8, 10, 16, 18, 20, 22, 24, 26, 28, 30, 32, and 34;
   (b) a polynucleotide selected from the group consisting of SEQ ID NOS: 1, 3, 5, 7, 9, 15, 17, 19, 21, 23, 25, 27, 29, 31, and 33; and
   (c) a polynucleotide that is complementary to the polynucleotide of (a) or (b).

3. A recombinant expression cassette, comprising the nucleic acid molecule of claim 2 operably linked to a promoter.

4. The recombinant expression cassette of claim 3, wherein said nucleic acid is operably linked in antisense orientation to said promoter.

5. A host cell containing the recombinant expression cassette of claim 3.

6. The host cell of claim 5, wherein said host cell is selected from the group consisting of bacterial cells, yeast cells, plant cells, and mammalian cells.

7. A transgenic plant cell comprising the nucleic acid molecule of claim 2.

8. A transgenic plant comprising the nucleic acid molecule of claim 2.

9. A transgenic seed from the transgenic plant of claim 8.

10. The transgenic seed of claim 9, wherein the seed is from *Zea mays*.

11. An isolated nucleic acid molecule comprising a polynucleotide selected from the group consisting of:
    (a) a polynucleotide encoding a polypeptide that enhances plant disease resistance, wherein said polynucleotide has at least 90% sequence identity to the nucleotide sequence set forth in SEQ ID NO:1;
    (b) a polynucleotide encoding a polypeptide that enhances plant disease resistance, wherein said polynucleotide has at least 90% sequence identity to the nucleotide sequence set forth in SEQ ID NO:3;
    (c) a polynucleotide encoding a polypeptide that enhances plant disease resistance, wherein said polynucleotide has at least 90% sequence identity to the nucleotide sequence set forth in SEQ ID NO:5;
    (d) a polynucleotide encoding a polypeptide that enhances plant disease resistance, wherein said polynucleotide has at least 90% sequence identity to the nucleotide sequence set forth in SEQ ID NO:9;
    (e) a polynucleotide encoding a polypeptide that enhances plant disease resistance, wherein said polynucleotide has at least 90% sequence identity to the nucleotide sequence set forth in SEQ ID NO:15;
    (f) a polynucleotide encoding a polypeptide that enhances plant disease resistance, wherein said polynucleotide has at least 90% sequence identity to the nucleotide sequence set forth in SEQ ID NO:17;

(g) a polynucleotide encoding a polypeptide that enhances plant disease resistance, wherein said polynucleotide has at least 90% sequence identity to the nucleotide sequence set forth in SEQ ID NO:19;

(h) a polynucleotide encoding a polypeptide that enhances plant disease resistance, wherein said polynucleotide has at least 90% sequence identity to the nucleotide sequence set forth in SEQ ID NO:23;

(i) a polynucleotide encoding a polypeptide that enhances plant disease resistance, wherein said polynucleotide has at least 90% sequence identity to the nucleotide sequence set forth in SEQ ID NO:25;

(j) a polynucleotide encoding a polypeptide that enhances plant disease resistance, wherein said polynucleotide has at least 90% sequence identity to the nucleotide sequence set forth in SEQ ID NO:27;

(k) a polynucleotide encoding a polypeptide that enhances plant disease resistance, wherein said polynucleotide has at least 90% sequence identity to the nucleotide sequence set forth in SEQ ID NO:29;

(l) a polynucleotide encoding a polypeptide that enhances plant disease resistance, wherein said polynucleotide has at least 90% sequence identity to the nucleotide sequence set forth in SEQ ID NO:31;

(m) a polynucleotide encoding a polypeptide that enhances plant disease resistance, wherein said polynucleotide has at least 90% sequence identity to the nucleotide sequence set forth in SEQ ID NO:33; and (n) a polynucleotide that is complementary to the polynucleotide of (a), (b), (c), (d), (e), (f), (g), (h), (i), (j), (k), (l), or (m).

12. A recombinant expression cassette, comprising the nucleic acid of claim 11 operably linked to a promoter.

13. The recombinant expression cassette of claim 12, wherein said nucleic acid is operably linked in antisense orientation to said promoter.

14. A host cell containing the recombinant expression cassette of claim 12.

15. The host cell of claim 14, wherein said host cell is selected from the group consisting of bacterial cells, plant cells, and mammalian cells.

16. A transgenic plant cell comprising the nucleic acid molecule of claim 11.

17. A transgenic plant comprising the nucleic acid molecule of claim 11.

18. A trangenic seed from the trangenic plant of claim 17.

19. The transgenic seed of claim 18, wherein the seed is from *Zea mays*.

20. An isolated nucleic acid molecule comprising a polynucleotide selected from the group consisting of:

(a) the polynucleotide set forth in SEQ ID NO:1;
(b) the polynucleotide set forth in SEQ ID NO:15;
(c) the polynucleotide set forth in SEQ ID NO:25;
(d) a polynucleotide encoding the polypeptide set forth in SEQ ID NO:2;
(e) a polynucleotide encoding the polypeptide set forth in SEQ ID NO:16;
(f) a polynucleotide encoding the polypeptide set forth in SEQ ID NO:26; and
(g) a polynucleotide complementary to the polynucleotide of (a), (b), (c), (d), (e), or (f).

21. An isolated nucleic acid molecule comprising a polynucleotide selected from the group consisting of:

(a) the polynucleotide set forth in SEQ ID NO:3;
(b) the polynucleotide set forth in SEQ ID NO:17;
(c) the polynucleotide set forth in SEQ ID NO:27;
(d) a polynucleotide encoding the polypeptide set forth in SEQ ID NO:4;
(e) a polynucleotide encoding the polypeptide set forth in SEQ ID NO:18;
(f) a polynucleotide encoding the polypeptide set forth in SEQ ID NO:28; and
(g) a polynucleotide complementary to the polynucleotide of (a), (b), (c), (d), (e), or (f).

22. An isolated nucleic acid molecule comprising a polynucleotide selected from the group consisting of:

(a) the polynucleotide set forth in SEQ ID NO:5;
(b) the polynucleotide set forth in SEQ ID NO:19;
(c) the polynucleotide set forth in SEQ ID NO:29;
(d) a polynucleotide encoding the polypeptide set forth in SEQ ID NO:6;
(e) a polynucleotide encoding the polypeptide set forth in SEQ ID NO:20;
(f) a polynucleotide encoding the polypeptide set forth in SEQ ID NO:30; and
(g) a polynucleotide complementary to the polynucleotide of (a), (b), (c), (d), (e), or (f).

23. An isolated nucleic acid molecule comprising a polynucleotide selected from the group consisting of:

(a) the polynucleotide set forth in SEQ ID NO:7;
(b) the polynucleotide set forth in SEQ ID NO:21;
(c) the polynucleotide set forth in SEQ ID NO:31;
(d) a polynucleotide encoding the polypeptide set forth in SEQ ID NO:8;
(e) a polynucleotide encoding the polypeptide set forth in SEQ ID NO:22;
(f) a polynucleotide encoding the polypeptide set forth in SEQ ID NO:32; and
(g) a polynucleotide complementary to the polynucleotide of (a), (b), (c), (d), (e), or (f).

24. An isolated nucleic acid molecule comprising a polynucleotide selected from the group consisting of:

(a) the polynucleotide set forth in SEQ ID NO:9
(b) the polynucleotide set forth in SEQ ID NO:23;
(c) the polynucleotide set forth in SEQ ID NO:33;
(d) a polynucleotide encoding the polypeptide set forth in SEQ ID NO:10;
(e) a polynucleotide encoding the polypeptide set forth in SEQ ID NO:24;
(f) a polynucleotide encoding the polypeptide set forth in SEQ ID NO:34; and
(g) a polynucleotide complementary to the polynucleotide of (a), (b), (c), (d), (e), or (f).

25. An isolated nucleic acid molecule comprising a polynucleotide selected from the group consisting of:

(a) a polynucleotide encoding a polypeptide that enhances plant disease resistance, wherein said polynucleotide has at least 95% sequence identity to the nucleotide sequence set forth in SEQ ID NO:1;
(b) a polynucleotide encoding a polypeptide that enhances plant disease resistance, wherein said polynucleotide has at least 95% sequence identity to the nucleotide sequence set forth in SEQ ID NO:15;
(c) a polynucleotide encoding a polypeptide that enhances plant disease resistance, wherein said polynucleotide has at least 95% sequence identity to the nucleotide sequence set forth in SEQ ID NO:25; and (d) a polynucleotide that is complementary to the polynucleotide of (a), (b), or (c).

26. The isolated nucleic acid molecule of claim 11, wherein said isolated nucleic acid molecule comprises a polynucleotide selected from the group consisting of:

(a) a polynucleotide encoding a polypeptide that enhances plant disease resistance, wherein said polynucleotide has at least 95% sequence identity to the nucleotide sequence set forth in SEQ ID NO:3;

(b) a polynucleotide encoding a polypeptide that enhances plant disease resistance, wherein said polynucleotide has at least 95% sequence identity to the nucleotide sequence set forth in SEQ ID NO:17;

(c) a polynucleotide encoding a polypeptide that enhances plant disease resistance, wherein said polynucleotide has at least 95% sequence identity to the nucleotide sequence set forth in SEQ ID NO:27; and (d) a polynucleotide that is complementary to the polynucleotide of (a), (b), or (c).

27. The isolated nucleic acid molecule of claim 11, wherein said isolated nucleic acid molecule comprises a polynucleotide selected from the group consisting of:

(a) a polynucleotide encoding a polypeptide that enhances plant disease resistance, wherein said polynucleotide has at least 95% sequence identity to the nucleotide sequence set forth in SEQ ID NO:5;

(b) a polynucleotide encoding a polypeptide that enhances plant disease resistance, wherein said polynucleotide has at least 95% sequence identity to the nucleotide sequence set forth in SEQ ID NO:19;

(c) a polynucleotide encoding a polypeptide that enhances plant disease resistance, wherein said polynucleotide has at least 95% sequence identity to the nucleotide sequence set forth in SEQ ID NO:29; and (d) a polynucleotide that is complementary to the polynucleotide of (a), (b), or (c).

28. An isolated nucleic acid molecule comprising a polynucleotide selected from the group consisting of:

(a) a polynucleotide encoding a polypeptide that enhances plant disease resistance, wherein said polynucleotide has at least 95% sequence identity to the nucleotide sequence set forth in SEQ ID NO:7;

(b) a polynucleotide encoding a polypeptide that enhances plant disease resistance, wherein said polynucleotide has at least 95% sequence identity to the nucleotide sequence set forth in SEQ ID NO:21;

(c) a polynucleotide encoding a polypeptide that enhances plant disease resistance, wherein said polynucleotide has at least 95% sequence identity to the nucleotide sequence set forth in SEQ ID NO:31; and (d) a polynucleotide that is complementary to the polynucleotide of (a), (b), or (c).

29. The isolated nucleic acid molecule of claim 11, wherein said isolated nucleic acid molecule comprises a polynucleotide selected from the group consisting of:

(a) a polynucleotide encoding a polypeptide that enhances plant disease resistance, wherein said polynucleotide has at least 95% sequence identity to the nucleotide sequence set forth in SEQ ID NO:9;

(b) a polynucleotide encoding a polypeptide that enhances plant disease resistance, wherein said polynucleotide has at least 95% sequence identity to the nucleotide sequence set forth in SEQ ID NO:23;

(c) a polynucleotide encoding a polypeptide that enhances plant disease resistance, wherein said polynucleotide has at least 95% sequence identity to the nucleotide sequence set forth in SEQ ID NO:33; and (d) a polynucleotide that is complementary to the polynucleotide of (a), (b), or (c).

* * * * *

UNITED STATES PATENT AND TRADEMARK OFFICE
CERTIFICATE OF CORRECTION

PATENT NO.     : 6,555,732 B1
DATED          : April 29, 2003
INVENTOR(S)    : Duvick et al.

It is certified that error appears in the above-identified patent and that said Letters Patent is hereby corrected as shown below:

Column 111,
Line 43, after "bacterial cells" insert -- yeast cells, --.

Signed and Sealed this

Twenty-third Day of September, 2003

JAMES E. ROGAN
*Director of the United States Patent and Trademark Office*